United States Patent
Quayle et al.

(10) Patent No.: US 11,311,540 B2
(45) Date of Patent: Apr. 26, 2022

(54) INCREASING EXPRESSION OF INTERFERON REGULATED GENES WITH COMBINATIONS OF HISTONE DEACETYLASE INHIBITORS AND IMMUNOMODULATORY DRUGS

(71) Applicant: ACETYLON PHARMACEUTICALS, INC., Summit, NJ (US)

(72) Inventors: Steven Norman Quayle, Brookline, MA (US); Jeffrey R. Shearstone, Framingham, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 16/076,590

(22) PCT Filed: Feb. 17, 2017

(86) PCT No.: PCT/US2017/018445
§ 371 (c)(1),
(2) Date: Aug. 8, 2018

(87) PCT Pub. No.: WO2017/143237
PCT Pub. Date: Aug. 24, 2017

(65) Prior Publication Data
US 2019/0046529 A1 Feb. 14, 2019

Related U.S. Application Data

(60) Provisional application No. 62/296,366, filed on Feb. 17, 2016.

(51) Int. Cl.
*A61K 31/505* (2006.01)
*A61K 31/454* (2006.01)
*A61P 35/00* (2006.01)

(52) U.S. Cl.
CPC .......... *A61K 31/505* (2013.01); *A61K 31/454* (2013.01); *A61P 35/00* (2018.01)

(58) Field of Classification Search
CPC ...... A61K 31/505; A61K 31/454; A61P 35/00
USPC ........................................................ 514/275
See application file for complete search history.

(56) References Cited

U.S. PATENT DOCUMENTS

| | | |
|---|---|---|
| 8,148,526 B1 | 4/2012 | Van Duzer et al. |
| 8,394,810 B2 | 3/2013 | Van Duzer et al. |
| 8,609,678 B2 | 12/2013 | Van Duzer et al. |
| 8,791,235 B2* | 7/2014 | Ahlfors .................. A61P 19/02 530/331 |
| 2015/0105358 A1* | 4/2015 | Quayle ................. A61K 31/505 514/171 |
| 2015/0320758 A1 | 11/2015 | Verner et al. |

FOREIGN PATENT DOCUMENTS

| | | | |
|---|---|---|---|
| WO | WO 2011/091213 | * | 7/2011 |
| WO | WO 2013/013113 | * | 1/2013 |
| WO | WO 2015/039083 | * | 3/2015 |
| WO | WO 2015/085172 A2 | | 6/2015 |

OTHER PUBLICATIONS

Kaje et al. Histone deacetylase inhibitors in multiple myeloma: rationale and evidence for theri use in combination therapy. Clinical Lymphoma, Myeloma & Leukemia, vol. 13, No. 4, 370-6. Aug. 2013.*
Sausville et al. (Cancer Research, 2006, vol. 66, pp. 3351-3354).*
Johnson et al. (British J. of Cancer, 2001, 84(10):1424-1431).*
International Search Report and Written Opinion in related PCT Application No. PCT/US2017/018445, dated Jul. 11, 2017 (13 pages).
ClinicalTrials.gov "ACY-1215 (Ricolinostat) in Combination with Pomalidomide and Low-dose Dex in Relapsed-and-Refratory Multiple Myeloma," U.S. National Institutes of Health. Identifier: NCT01997840. Accessible on the Internet at URL: https://clinicaltrials.govict2/show/NCT01997840?term=ricolinostat&rank=1. [Last Accessed Oct. 22, 2015].
ClinicalTrials.gov "Phase Ib Study Evaluating ACY-1215 (Ricolinostat) in Combination with Pomalidomide and Dexamethasone in Relapsed or Relapsed-and-Refractory Multiple Myeloma," U.S. National Institutes of Health. Identifier: NCT02189343. Accessible on the Internet at URL: https://clinicaltrials.govict2/show/NCT02189343?term=ricolinostat&rank=2. [Last Accessed Oct. 22, 2015].
ClinicalTrials.gov "Study of ACY-1215 in Combination with Lenalidomide, and Dexamethasone in Multiple Myeloma," U.S. National Institutes of Health. Identifier: NCT01583283. Accessible on the Internet at URL: https://clinicaltrials.gov/ct2/show/NCT01583283?term=ricolinostat&rank=6. [Last Accessed Oct. 22, 2015].
Costello et al. (Dec. 2012) "Evidence for Changes in RREB-1, ZIP3, and Zinc in the Early Development of Pancreatic Adenocarcinoma," J. Gastrointest. Canc. 43:570-578.
Holien et al. (Sep. 20, 2012) "Addiction to c-MYC in multiple myeloma," Blood. 120:2450-2453.

(Continued)

*Primary Examiner* — Yevgeny Valenrod
(74) *Attorney, Agent, or Firm* — Lathrop GPM LLP; Brian C. Trinque

(57) ABSTRACT

Provided herein is a combination comprising an HDAC inhibitor and an IMiD for increasing interferon regulated gene expression or decreasing c-MYC gene expression in a cancer cell or tumor in a subject in need thereof. Increasing interferon regulated gene expression may result in increased recognition of tumors by innate or adaptive immune system and an increase in programmed cell death (apoptosis) gene expression, increasing apoptosis in cancer cells and tumors. The cells can be multiple myeloma cells or diffuse large B-cell lymphoma cells. Also provided are methods for treating myelodysplastic syndromes/acute myeloid leukemia (MDS/AML) or pathogen infections in a subject in need thereof comprising administering to the subject an effective amount of HDAC inhibitor and an IMiD. The HDAC inhibitor can be an HDAC6-selective inhibitor.

7 Claims, 35 Drawing Sheets

(56) References Cited

OTHER PUBLICATIONS

Raje et al. (Dec. 8, 2011) "Rocilinostat (ACY-1215), a Selective HDAC6 Inhibitor, Alone and in Combination with Bortezomib in Multiple Myeloma: Preliminary Results From the First-in-Humans Phase I/II Study," In; The 54th ASH Annual Meeting and Exposition. Paper No. 4061. Retreived Online at https://ash.confex.com/ash/2012/webprogram/ Paper52013.html.—Abstract Only.
Raje et al. (Jun. 2014) "Ricolinostat (ACY-1215), the first selective histone deacetylase 6 inhibitor, is active and well tolerated in combination with lenalidomide or bortezomib in patients with Refractory myeloma," Haematologica. 99(s1) Paper No. 258. pp. 110-111.
Richter et al. (Dec. 2011) "Salvage Therapy with Vorinostat, Lenalidomide, and Dexamethasone (ZRD) in Lenalidomide/Dexamethasone Relapsed/Refractory Multiple Myeloma,:Salvage Therapy with Vorinostat, Lenalidomide, and Dexamethasone (ZRD) in Lenalidomide/Dexamethasone Relapsed/Refractory Multiple Myeloma," In; The 53rd ASH Annual Meeting and Exposition. Paper No. 3986. Retreived Online at https://ash.confex.com/ash/2011/webprogram/Paper43422.html.—Abstract Only.
U.S. Appl. No. 13/010,974 / 2011/0300134 / U.S. Pat. No. 8,394,810, filed Jan. 21, 2011 / Dec. 8, 2011 / Mar. 12, 2013, John H. van Duzer.
U.S. Appl. No. 13/310,168 / 2012/0083504 / U.S. Pat. No. 8,148,526, filed Dec. 2, 2011 / Apr. 5, 2012 / Apr. 3, 2012, John H. van Duzer.
U.S. Appl. No. 13/437,672 / 2012/0190693 / U.S. Pat. No. 8,609,678, filed Apr. 2, 2012 / Jul. 26, 2012 / Dec. 17, 2013, John H. van Duzer.
U.S. Appl. No. 13/296,748 / 2012/0121502 / U.S. Pat. No. 8,614,223, filed Dec. 24, 2013 / May 17, 2012 / Dec. 24, 2013, John H. Van Duzer.
U.S. Appl. No. 14/082,472 / 2014/0142104 / U.S. Pat. No. 9,409,890, filed Nov. 18, 2013 / May 22, 2014 / Aug. 9, 2016, John H. van Duzer.
U.S. Appl. No. 13/866,367 / 2014/0011767 / U.S. Pat. No. 9,663,825, filed Apr. 19, 2013 / 2014/0011767 / May 30, 2017, Min Yang.
U.S. Appl. No. 15/497,397 / 2017/0327895, filed Apr. 26, 2017 / Nov. 16, 2017, Min Yang.
U.S. Appl. No. 14/508,072 / 2015/0105358, filed Oct. 7, 2014 / Apr. 16, 2015, Steven Norman Quayle.
U.S. Appl. No. 14/506,889 / 2015/0099744 / U.S. Pat. No. 9,403,779, filed Oct. 6, 2014 / Apr. 9, 2015 / Aug. 2, 2016, David Lee Tamang.
U.S. Appl. No. 15/189,554 / 2017/0020872, filed Jun. 22, 2016 / Jan. 26, 2017, David Lee Tamang.
U.S. Appl. No. 14/508,135 / 2015/0105409, filed Oct. 7, 2014 / Apr. 16, 2015, Steven Norman Quayle.
U.S. Appl. No. 14/509,360 / 2015/0105383, filed Oct. 8, 2014 / Apr. 16, 2015, Steven Norman Quayle.
U.S. Appl. No. 14/510,711 / 2015/0105384 / U.S. Pat. No. 9,278,963, filed Oct. 9, 2014 / Apr. 16, 2015 / Mar. 8, 2016, John H. van Duzer.
U.S. Appl. No. 14/631,971 / 2015/0239869 / U.S. Pat. No. 9,464,073, filed Feb. 26, 2015 / Aug. 27, 2015 / Oct. 11, 2016, Ralph Mazitschek.
U.S. Appl. No. 15/260,855 / 2017/0096413 / U.S. Pat. No. 9,884,850, filed Sep. 9, 2016 / Apr. 6, 2017 / Feb. 6, 2018, Ralph Mazitschek.
U.S. Appl. No. 14/558,941 / 2015/0150871 / U.S. Pat. No. 9,949,972, filed Dec. 3, 2014 / Jun. 4, 2015 / Apr. 24, 2018, Steven Norman Quayle.
U.S. Appl. No. 14/576,313 / 2015/0176076, filed Dec. 19, 2014 / Jun. 25, 2015, Min Yang.
U.S. Appl. No. 14/792,046 / 2016/0030458 / U.S. Pat. No. 9,833,466, filed Jul. 6, 2015 / Feb. 4, 2016 / Dec. 5, 2017, Simon S. Jones.
U.S. Appl. No. 14/959,473 / 2016/0158232 / U.S. Pat. No. 9,937,174, filed Dec. 4, 2015 / Jun. 9, 2016 / Apr. 10, 2018, Samantha Pozzi.
U.S. Appl. No. 15/176,826 / 2016/0355486 / U.S. Pat. No. 10,144,714, filed Jun. 8, 2016 / Dec. 8, 2016 / Dec. 4, 2018, Farzaneh Seyedi.
U.S. Appl. No. 15/176,788 / 2017/0001965, filed Jun. 8, 2016 / Jan. 5, 2017, John H. van Duzer.
U.S. Appl. No. 16/076,590 / 2019/0046529, filed Feb. 17, 2017 / Feb. 14, 2019, Steven Norman Quayle.
U.S. Appl. No. 16/093,278 / 2019/0209559, filed Apr. 19, 2017 / Jul. 11, 2019, Simon S. Jones.
U.S. Appl. No. 16/463,140 / 2019/0282573, filed Nov. 21, 2017 / Sep. 9, 2019, Steven Quayle.
U.S. Appl. No. 15/670,743 / 2018/0036306, filed Aug. 7, 2017 / Feb. 8, 2018, Simon Steward Jones.
U.S. Appl. No. 16/305,567, filed Jun. 9, 2017, Kwok-kin Wong.
U.S. Appl. No. 16/377,873 / 2019/0262337, filed Nov. 3, 2017 / Aug. 29, 2019, Nathan Moore.
U.S. Appl. No. 15/807,782 / 2018/0127356 / U.S. Pat. No. 10,370,324, filed Nov. 9, 2017 / May 10, 2018 / Aug. 6, 2019, John H. van Duzer.

* cited by examiner

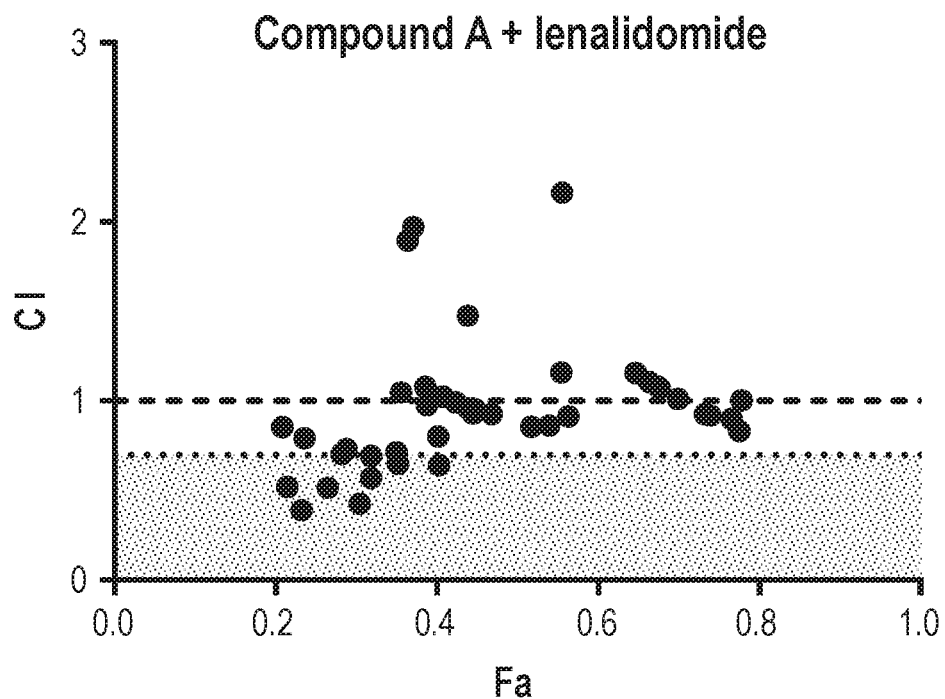
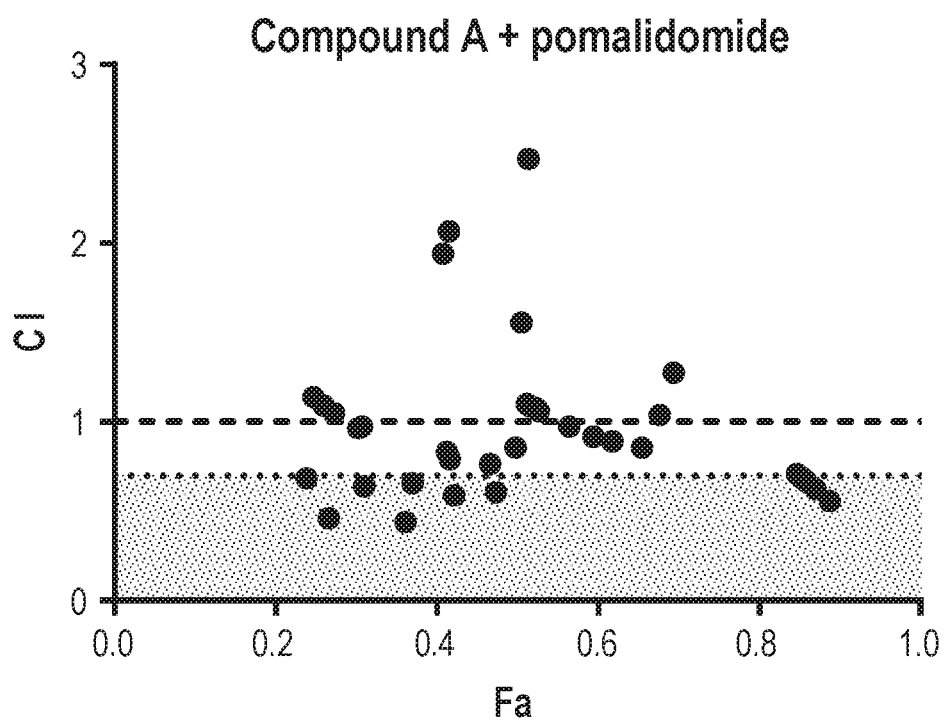
Fig. 1A

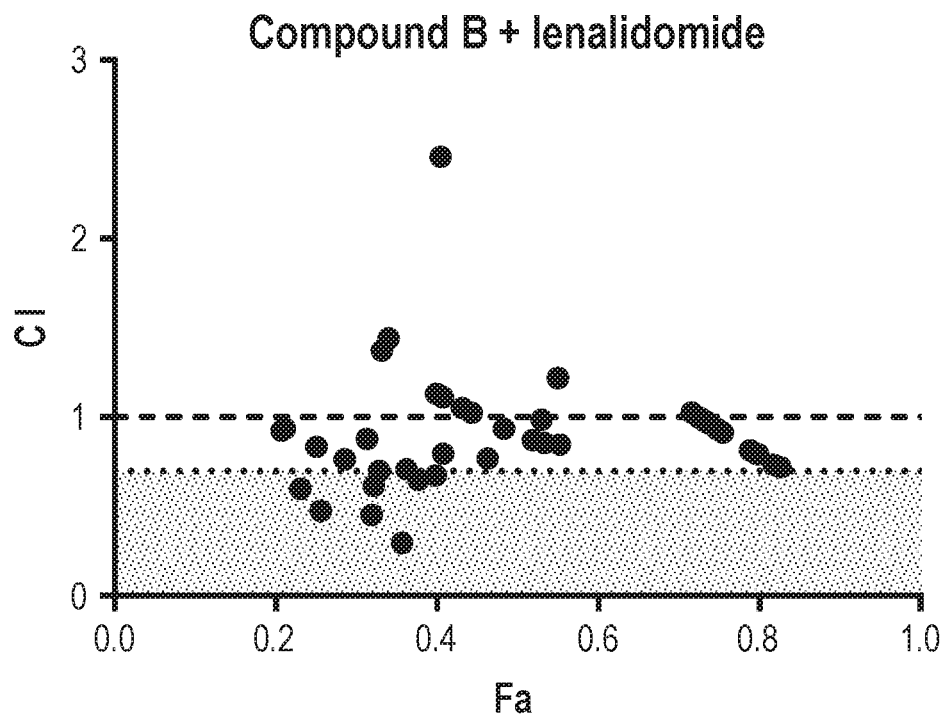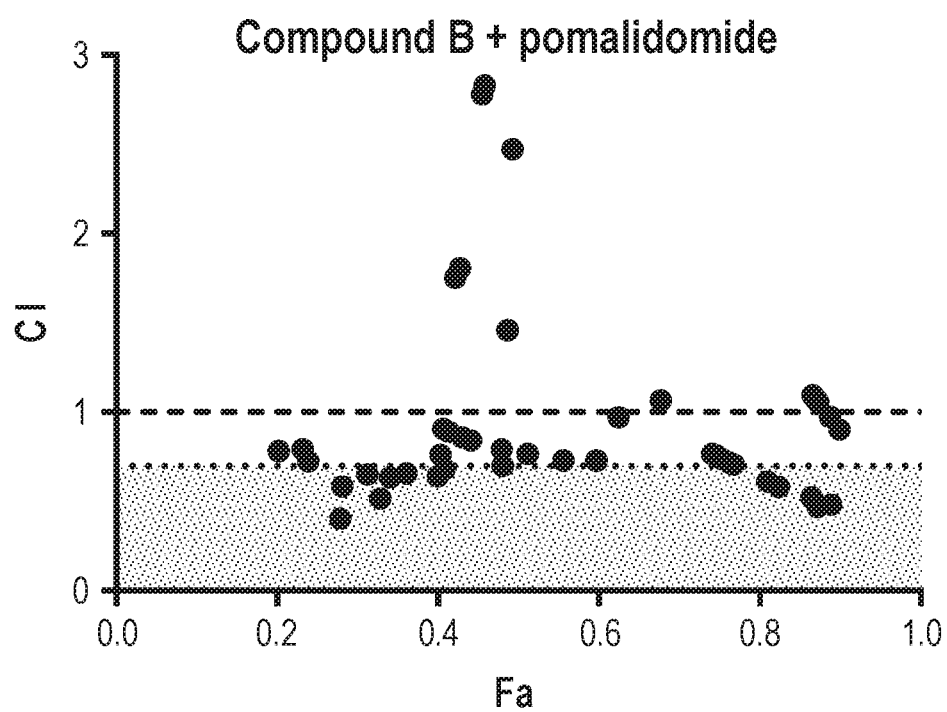
Fig. 1B

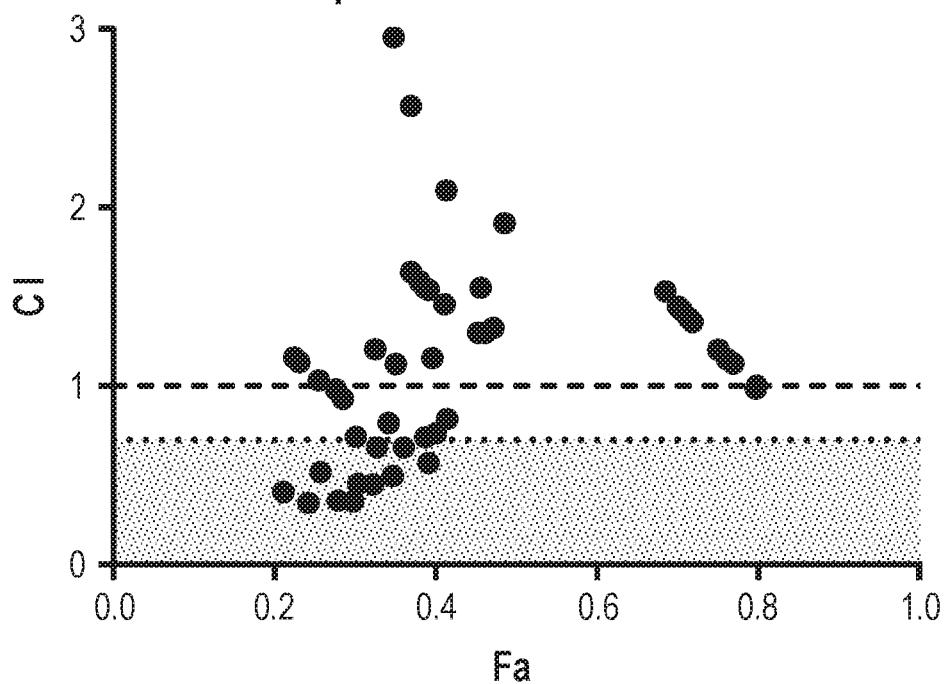
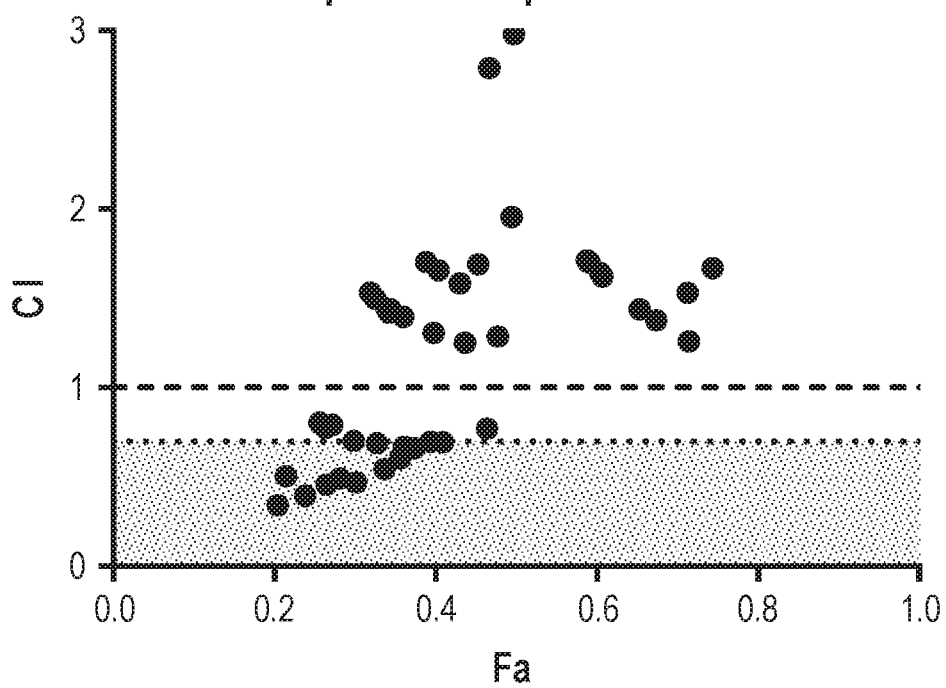
Fig. 1C

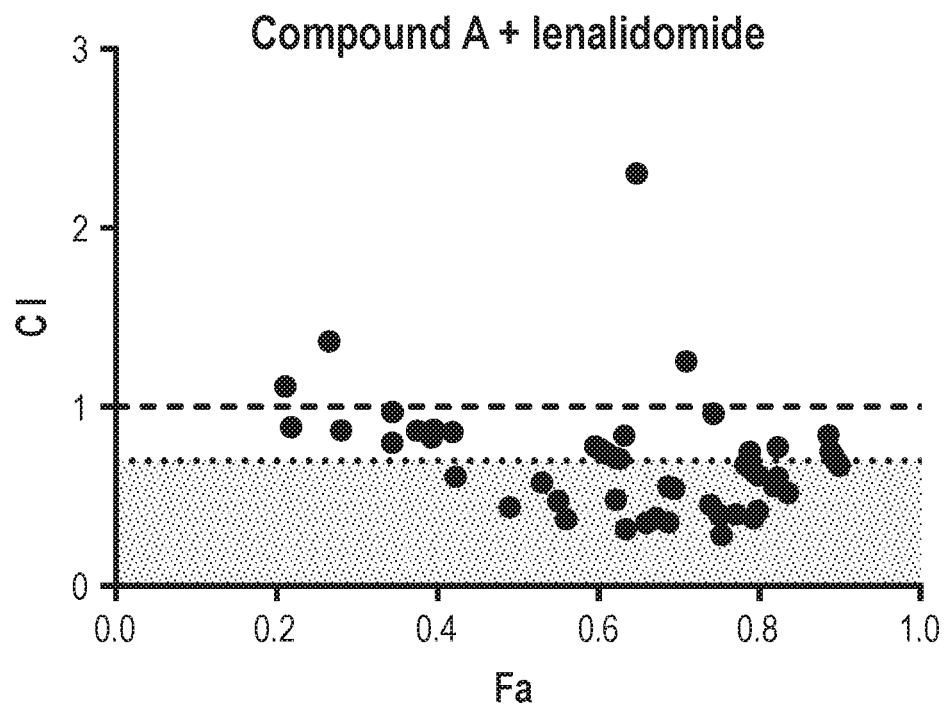
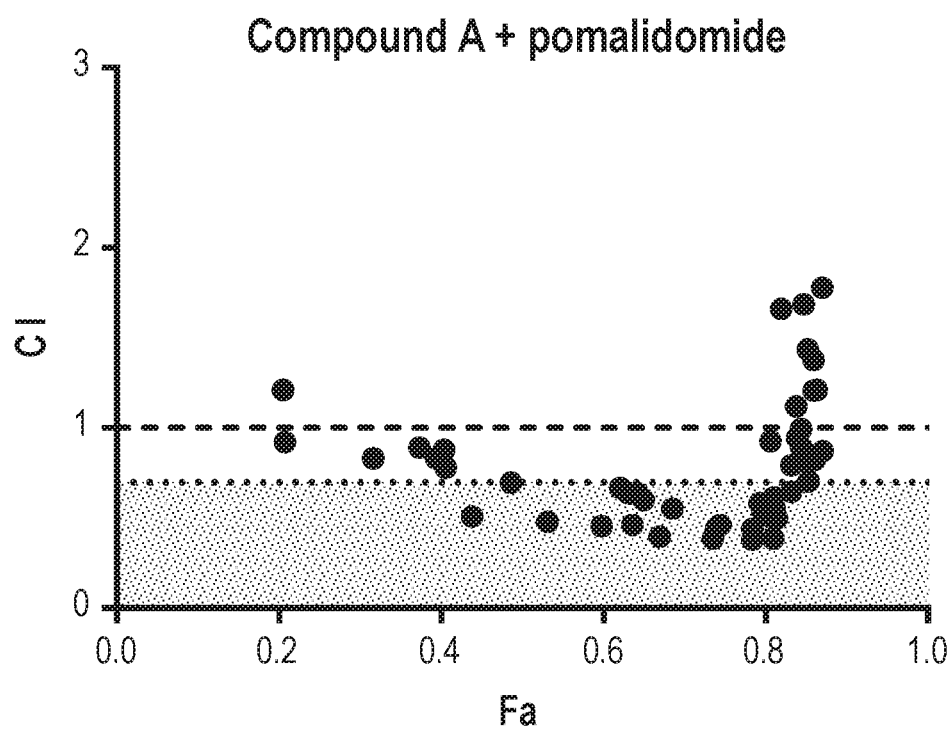
Fig. 2A

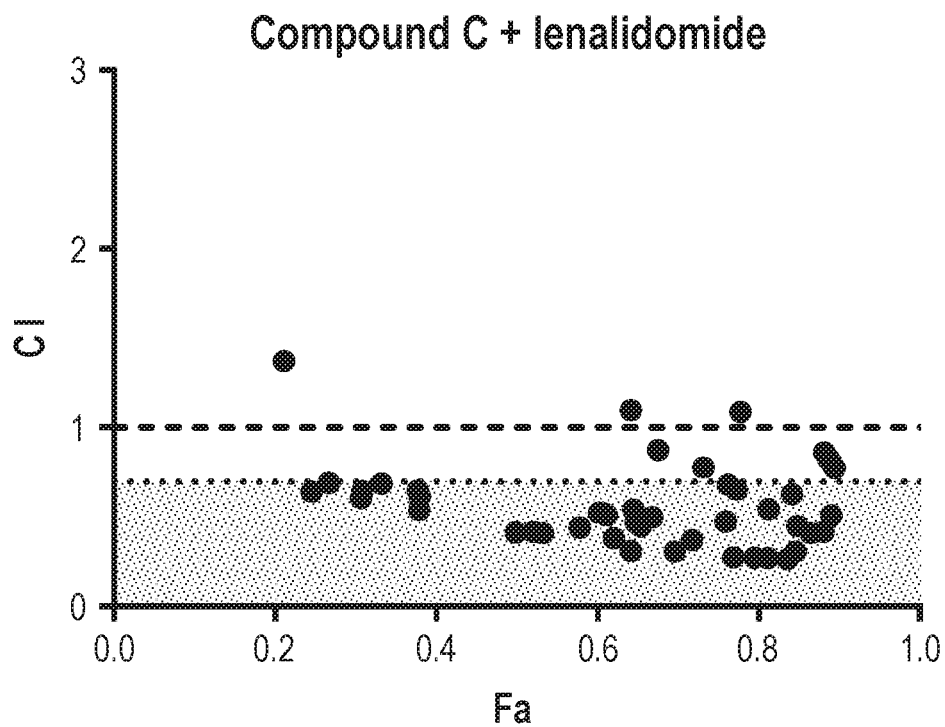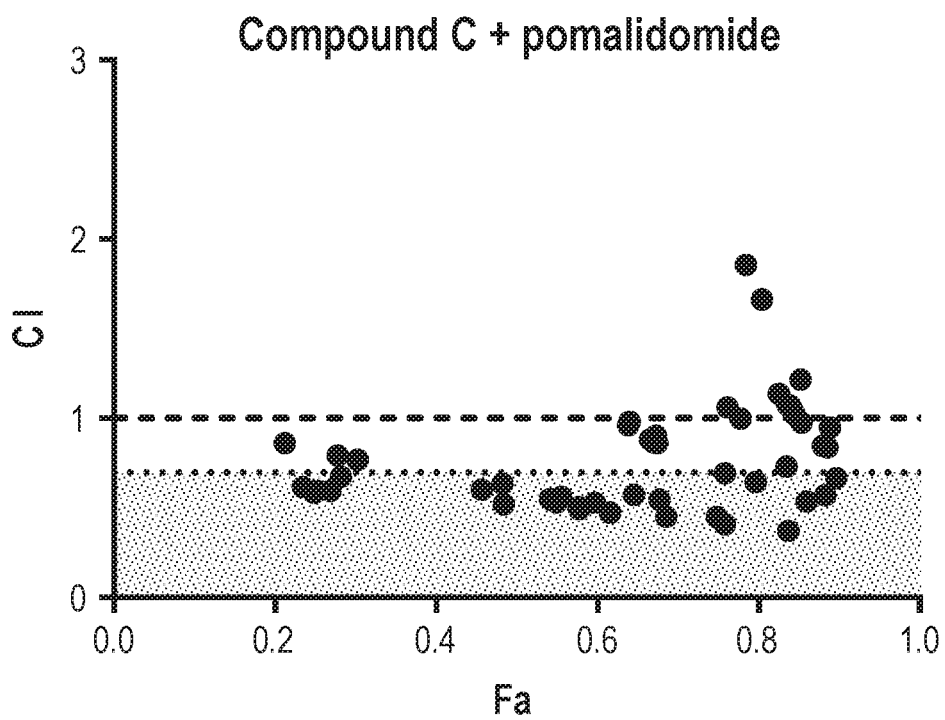
Fig. 2C

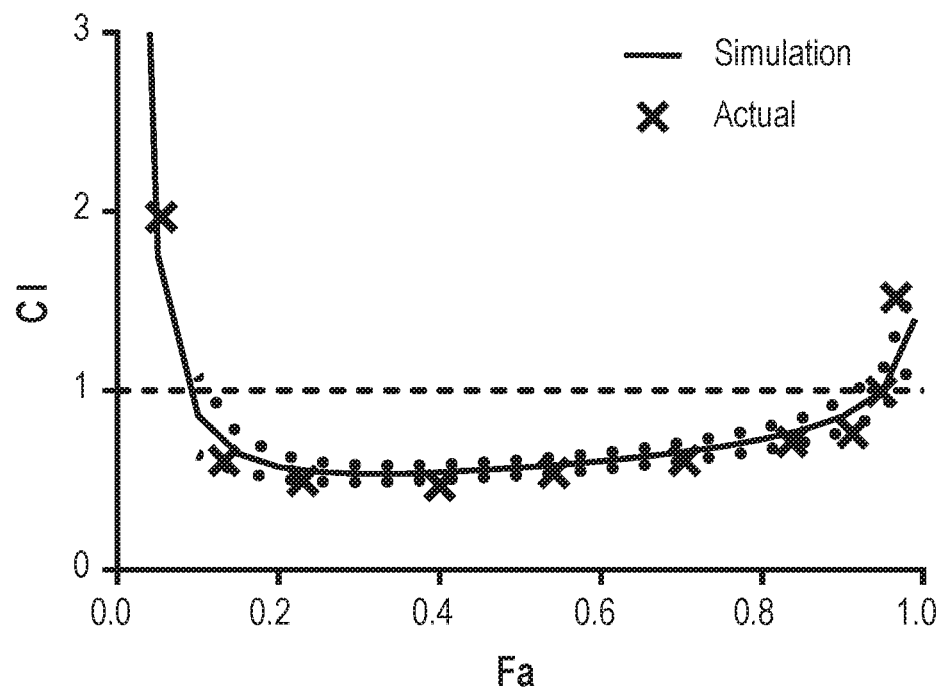
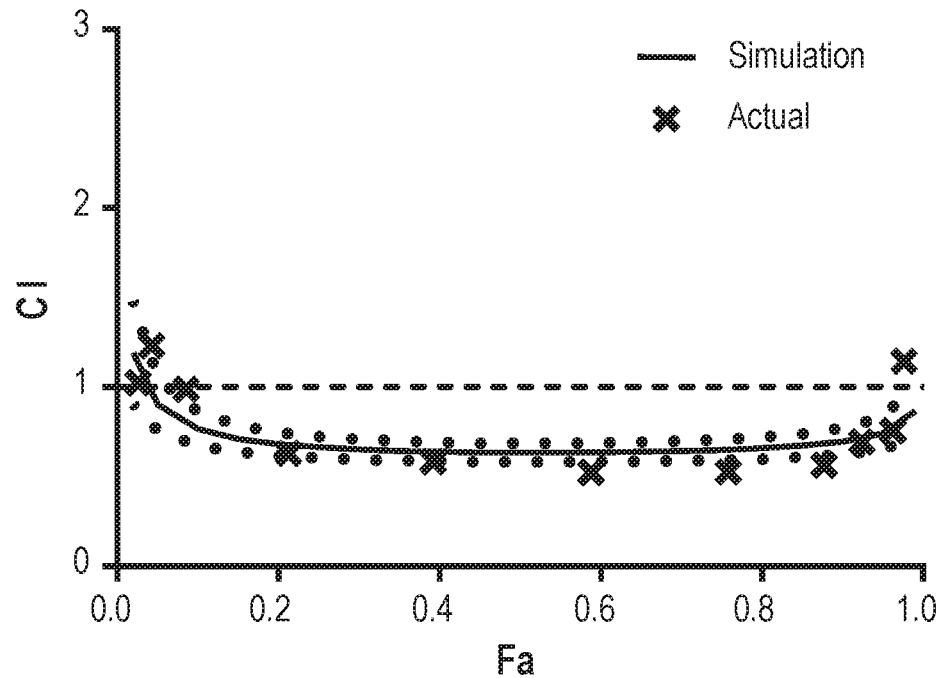
Fig. 5A

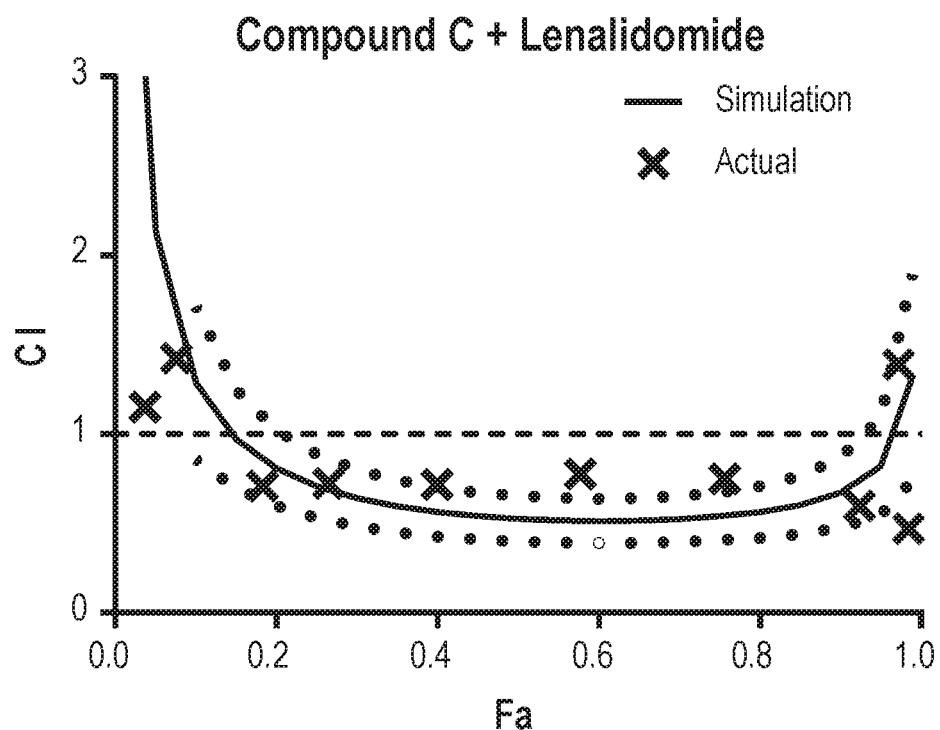
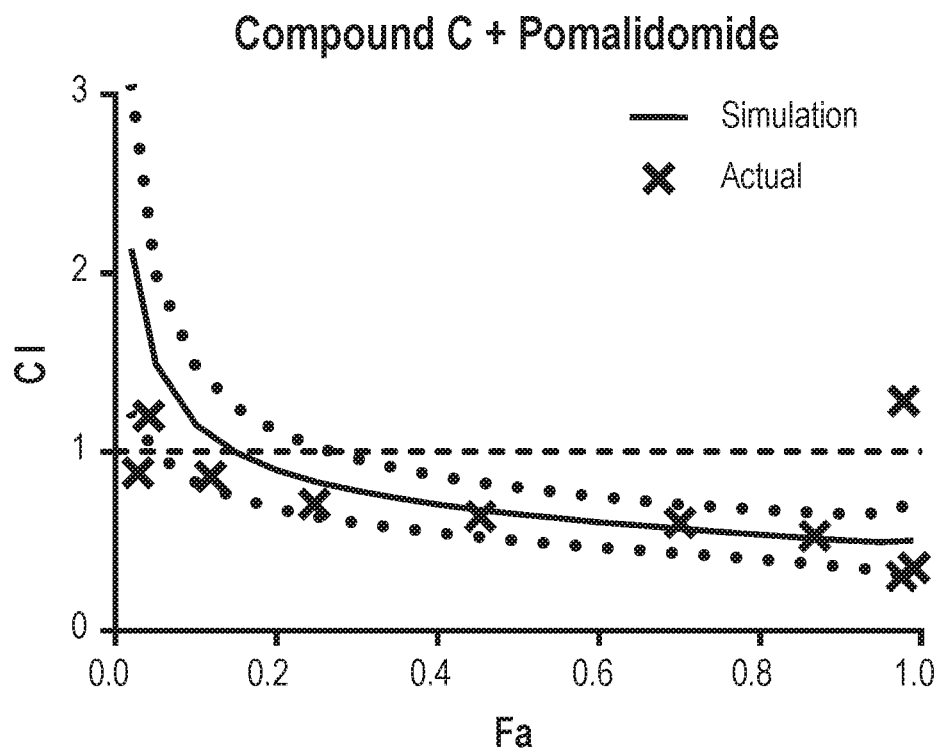
Fig. 5B

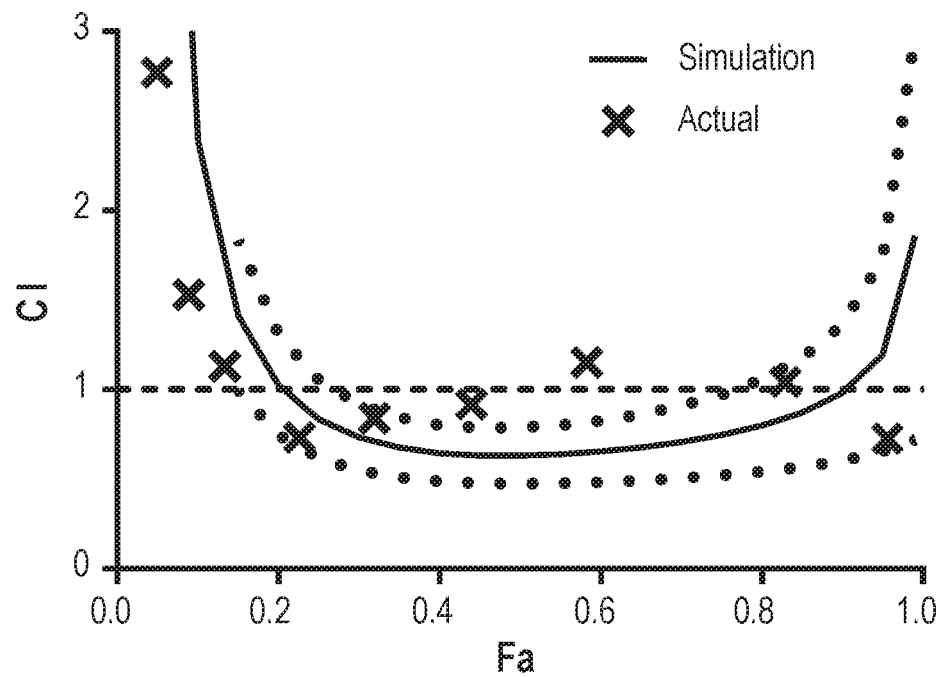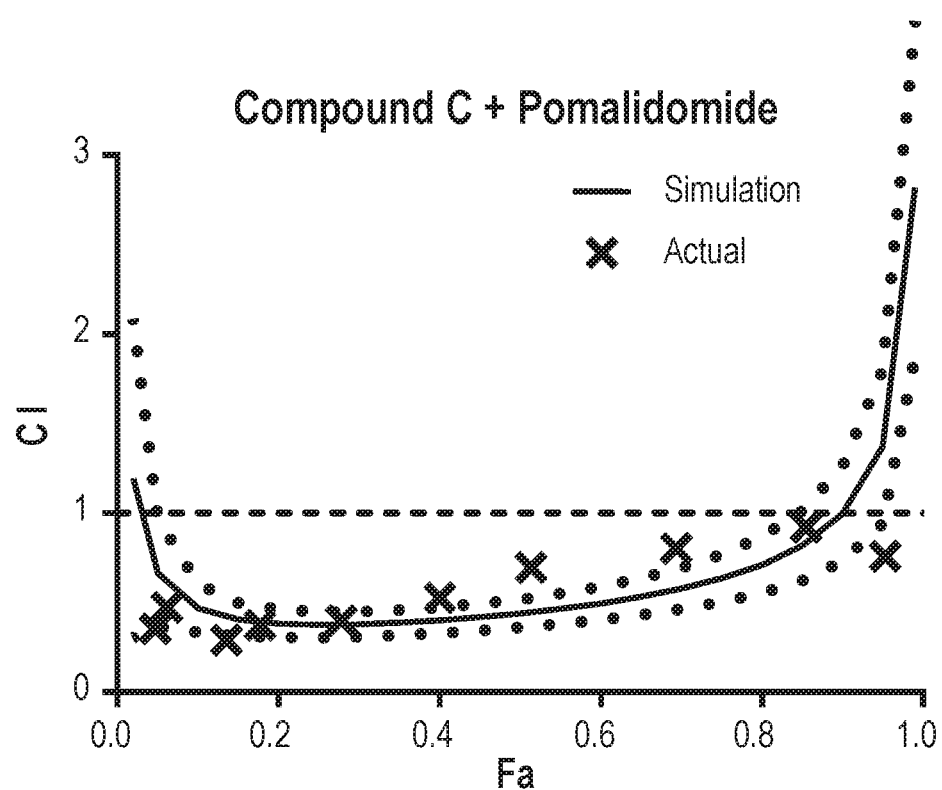
*Fig. 5D*

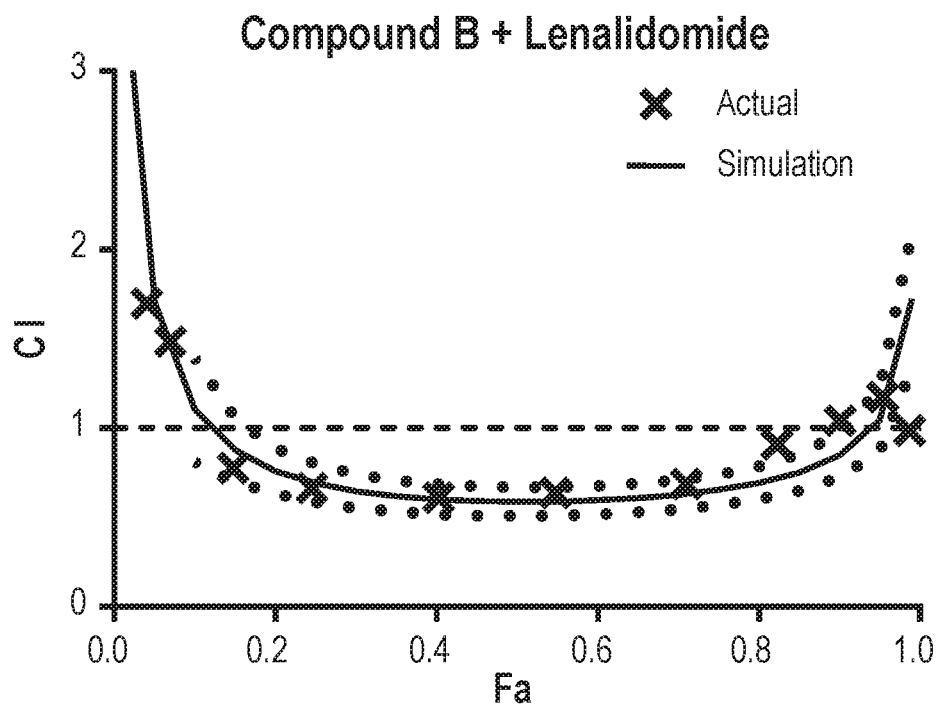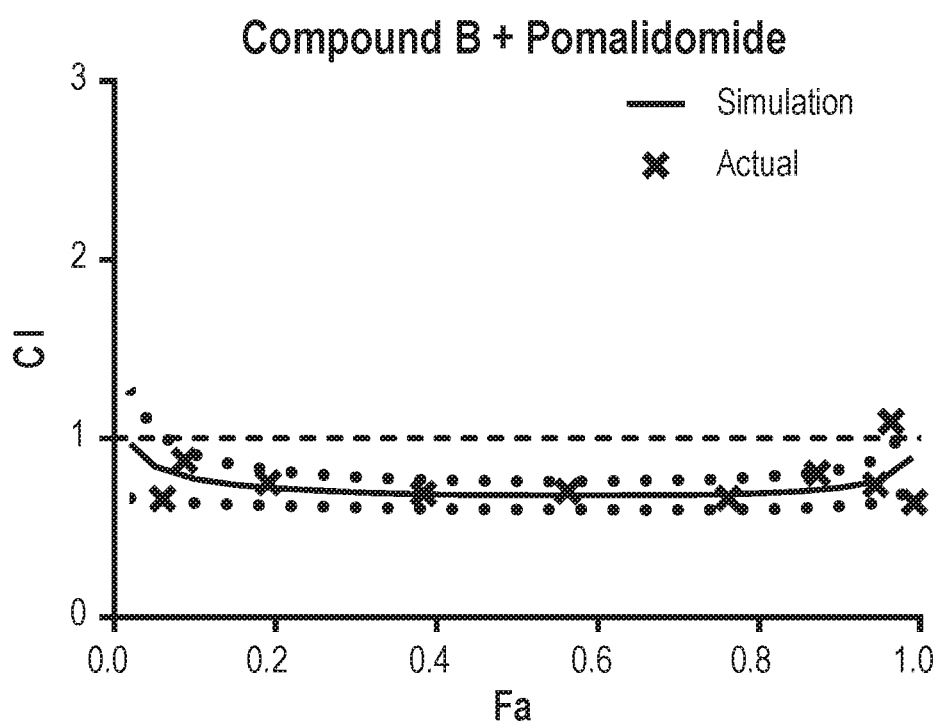
Fig. 5E

| Comparison | | Enriched gene sets | | | | | |
|---|---|---|---|---|---|---|---|
| | | GS follow link to MSigDB | SIZE | ES | NES | NOM p-val | FDR q-val |
| Positive enrichment | Combo vs. Compound A | 1 HALLMARK_INTERFERON_GAMMA_RESPONSE | 196 | 0.67 | 2.91 | 0.000 | 0.000 |
| | | 2 HALLMARK_INTERFERON_ALPHA_RESPONSE | 96 | 0.75 | 2.89 | 0.000 | 0.000 |
| | | 3 HALLMARK_PROTEIN_SECRETION | 94 | 0.65 | 2.55 | 0.000 | 0.000 |
| | | 4 HALLMARK_APOPTOSIS | 157 | 0.49 | 2.04 | 0.000 | 0.001 |
| | | 5 HALLMARK_TGF_BETA_SIGNALING | 54 | 0.54 | 1.94 | 0.000 | 0.001 |
| | Combo vs. Pom | | SIZE | ES | NES | NOM p-val | FDR q-val |
| | | 1 HALLMARK_INTERFERON_ALPHA_RESPONSE | 96 | 0.71 | 2.62 | 0.000 | 0.000 |
| | | 2 HALLMARK_INTERFERON_GAMMA_RESPONSE | 196 | 0.55 | 2.22 | 0.000 | 0.000 |
| | | 3 HALLMARK_E2F_TARGETS | 192 | 0.44 | 1.77 | 0.000 | 0.006 |
| | | 4 HALLMARK_MITOTIC_SPINDLE | 196 | 0.42 | 1.72 | 0.000 | 0.009 |
| | | 5 HALLMARK_APOPTOSIS | 157 | 0.41 | 1.63 | 0.000 | 0.018 |
| Negative enrichment | Combo vs. Compound A | | SIZE | ES | NES | NOM p-val | FDR q-val |
| | | 1 HALLMARK_E2F_TARGETS | 192 | -0.54 | -2.55 | 0.000 | 0.000 |
| | | 2 HALLMARK_G2M_CHECKPOINT | 194 | -0.53 | -2.51 | 0.000 | 0.000 |
| | | 3 HALLMARK_MYC_TARGETS_V2 | 54 | -0.62 | -2.34 | 0.000 | 0.000 |
| | | 4 HALLMARK_MYC_TARGETS_V1 | 186 | -0.39 | -1.84 | 0.000 | 0.001 |
| | | 5 HALLMARK_KRAS_SIGNALING_DN | 196 | -0.32 | -1.56 | 0.000 | 0.009 |
| | Combo vs. Pom | | SIZE | ES | NES | NOM p-val | FDR q-val |
| | | 1 HALLMARK_MYC_TARGETS_V2 | 54 | -0.64 | -2.35 | 0.000 | 0.000 |
| | | 2 HALLMARK_UNFOLDED_PROTEIN_RESPONSE | 108 | -0.40 | -1.67 | 0.000 | 0.005 |

Fig. 11

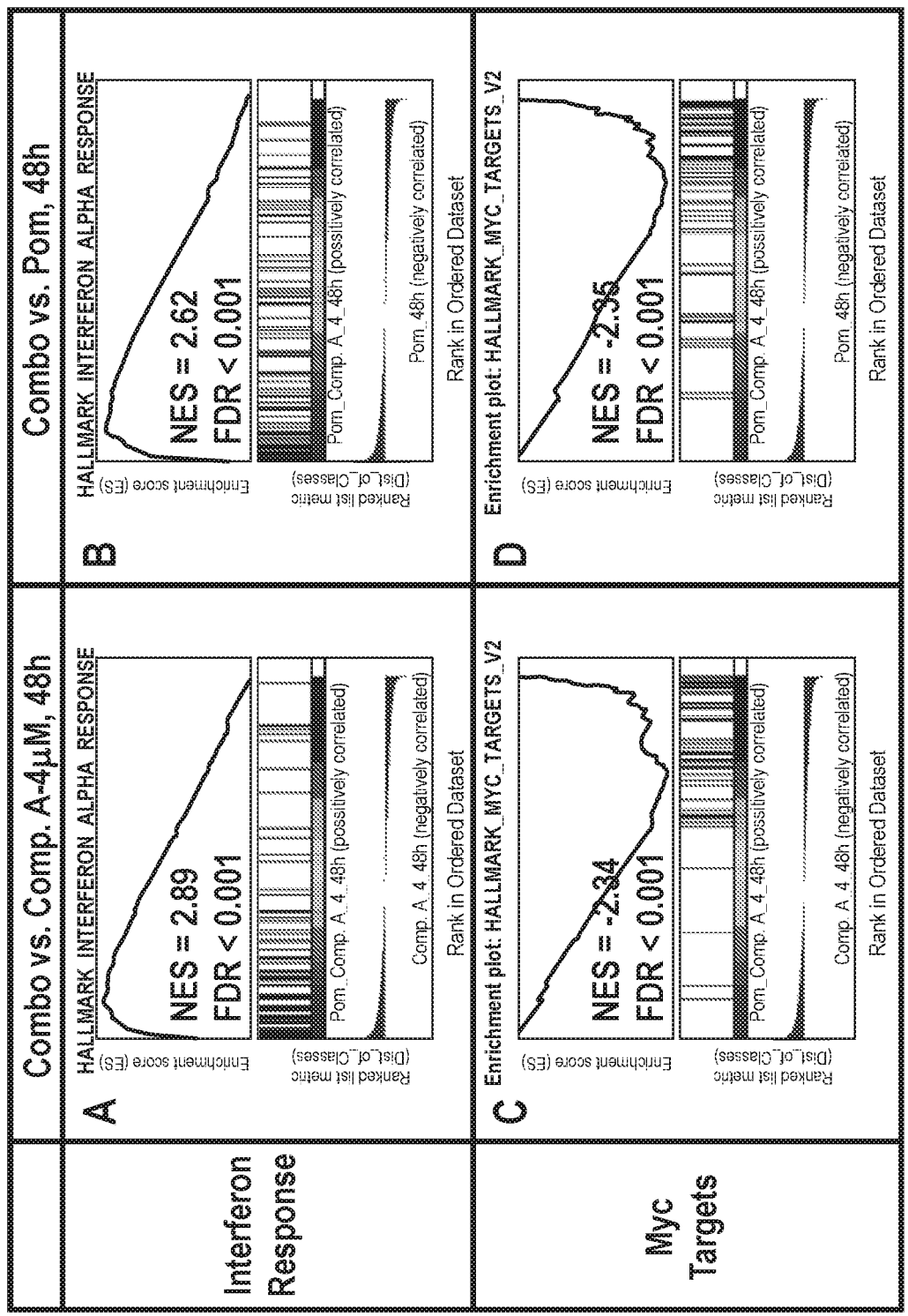
Fig. 12A-D

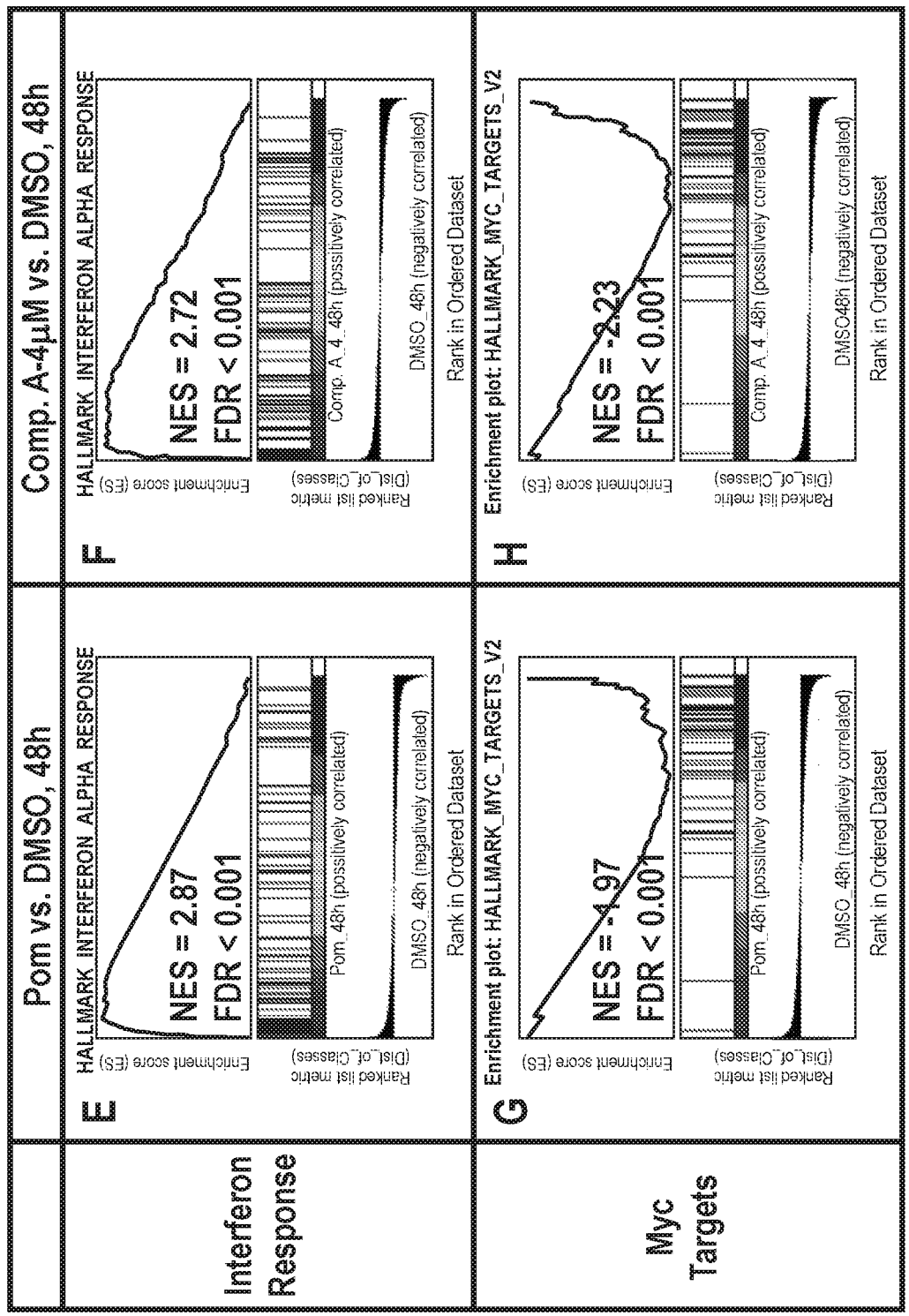
Fig. 12E-H

Fig. 13A-F

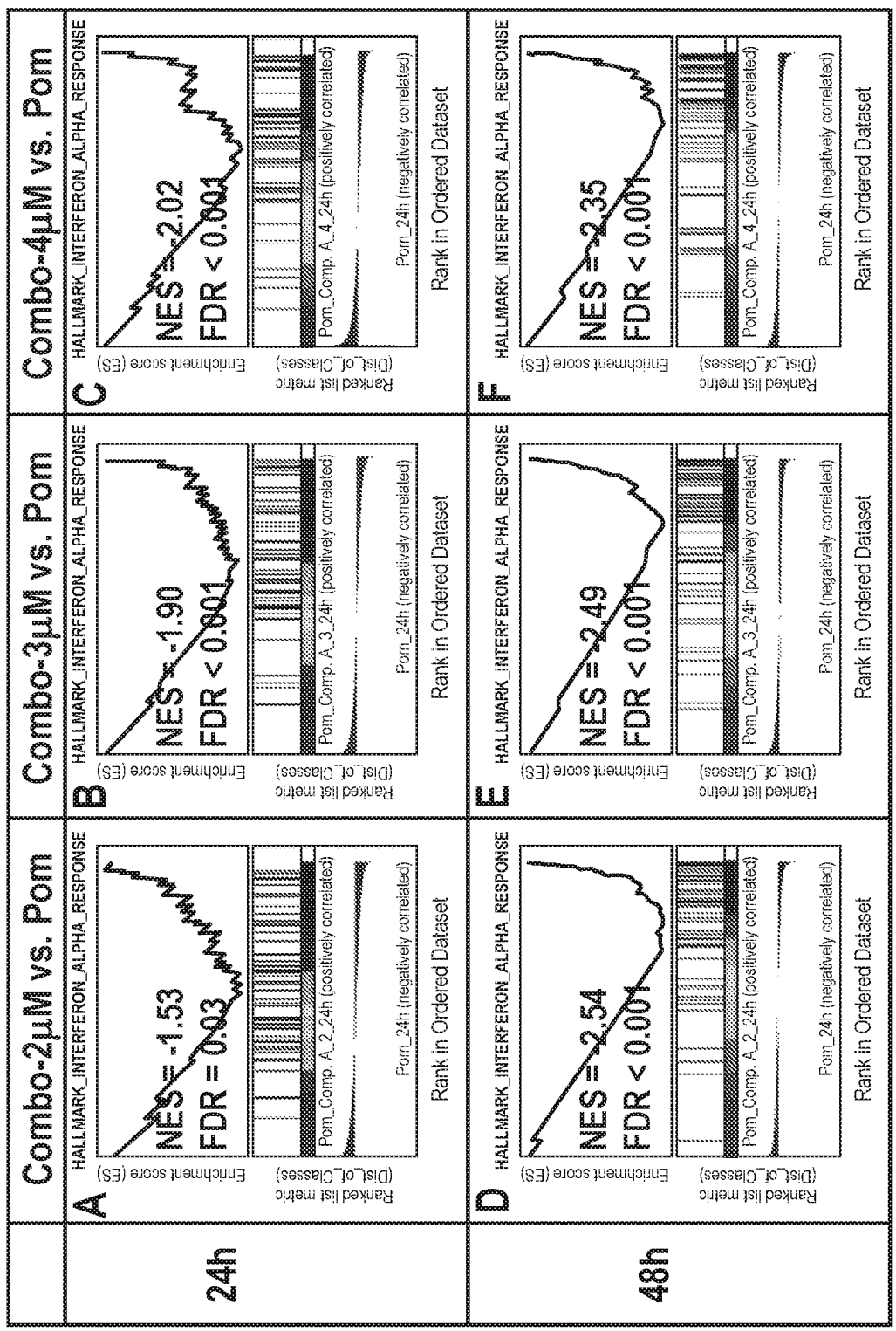
Fig. 14A-F

INCREASING EXPRESSION OF INTERFERON REGULATED GENES WITH COMBINATIONS OF HISTONE DEACETYLASE INHIBITORS AND IMMUNOMODULATORY DRUGS

RELATED APPLICATIONS

This application is a 35 U.S.C. § 371 filing of International Application No. PCT/US17/18445, filed Feb. 17, 2017 which application claims priority to U.S. Provisional Patent Application No. 62/296,366 filed Feb. 17, 2016, which is incorporated by reference in its entirety.

BACKGROUND

Histone deacetylase (HDAC) enzymes represent attractive therapeutic targets in cancers, including multiple myeloma and lymphoma, and other conditions having abnormal cell proliferation, but unfortunately non-selective HDAC inhibitors have led to dose-limiting toxicities in patients (see, for example, a discussion of the use of inhibitors of histone deacetylases for the treatment of cancer: Marks et al. Nature Reviews Cancer 2001, 7,194; Johnstone et al. Nature Reviews Drug Discovery 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al Curr. Opin. Chem. Biol. 1997, 1, 300-308). HDACs participate in cellular pathways that control cell shape and differentiation, and an HDAC inhibitor has been shown effective in treating an otherwise recalcitrant cancer (Warrell et al J. Natl. Cancer Inst. 1998, 90, 1621-1625). Eleven human HDACs that use Zn as a cofactor have been identified (Taunton et al. Science 1996, 272, 408-411; Yang et al. J. Biol. Chem. 1997, 272, 28001-28007. Grozinger et al. Proc. Natl. Acad. Sci. U.S.A. 1999, 96, 4868-4873; Kao et al. Genes Dev. 2000, 14, 55-66. Hu et al J. Biol. Chem. 2000, 275, 15254-15264; Zhou et al. Proc. Natl. Acad. Sci. U.S.A. 2001, 98, 10572-10577; Venter et al. Science 2001, 291, 1304-1351), and these members fall into three HDAC classes (class I, II, and IV). An additional seven HDACs have been identified which use NAD as a cofactor.

The immunomodulatory (IMiD) class of drugs, including lenalidomide and pomalidomide, exhibit striking anti-myeloma properties in a variety of multiple myeloma models, and have demonstrated significant clinical activity in multiple myeloma patients. IMiDs also have applications in other cancers, including leukemia, lymphoma, prostate cancer, and renal cell carcinoma.

Due to the dose-limiting toxicities of non-selective HDAC inhibitors, there is an ongoing need in the art for more efficacious and less toxic compositions and methods for the treatment of cancer, including multiple myeloma and lymphoma.

SUMMARY OF THE INVENTION

Provided herein are methods of using pharmaceutical combinations for increasing (or decreasing) the expression of interferon regulated genes in a cancer cell. Also provided are methods for treating cancers, lymphocyte proliferation disorders, and pathogen infected cells in a subject in need thereof.

In a first aspect, methods for increasing the expression of interferon-regulated genes in cancer cells comprising co-administering a therapeutically effective amount of an HDAC inhibitor and an IMiD to a subject in need thereof are provided herein. In this aspect, the co-administration of the HDAC inhibitor and the IMiD results in a synergistic increase in the expression of genes regulated by interferon in the cancer cells. The interferon can be interferon-$\alpha$, interferon-$\beta$, or interferon-$\gamma$. The cancer cells can be blood cells, such as white blood cells. The white blood cells can be myeloid cells or B lymphocytes. The cancer cells can be multiple myeloma cells, diffuse large B-cell lymphoma cells, indolent lymphoma cells, follicular lymphoma cells, chronic lymphocytic leukemia cells, or mantle cell lymphoma cells. In the case of multiple myeloma, the multiple myeloma can be a relapsed or refractory multiple myeloma. In these methods, the promoters and/or enhancer regions of the interferon-regulated genes may comprise an IKZF1, IKZF3, or STAT1 binding site. The promoters and/or enhancer regions of the interferon-regulated genes can comprise an HDAC1 or HDAC2 or HDAC3 binding site. In these methods, it is hypothesized that the co-administration of the HDAC inhibitor and the IMiD may enhance the recognition of the cancer cells by the subject's immune system; this increased recognition of cancer cells by the immune system can comprise increased migration of T cells to the cancer cells. The methods also include that co-administration of the HDAC inhibitor and the IMiD increases the expression of one or more major histocompatibility complex (HLA) genes; this increase in histocompatibility complex gene expression can enhance antigen presentation by antigen-presenting cells. In the disclosed methods, the co-administration of the HDAC inhibitor and the IMiD can result in a synergistic increase in the expression and secretion of CCL4 protein in the cancer cells. Also in the disclosed methods, the co-administration of the HDAC inhibitor and the IMiD enhances apoptosis of the cancer cells; such co-administration of the HDAC inhibitor and the IMiD increases the expression of XIAP-associated factor 1 (XAF1) or caspase-1 (CASP1) genes in the apoptotic cancer cells; furthermore, the co-administration of the HDAC inhibitor and the IMiD acts in synergy with a chemotherapeutic agent or immunotherapeutic composition to increase the apoptosis of the cancer cells. In this aspect, the increase in the expression of interferon-regulated genes can comprise a synergistic increase in caspase-1 (CASP1) gene expression in the cancer cells. In the disclosed methods, the increase in the expression of interferon-regulated genes can increase infiltration of immune cells into a tumor formed by the cancer cells.

In a second aspect, methods of treating a lymphocyte proliferation disorder comprising co-administering a therapeutically effective amount of an HDAC inhibitor and an IMiD to a subject in need thereof, wherein the co-administration treats the lymphocyte proliferative disorder are provided. In an embodiment, the co-administration increases the expression of interferon-regulated genes. In this aspect, the lymphocyte proliferative disorder can be myelodysplastic syndrome (MDS), wherein the myelodysplastic syndrome can be acute myeloid leukemia (AML).

In any of the preceding aspects, the interferon-regulated genes can comprise at least one gene selected from the group consisting of a C-C motif chemokine 4 (CCL4; MIP-1(3), caspase-1 (CASP1), interferon $\alpha$-inducible protein 27 (IFI27), an interferon-induced protein with tetratricopeptide repeats 1 (IFIT 1), an interferon-induced protein with tetratricopeptide repeats 3 (IFIT3), a poly (ADP-ribose) polymerase family, member 14 (PARP 14) and XIAP-associated factor 1 (XAF1).

In a third aspect, methods of treating infection by a pathogen comprising co-administering a therapeutically effective amount of an HDAC inhibitor and an IMiD to a subject in need thereof, wherein the infection is treated, are provided.

In a fourth aspect, disclosed herein are methods of inhibiting or reducing the expression of BIRCS (survivin) and c-myc regulated genes in cancer cells comprising co-administering a therapeutically effective amount of an HDAC inhibitor and an IMiD to a subject in need thereof. The co-administration of the HDAC inhibitor and the IMiD can result in a synergistic reduction in the expression of c-myc regulated genes in the cancer cells.

In any of the preceding aspects, the HDAC inhibitor is an HDAC6 selective inhibitor. The HDAC6 selective inhibitor can be a compound of Formula I:

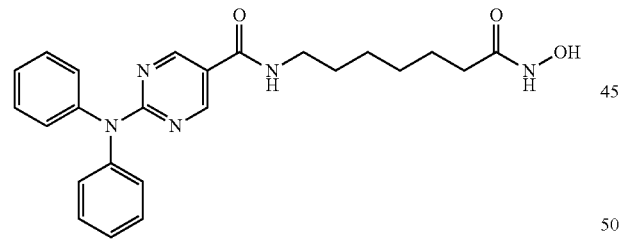

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl. In such case, the compound of Formula I can be:

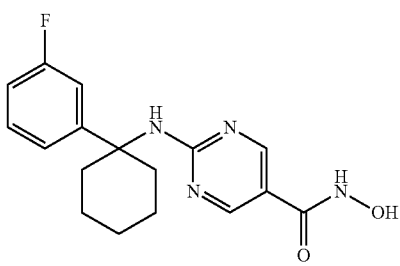 [SMILES: O=C(NO)c1cnc(NC2(c3cccc(F)c3)CCCCC2)nc1]

or a pharmaceutically acceptable salt thereof.
Or, the compound of Formula I can be:

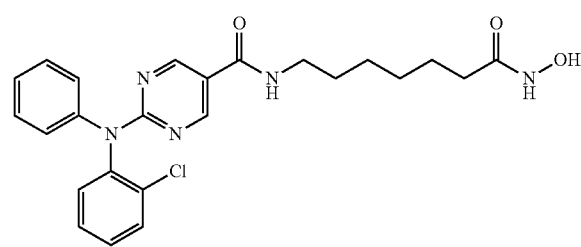 [SMILES: O=C(CCCCCCNC(=O)c1cnc(N(c2ccccc2)c2ccccc2Cl)nc1)NO]

or a pharmaceutically acceptable salt thereof.

The methods also disclose that the HDAC6-selective inhibitor can be a compound of Formula II:

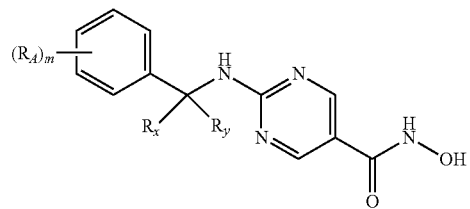

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, cyclooctyl;
each $R_A$ is independently $C_{1-6}$-alkyl, $C_{1-6}$-alkoxy, halo, OH, —$NO_2$, —CN, or —$NH_2$; and m is 0 or 1.

In such cases, the compound of Formula II can be:

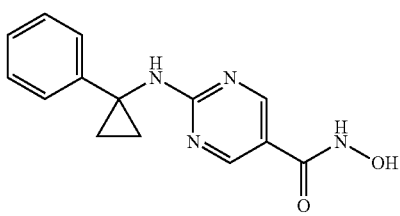

or a pharmaceutically acceptable salt thereof.
Or, the compound of Formula II can be:

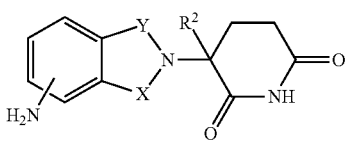

or a pharmaceutically acceptable salt thereof.

In any of the preceding aspects, the IMiD can be a compound of Formula III:

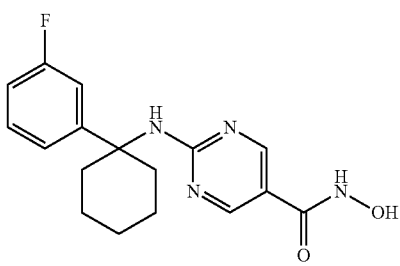 [SMILES: O=C(NO)c1cnc(NC2(c3cccc(F)c3)CCCCC2)nc1]

(III)

or a pharmaceutically acceptable salt thereof,
wherein,
one of X and Y is C=O, the other of X and Y is $CH_2$ or C=O; and
$R^2$ is H or $C_{1-6}$-alkyl.

In an embodiment, the compound of Formula III is:

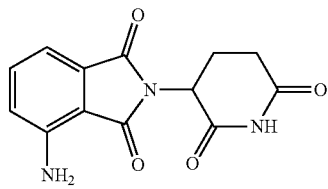

or a pharmaceutically acceptable salt thereof.

In another embodiment, the compound of Formula III is:

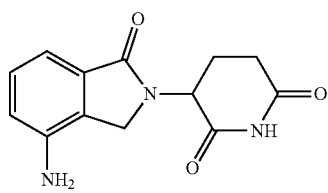

or a pharmaceutically acceptable salt thereof

Also in any of the preceding aspects, the HDAC inhibitor increases interferon-regulated gene expression when administered alone, and wherein the IMiD increases interferon-regulated gene expression when administered alone. In such instance, the increase in the expression of the interferon-regulated genes is greater when both the HDAC inhibitor and the IMiD are administered together than when either of the HDAC inhibitor or the IMiD is administered alone. Also in any of the preceding aspects, the increase in the expression of the interferon-regulated genes is dependent on the dose of the co-administered HDAC inhibitor and IMiD.

BRIEF DESCRIPTION OF THE FIGURES

FIGS. 1A-C show the $F_A$/CI Synergy Plots after treatment of MM.1s cells with an HDAC6 inhibitor and an IMiD. FIG. 1A shows the $F_A$/CI Synergy Plots after treatment of MM.1s cells with Compound A, and either lenalidomide (top) or pomalidomide (bottom). FIG. 1B shows the $F_A$/CI Synergy Plots after treatment of MM.1s cells with Compound B, and either lenalidomide (top) or pomalidomide (bottom). FIG. 1C shows the $F_A$/CI Synergy Plots after treatment of MM.1s cells with Compound C, and either lenalidomide (top) or pomalidomide (bottom). Data points with CI values <1 indicate treatment combinations resulting in synergistic decreases in cellular viability.

FIGS. 2A-C show the $F_A$/CI Synergy Plots after treatment of H929 cells with an HDAC6 inhibitor and an IMiD. FIG. 2A shows the $F_A$/CI Synergy Plots after treatment of H929 cells with Compound A, and either lenalidomide (top) or pomalidomide (bottom). FIG. 2B shows the $F_A$/CI Synergy Plots after treatment of H929 cells with Compound B, and either lenalidomide (top) or pomalidomide (bottom). FIG. 2C shows the $F_A$/CI Synergy Plots after treatment of H929 cells with Compound C, and either lenalidomide (top) or pomalidomide (bottom). Data points with CI values <1 indicate treatment combinations resulting in synergistic decreases in cellular viability.

FIG. 3A is a graph that shows apoptosis in H929 cells with Compound A and lenalidomide. FIG. 3B is a graph that shows apoptosis in H929 cells with Compound A and pomalidomide.

FIGS. 5A-D are sets of $F_A$/CI Synergy Plots showing that the combination of HDAC6 inhibitors and IMiDs results in synergistic decreases in myeloma cell growth and viability. FIG. 5A is a set of graphs that show the results of experiments in which H929 myeloma cells were exposed to increasing doses of Compound A in combination with lenalidomide (top panel) or pomalidomide (bottom panel) at constant ratios. FIG. 5B is a set of graphs that show the results of experiments in which H929 myeloma cells were exposed to increasing doses of Compound C in combination with lenalidomide (top panel) or pomalidomide (bottom panel) at constant ratios. FIG. 5C is a set of graphs that show the results of experiments in which MM.1s myeloma cells were exposed to increasing doses of Compound A in combination with lenalidomide (top panel) or pomalidomide (bottom panel) at constant ratios. FIG. 5D is a set of graphs that show the results of experiments in which MM.1s myeloma cells were exposed to increasing doses of Compound C in combination with lenalidomide (top panel) or pomalidomide (bottom panel) at constant ratios. FIGS. 5E-F are sets of graphs showing that the combination of HDAC6 inhibitors and IMiDs resulted in synergistic decreases in myeloma cell growth and viability. FIG. 5E shows the results of experiments in which H929 myeloma cells were exposed to increasing doses of Compound B in combination with lenalidomide (top panel) or pomalidomide (bottom panel) at constant ratios. FIG. 5F shows the results of experiments in which MM.1s myeloma cells were exposed to increasing doses of Compound B in combination with lenalidomide (top panel) or pomalidomide (bottom panel) at constant ratios. The combination index (CI) values for each dose combination are shown (Actual), as well as a simulation of CI values across the entire dosing range. Data points with CI values <1 indicate treatment combinations resulting in synergistic decreases in cellular viability.

FIG. 6A is a graph showing the effects of treatment of H929 myeloma cells for 3 days with DMSO, Compound A (2 µM), lenalidomide (2 µM), pomalidomide (1 µM), or combinations of Compound A with either IMiD on cell cycle inhibition. FIG. 6B is a graph showing the effects of treatment of H929 myeloma cells for 5 days with DMSO, Compound A (2 µM), lenalidomide (2 µM), pomalidomide (1 µM), or combinations of Compound A with either IMiD on cell cycle inhibition. FIG. 6C is a graph showing the effects of treatment of MM.1s myeloma cells for 3 days with DMSO, Compound A (2 µM), lenalidomide (2 µM), pomalidomide (1 µM), or combinations of Compound A with either IMiD on cell cycle inhibition. FIG. 6D is a graph showing the effects of treatment of MM.1s myeloma cells for 5 days with DMSO, Compound A (2 lenalidomide (2 µM), pomalidomide (1 µM), or combinations of Compound A with either IMiD on cell cycle inhibition.

FIG. 6E shows the effect of treatment of H929 myeloma cells for 4 days with DMSO, Compound B (2 µM), lenalidomide (2 µM), pomalidomide (1 µM), or combinations of Compound B with either IMiD on cell cycle inhibition. FIG. 6F show the effects of treatment of MM.1s myeloma cells for 5 days with DMSO, Compound B (2 µM), lenalidomide (2 µM), pomalidomide (1 µM), or combinations of Compound B with either IMiD on cell cycle inhibition.

FIG. 7A is a graph showing the effects of treatment of H929 myeloma cells for 5 days with DMSO, Compound A (2 µM), lenalidomide (2 µM), pomalidomide (1 µM), or combinations of Compound A with either IMiD on the induction of apoptosis. FIG. 7B is a graph showing the effects of treatment of H929 myeloma cells for 7 days with DMSO, Compound A (2 µM), lenalidomide (2 µM), pomalidomide (1 µM), or combinations of Compound A with either IMiD on the induction of apoptosis. FIG. 7C is a graph showing the effects of treatment of MM.1s myeloma cells for 5 days with DMSO, Compound A (2 µM), lenalidomide (2 µM), pomalidomide (1 µM), or combinations of Compound A with either IMiD on the induction of apoptosis. FIG. 7D is a graph showing the effects of treatment of MM.1s myeloma cells for 7 days with DMSO, Compound A (2 µM), lenalidomide (2 µM), pomalidomide (1 µM), or combinations of Compound A with either IMiD on the induction of apoptosis.

FIG. 7E shows the effect of treatment of H929 myeloma cells for 4 days with DMSO, Compound B (2 µM), lenalidomide (2 µM), pomalidomide (1 µM), or combinations of Compound B with either IMiD on the induction of apoptosis. FIG. 7F shows the effect of treatment of MM. 1 s myeloma cells for 5 days with DMSO, Compound B (2 µM), lenalidomide (2 µM), pomalidomide (1 µM), or combinations of Compound B with either IMiD on the induction of apoptosis.

FIG. 8A is a graph showing the effects of treatment of H929 myeloma cells with DMSO, Compound A (2 µM), lenalidomide (1 µM), pomalidomide (1 µM), or combinations of Compound A with either IMiD on the expression of MYC. FIG. 8B is a graph showing the effects of treatment of H929 myeloma cells with DMSO, Compound A (2 µM), lenalidomide (1 µM), pomalidomide (1 µM), or combinations of Compound A with either IMiD on the expression of IRF4. FIG. 8C is a graph showing the effects of treatment of H929 myeloma cells with DMSO, Compound A (2 µM), lenalidomide (1 µM), pomalidomide (1 µM), or combinations of Compound A with either IMiD on the expression of P21.

FIG. 8D is an immunoblot confirming, at the protein level in H929 cells after 48 hours of combination treatment, the reduction of MYC and IRF4 and the increase of P21 expression relative to any of the single agents.

FIG. 8E is an image of an immunoblot confirming, at the protein level in H929 cells, the reduction of IRF4 after 48 hours of combination treatment with Compound B and either lenalidomide or pomalidomide relative to any of the single agents.

FIG. 11 shows a table of the gene sets that are positively enriched (top) and negatively enriched (bottom) when multiple myeloma cells are treated with Compound A at 4 µM in combination with pomalidomide (1 µM) at 48 hours when compared to treating the cells with Compound A alone or with pomalidomide alone. Gene sets representing an interferon response are the only positively enriched sets found in comparisons of combination treatment relative to both Compound A or pomalidomide single agent treatments. Gene sets representing c-myc targets are the only negatively enriched sets found in comparisons of combination treatment relative to both Compound A or pomalidomide single agent treatments. For each pairwise comparison, robust and statistically significant positive enrichment was identified for the gene sets 'Interferon Gamma Response' and 'Interferon Alpha Response'. Red boxes highlight the inclusion of the interferon response pathways in each combination versus single agent comparison. Robust and statistically significant negative enrichment was also identified for the gene sets 'MYC targets V2'. Blue boxes highlight the inclusion of the MYC target genes pathway in each combination versus single agent comparison. Combo=combination; Pom=Pomalidomide.

FIGS. 12A-B are graphs showing the results of Gene Set Enrichment Analysis (GSEA) that showed that interferon regulated ("Interferon Response") genes are positively enriched when cells are treated with the combination of Compound A (at 4 µM) and pomalidomide (1 µM) at 48 hours compared to cells treated only with Compound A (FIG. 12A), or pomalidomide alone (FIG. 12B). Significant enrichment is illustrated by the positive running enrichment score (ES) marked by the green line, positive normalized enrichment score (NES), and false discovery rate (FDR) P-value<0.001.

FIGS. 12C-D are graphs showing that myc target genes are negatively enriched, as shown by GSEA, when cells are treated with the combination of Compound A (at 4 µM) and pomalidomide (1 µM) at 48 hours compared to cells treated only with Compound A (FIG. 12C), or pomalidomide (FIG. 12D) alone. Significant enrichment is illustrated by the negative running enrichment score (ES) marked by the green line, negative normalized enrichment score (NES), and false discovery rate (FDR) P-value<0.001.

FIGS. 12E-F are graphs showing that interferon regulated ("Interferon Response") genes are positively enriched, as shown by GSEA, when multiple myeloma cells are treated with pomalidomide (1 µM) when compared to cells treated with vehicle only (dimethyl sulfoxide, "DMSO") after 48 hours (FIG. 12E) and when Compound A (4 µM) treated cells are compared to vehicle treated cells after 48 hours (FIG. 12F). Similarly, FIGS. 12G-H are graphs that show that myc target genes are negatively enriched, as shown by GSEA, when multiple myeloma cells are treated with pomalidomide (1 µM) when compared to cells treated with vehicle only (dimethyl sulfoxide, "DMSO") after 48 hours (FIG. 12G) and when Compound A (4 µM) treated cells are compared to vehicle treated cells after 48 hours (FIG. 12H). See Example 16 for further details.

FIGS. 13A-F show the results of a dose and time dependence analysis on the Interferon Alpha Response gene set. FIGS. 13A-C show the analysis of comparing treatment with the combination of Compound A and pomalidomide (1 µM), with increasing amounts of Compound A (2 µM (FIG. 13A), 3 µM (FIG. 13B), and 4 µM (FIG. 13C)) at 24 hours when interferon regulated genes are analyzed compared to cells treated with pomalidomide (1 µM) alone. FIGS. 13D-F shows the results for these same agent treatments, but at 48 hours instead of 24 hours.

FIGS. 14A-F show the results of a dose and time dependence analysis on the MYC Targets V2 gene set. FIGS. 14A-C show the analysis of comparing treatment with the combination of Compound A and pomalidomide (1 µM), with increasing amounts of Compound A (2 µM (FIG. 14A), 3 µM (FIG. 14B), and 4 µM (FIG. 14C)) at 24 hours when c-myc target genes are analyzed when compared to pomalidomide (1 µM) treated cells. FIGS. 14D-F shows the results for these same agent treatments, but at 48 hours instead of 24 hours.

FIG. 16A shows the results for the XAF1 gene; FIG. 16B shows the results for the CCL4 gene; FIG. 16C shows the results for the CASP1 gene; and FIG. 16D shows the results for the BIRC5 gene.

DETAILED DESCRIPTION

Figure 2B:
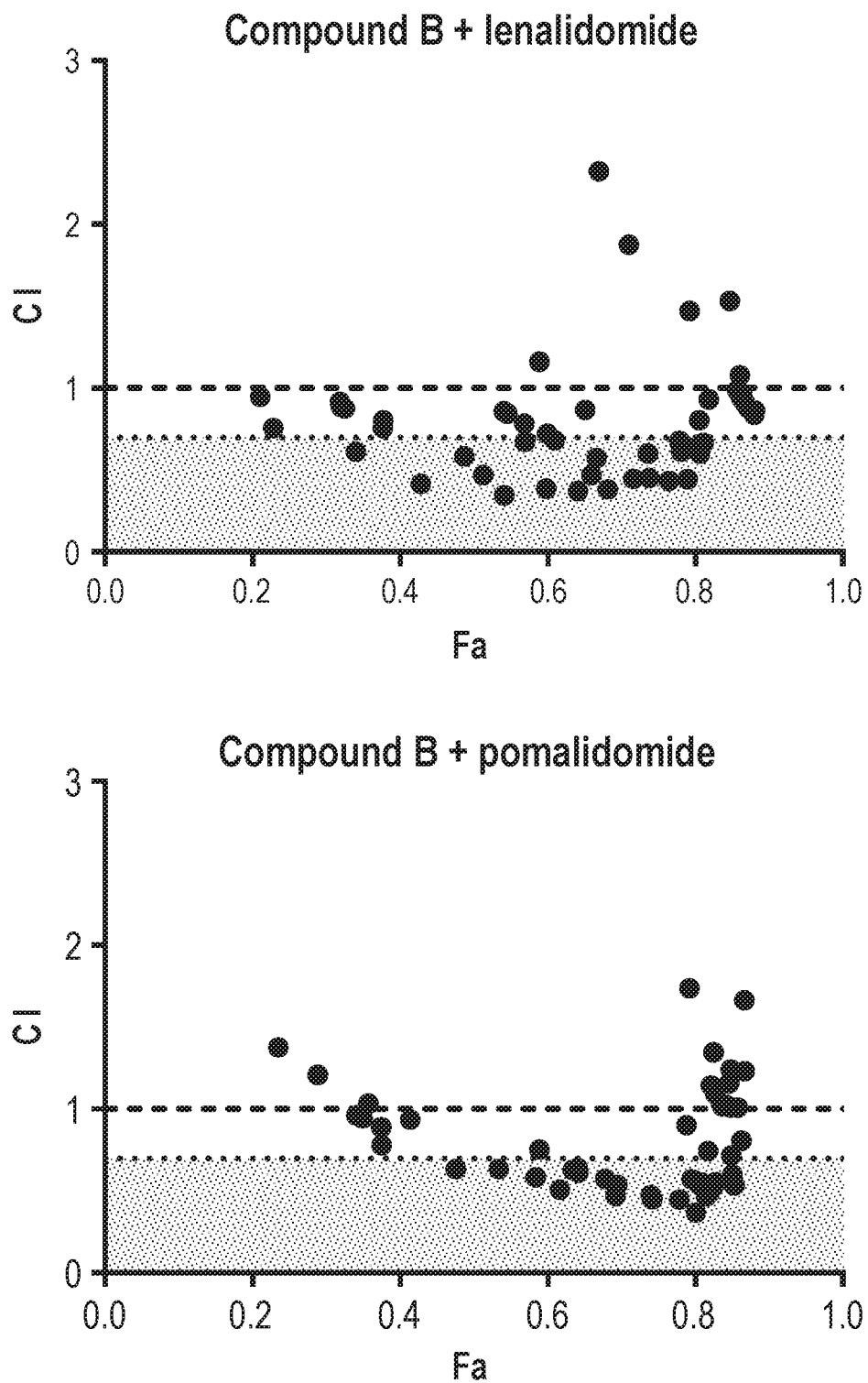

The instant application is directed, generally, to methods of using combinations comprising an HDAC inhibitor and an IMiD to increase expression of interferon regulated, or responsive, genes.

Definitions

Listed below are definitions of various terms. These definitions apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$ alkyl moieties include, but are not limited to, methyl, ethyl, propyl, isopropyl, n-butyl, tent-butyl, neopentyl, n-hexyl moieties; and examples of $C_{1-8}$ alkyl moieties include, but are not limited to, methyl, ethyl, propyl, isopropyl, n-butyl, tent-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl and the like. In some embodiments, aryl groups have 6 carbon atoms. In some embodiments, aryl groups have from six to ten carbon atoms. In some embodiments, aryl groups have from six to sixteen carbon atoms.

The term "combination" refers to two or more therapeutic agents to treat a therapeutic condition or disorder described in the present disclosure. Such combination or co-administration of therapeutic agents may be in the form of a single pill, capsule, or intravenous solution. However, the term "combination," as well as "co-administration" or "co-administering," also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hdal gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

An "HDAC inhibitor" means a compound that selectively or non-selectively inhibits at least one function of one or more HDACs, such as HDAC1, HDAC2, HDAC3, and HDAC6 etc.

The term "HDAC6-selective" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6-selective. On the other hand, a compound that binds to HDAC6 with an $IC_{50}$ of 50 nM and to HDAC1 with an $IC_{50}$ of 60 nM is not HDAC6-selective.

The term "inhibitor" is synonymous with the term antagonist.

HDAC Inhibitors

Provided herein are methods of increasing the expression of interferon-regulated genes in cancer cells comprising co-administering a therapeutically effective amount of an HDAC inhibitor and an IMiD to a subject in need thereof. Such methods can be used to synergistically increase the expression of interferon-regulated genes by co-administering the HDAC inhibitor and IMiD, compared to using either the HDAC inhibitor or IMiD alone. The methods can be used to treat cancer, including multiple myeloma, such as a relapsed or refractory multiple myeloma, in a subject. Also provided are methods for treating pathogen infection or lymphocyte proliferation disorders in a subject in need thereof.

The disclosed methods comprise the use of an HDAC inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6-selective inhibitor.

In some embodiments, the HDAC6-selective inhibitor is a compound of Formula I:

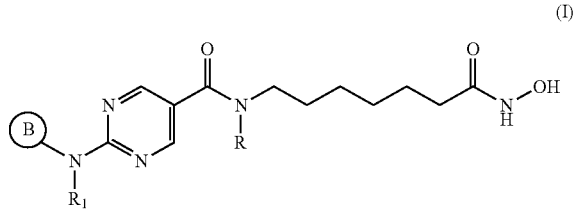

(I)

or a pharmaceutically acceptable salt thereof, wherein, ring B is aryl or heteroaryl;

$R_1$ is an aryl or heteroaryl, each of which may be optionally substituted by OH, halo, or $C_{1-6}$-alkyl; and R is H or $C_{1-6}$-alkyl.

Representative compounds of Formula I include, but are not limited to:

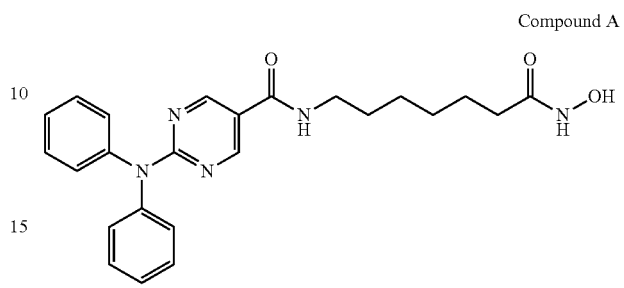

Compound A 2-(diphenylamino)-N-(7-(hydroxyamino)-7-oxoheptyl)pyrimidine-5-carboxamide
$IC_{50}$(nM) HDAC6 = 10 HDAC3 = 84

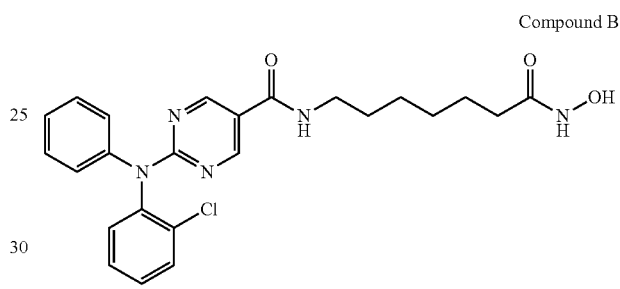

Compound B 2-((2-chlorophenyl)(phenyl)amino)-N-(7-(hydroxyamino)-7-oxoheptyl)pyrimidine-5-carboxamide
$IC_{50}$(nM) HDAC6 = 4 HDAC3 = 76 or pharmaceutically acceptable salts thereof.

The preparation and properties of HDAC6-selective inhibitors according to Formula I are provided in International Patent Application No. PCT/US2011/021982, the entire contents of which are incorporated herein by reference.

In other embodiments, the HDAC6-selective inhibitor is a compound of Formula II:

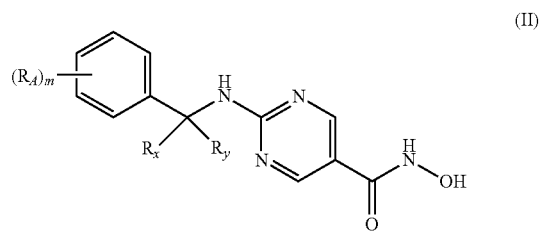

(II)

or a pharmaceutically acceptable salt thereof, wherein, $R_x$ and $R_y$, together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2.

Representative compounds of Formula II include, but are not limited to:

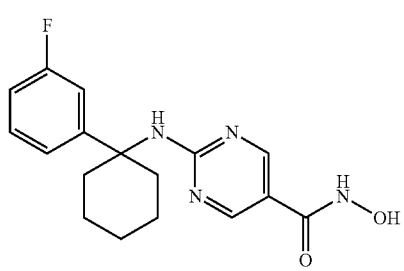

Compound C

IC$_{50}$(nM) HDAC6 = 7 HDAC1 = 2123
(283.5x) HDAC2 = 2570 (9343.2x)
HDAC = 11223 (1498.8x)

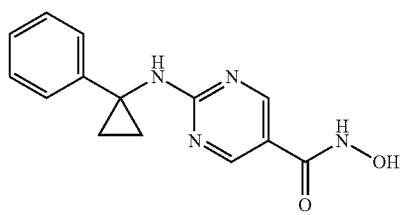 [SMILES: O=C(NO)c1cnc(NC2(c3ccccc3)CC2)nc1]

Compound D

IC$_{50}$(nM) HDAC6 = 2 HDAC1 = 94 (60x)
HDAC2 = 128 (81.9x) HDAC3 = 219 (139.5x)

or pharmaceutically acceptable salts thereof.

The preparation and properties of HDAC6-selective inhibitors according to Formula II are provided in International Patent Application No. PCT/US2011/060791, the entire contents of which are incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Immunomodulatory Drugs (IMiDs)

The disclosed methods comprise using an immunomodulatory drug (also referred to herein as "IMiD"). The IMiD may be any IMiD. Preferably, the IMiD is a compound of Formula III.

In some embodiments, the IMiD is a compound of Formula III

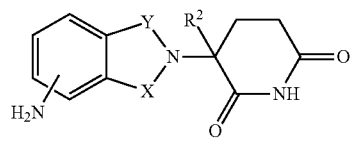

(III)

or a pharmaceutically acceptable salt thereof,
wherein,
one of X and Y is C=O, the other of X and Y is CH$_2$ or C=O; and
R$^2$ is H or C$_{1-6}$-alkyl.

Representative compounds of Formula III include, but are not limited to:

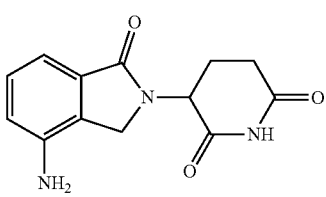

Compound E

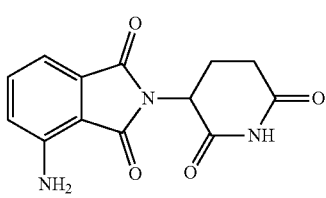 [SMILES: Nc1cccc2c1C(=O)N(C1CCC(=O)NC1=O)C2=O]

Compound F or pharmaceutically acceptable salts thereof.

The preparation and properties of the IMiDs according to Formula III are provided in U.S. Pat. Nos. 5,635,517; 6,281,230; 6,335,349; and 6,476,052; as well as International Patent Application No. PCT/US97/013375, each of which is incorporated herein by reference in its entirety.

In some embodiments, the described compounds are unsolvated. In other embodiments, one or more of the compounds are in solvated form. As known in the art, the solvate can be any of pharmaceutically acceptable solvent, such as water, ethanol, and the like.

Combinations/Pharmaceutical Combinations

Provided herein are methods of using combinations for increasing the expression of interferon regulated genes in a subject in need thereof, such as a subject suffering from cancer, such as multiple myeloma. Provided in some embodiments are methods comprising an HDAC inhibitor and an IIVILiD for increasing the expression of interferon regulated genes in a cancer cell in a subject in need thereof. In other embodiments, the combination can be used to treat lymphocyte proliferation disorder or a pathogen-infected cell.

In some embodiments of the methods, the HDAC inhibitor is an HDAC6-selective inhibitor. In specific embodiments, the HDAC6-selective inhibitor is a compound of Formula I:

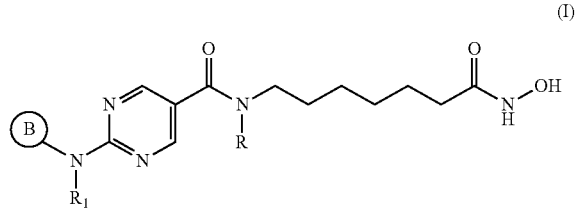

(I)

or a pharmaceutically acceptable salt thereof.

In preferred embodiments, the compound of Formula I is:

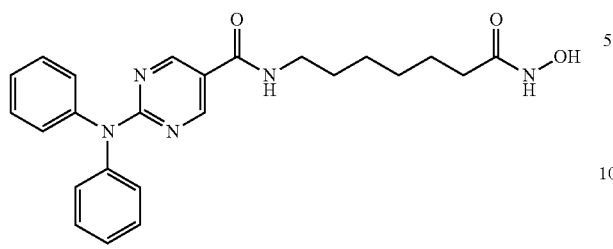

or a pharmaceutically acceptable salt thereof.

In yet other embodiments, the compound of Formula I is:

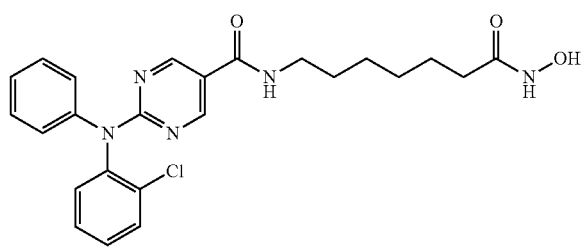 [SMILES: O=C(CCCCCCNC(=O)c1cnc(N(c2ccccc2)c2ccccc2Cl)nc1)NO]

or a pharmaceutically acceptable salt thereof.

In other specific embodiments, the HDAC6-selective inhibitor is a compound of Formula II:

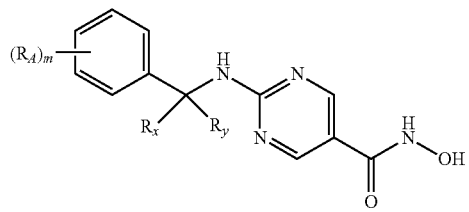

(II)

or a pharmaceutically acceptable salt thereof.

In preferred embodiments, the compound of Formula II is:

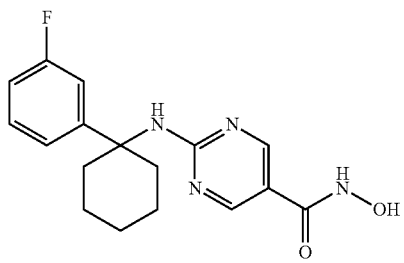 [SMILES: O=C(NO)c1cnc(NC2(c3cccc(F)c3)CCCCC2)nc1]

or a pharmaceutically acceptable salt thereof.

In other preferred embodiments, the compound of Formula II is:

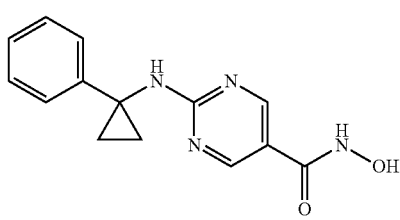 [SMILES: O=C(NO)c1cnc(NC2(c3ccccc3)CC2)nc1]

or a pharmaceutically acceptable salt thereof.

In some embodiments of the method, the IMiD is a compound of Formula III:

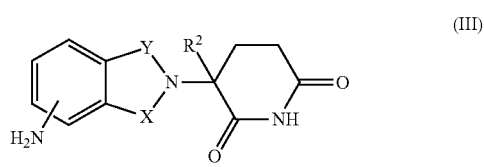

(III)

or a pharmaceutically acceptable salt thereof.

In preferred embodiments, the compound of Formula III is:

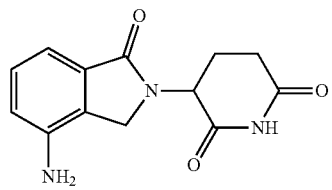 [SMILES: Nc1cccc2c1CN(C1CCC(=O)NC1=O)C2=O]

or a pharmaceutically acceptable salt thereof.

In yet other preferred embodiments, the compound of Formula III is:

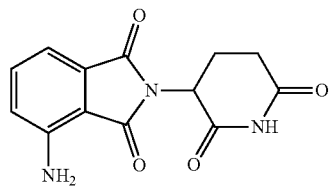 [SMILES: Nc1cccc2c1C(=O)N(C1CCC(=O)NC1=O)C2=O]

or a pharmaceutically acceptable salt thereof.

In one embodiment, provided herein is method comprising administering an HDAC6-selective inhibitor and an IMiD, wherein the HDAC6-selective inhibitor is a compound of Formula I:

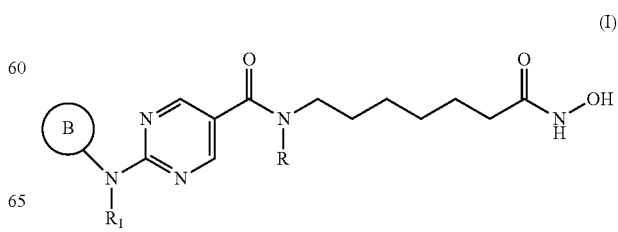

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl; and
the IMiD is a compound of Formula III:

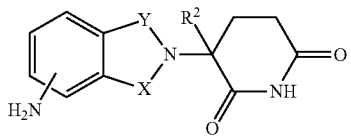

(III)

or a pharmaceutically acceptable salt thereof,
wherein,
one of X and Y is C=O, the other of X and Y is $CH_2$ or C=O; and
$R^2$ is H or $C_{1-6}$-alkyl.

As described in further detail below, some embodiments of this method include an anti-inflammatory agent, while other embodiments of this method do not include dexamethasone.

In specific embodiments of the method, the HDAC6-selective inhibitor is:

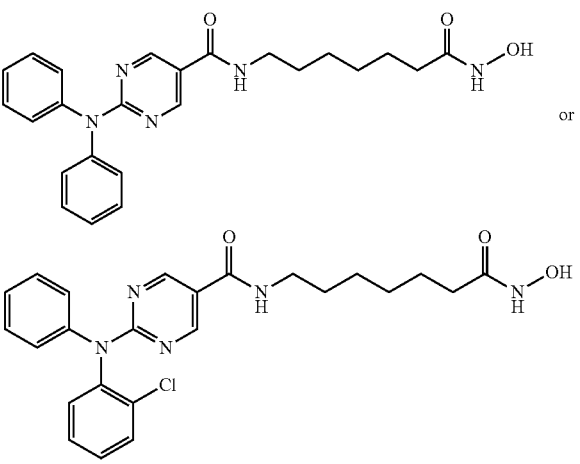

or or pharmaceutically acceptable salts thereof; and
the IMiD is:

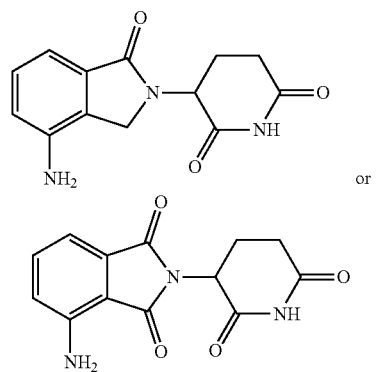

or or a pharmaceutically acceptable salt thereof.

In another embodiment, provided herein are methods comprising administering an HDAC6-selective inhibitor and an IMiD, wherein the HDAC6-selective inhibitor is a compound of Formula II:

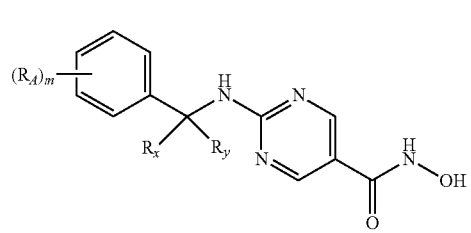

(II)

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2; and
the IMiD is a compound of Formula III.

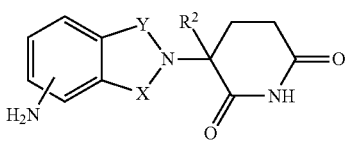

(III)

or a pharmaceutically acceptable salt thereof,
wherein,
one of X and Y is C=O, the other of X and Y is $CH_2$ or C=O; and
$R^2$ is H or $C_{1-6}$-alkyl.

In specific embodiments of the method, the HDAC6-selective inhibitor is:

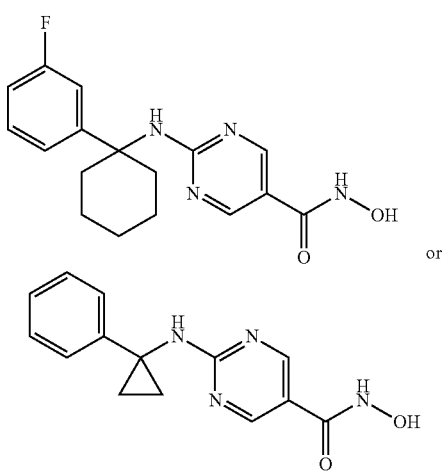

or or a pharmaceutically acceptable salt thereof; and the IMiD is:

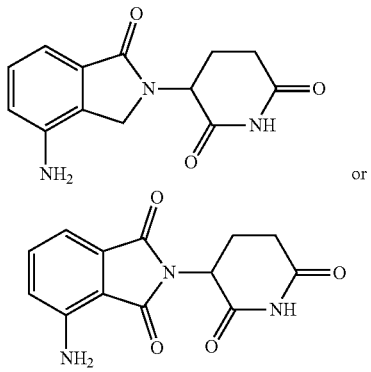

or a pharmaceutically acceptable salt thereof.

Although the compounds of Formulas I, II, and III are depicted in their neutral forms, in some embodiments, these compounds are used in a pharmaceutically acceptable salt form. "Pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts of the parent compound formed, for example, from non-toxic inorganic or organic acids. Pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Administration/Dose

In some embodiments, the HDAC inhibitor (e.g., a compound of Formula I or II) is administered simultaneously with the IMiD (e.g., a compound of Formula III). Simultaneous administration typically means that both compounds enter the patient at precisely the same time. However, simultaneous administration also includes the possibility that the HDAC inhibitor and the IMiD enter the patient at different times, but the difference in time is sufficiently miniscule that the first administered compound is not provided the time to take effect on the patient before entry of the second administered compound. Such delayed times typically correspond to less than five minutes or less than two minutes, and more typically, less than one minute. In one example, wherein the compounds are in solution, simultaneous administration can be achieved by administering a solution containing the combination of compounds. In another example, simultaneous administration of separate solutions, one of which contains the HDAC inhibitor and the other of which contains the IMiD, can be used. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising the IMiD.

In other embodiments, the HDAC inhibitor and the IMiD are not administered simultaneously. In some embodiments, the HDAC inhibitor is administered before the IMiD. In other embodiments, the IMiD is administered before the HDAC inhibitor. The time difference in non-simultaneous administrations can be less than 1 minute, 5 minutes, 10 minutes, 15 minutes, 30 minutes, 45 minutes, 60 minutes, 2 hours, 3 hours, 6 hours, 9 hours, 12 hours, 24 hours, 36 hours, or 48 hours. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and IMiD are administered in a therapeutically effective amount or dosage. A "therapeutically effective amount" is an amount of HDAC inhibitor (such as a compound of Formula I or II) or an IMiD (such as a compound of Formula III) that, when administered to a patient by itself, effectively increases the expression of at least one interferon regulated gene in a cancer cell. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on, in the case of cancer, the type of cancer, stage of the cancer, the age of the patient being treated, and other facts. Similarly in the case of lymphocyte proliferation disorder, the amount of the compound that corresponds to a therapeutically effective amount strongly depends on, for example, the stage of the disorder. In the case of pathogen infection, the amount of the compound that corresponds to a therapeutically effective amount strongly depends on the degree of infection, the pathogen, and the type of cell(s) that is infected. In general, therapeutically effective amounts of these compounds are well-known in the art.

In other embodiments, one or both of the HDAC inhibitor and IMiD are administered in a sub-therapeutically effective amount or dosage. A sub-therapeutically effective amount is an amount of HDAC inhibitor (e.g., a compound of Formula I or II) or an IMiD (e.g., a compound of Formula III) that, when administered to a patient by itself, does not completely increase the expression of at least one interferon regulated gene in a cancer cell.

Whether administered in therapeutic or sub-therapeutic amounts, the combination of the HDAC inhibitor and the IMiD should be effective in treating, for example, cancer cells, such as cancer blood cells, including cancer white blood cells, such as myeloid cells or B lymphocytes. In some embodiments, the cancer cells are multiple myeloma cells, diffuse large B-cell lymphoma cells, indolent lymphoma cells, follicular lymphoma cells, chronic lymphocytic leukemia cells, or mantle cell lymphoma cells. In some embodiments, the multiple myeloma cells are relapsed or refractory multiple myeloma cells. For example, a sub-therapeutic amount of a compound of Formula III (IMiD) can be an effective amount if, when combined with an HDAC inhibitor compound (such as that of Formula I or II), the combination is effective in increasing the expression of at least one interferon regulated gene in a cancer cell, such that the targeted cancer is treated. The combination of HDAC inhibitor and the IMiD should be effective in treating, for example, lymphocyte proliferation disorder, as well as cellular pathogen infection.

In some embodiments, the use of the combination of compounds exhibits a synergistic effect (i.e., greater than additive effect) in increasing the expression of at least one interferon regulated gene in a cancer cell. In other embodiments, the use of the combination of compounds exhibits a synergistic effect (i.e., greater than additive effect) in decreasing the expression of c-MYC in a cancer cell. "Synergistic effect" refers to the action of two agents, such as, for example, an HDAC inhibitor and an IMiD, producing an effect, for example, slowing the symptomatic progression of cancer or symptoms thereof (or increasing the expression of at least one interferon regulated gene in a cancer cell), which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)), and the median-effect equation (Chou, T. C. and Talalay, P., Adv. Enzyme Regul. 22: 27-55 (1984)). Each equation referred to above can be applied to experimental data to generate a corresponding graph to aid in assessing the effects of using the drug combination. The corresponding graphs associated with the equations referred to above are the concentration-effect curve, isobologram curve and combination index curve, respectively.

In different embodiments, depending on the combination and the effective amounts used, the combination of compounds can inhibit cancer growth, achieve cancer stasis, or even achieve substantial or complete cancer regression. In other embodiments, depending on the combination and effective amounts used, the combination of compounds can decrease abnormal cell proliferation in lymphocyte proliferation disorders. In yet other embodiments, depending on the combination and effective amounts used, the combination of compounds can treat a cell infected by a pathogen.

While the use of amounts of an HDAC inhibitor and an IMiD should result in the effective increase of at least one interferon regulated gene in a cancer cell resulting in the effective treatment of cancer, such as multiple myeloma, or lymphocyte proliferation disorder, or a pathogen infected cell, the amounts, when combined, are preferably not excessively toxic to the patient (i.e., the amounts are preferably within toxicity limits as established by medical guidelines). In some embodiments, either to prevent excessive toxicity and/or provide a more efficacious treatment of the targeted cancer cells, a limitation on the total administered dosage is provided. Likewise, the use of amounts of an HDAC inhibitor and an IMiD should result in treating lymphocyte proliferation disorder (such as slowing or halting abnormal proliferation) or treating a pathogen-infected cell. Typically, the dosage amounts are per day; however, half-day and two-day or three-day cycles can also be used.

Exemplary dosages for IMiDs, such as the immunomodulatory compound or a pharmaceutically acceptable salt, solvate, stereoisomer, or prodrug thereof include about 0.001, 0.01, 0.1, 1, 2, 4, 5, 7.5, 10, 12.5, 15, 17.5, 20, 25, 50, 100, 150 or 200 mg. In some embodiments, lenalidomide is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of lenalidomide administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater. Pomalidomide is often administered in 1 mg, 2 mg, 3 mg, or 4 mg doses, although other doses, as indicated, may be used.

For HDAC inhibitors, dosages may range from about 5 mg/kg to about 100 mg/kg, about 1 µg/kg to about 500 mg/kg to about 1000 mg, can be administered, such as about 1 µg/kg, about 5 µg/kg, about 10 µg/kg, about 50 µg/kg, about 100 µg/kg, about 200 µg/kg, about 350 µg/kg, about 500 µg/kg, about 1 mg/kg, about 5 mg/kg, about 10 mg/kg, about 50 mg/kg, about 100 mg/kg, about 200 mg/kg, about 350 mg/kg, about 500 mg/kg, to about 1000 mg/kg or more per dose. HDAC inhibitors are often administered in 40 mg, 80 mg, 120 mg, 180 mg, 240 mg, 360 mg, or 480 mg doses, although other doses, as indicated, may be used.

When administered in combination, these dosages can be modified to account for enhanced or reduced activity of one drug in the presence of the other.

Different dosage regimens may be used in the disclosed methods. In some embodiments, a daily dosage is administered once, twice, three times, or four times a day for three, four, five, six, seven, eight, nine, or ten days. Depending on the stage and severity of the cancer in which at least one interferon regulated gene expression is to be increased, a shorter treatment time (e.g., up to five days) may be used along with a high dosage, or a longer treatment time (e.g., ten or more days, or weeks, or a month, or longer) may be used along with a low dosage. In some embodiments, a once- or twice-daily dosage is administered every other day.

In some embodiments, each dosage contains both an HDAC inhibitor and an IMiD to be delivered as a single dosage, while in other embodiments; each dosage contains either an HDAC inhibitor or an IMiD to be delivered as separate dosages.

Compounds of Formula I, II, or III, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and the IMiD of the pharmaceutical combination can be administered in a single unit dose or separate dosage forms. Accordingly, the phrase "pharmaceutical combination" includes a combination of two drugs in either a single dosage form or a separate dosage forms, i.e., the pharmaceutically acceptable carriers and excipients described throughout the application can be combined with an HDAC inhibitor and an IMiD in a single unit dose, as well as individually combined with an HDAC inhibitor and an IMiD when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or IMiDs described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions contains about 1% to about 99% by weight of the compounds described herein, or a pharmaceutically acceptable salt thereof, and 99% to 1% by weight of a pharmaceutically acceptable excipient. In one example, the composition is between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th ed. (Mack Publishing Company, Easton, Pa., 1990).

Methods

The disclosed methods of increasing the expression of at least one interferon regulated gene in a cancer cell by co-administering an effective amount of an HDAC inhibitor and an IMiD can be used to treat certain diseases, e.g., cancers or a pathogen infection. Furthermore, such co-administration of an effective amount of an HDAC inhibitor and an IMiD can be used to treat lymphocyte proliferation disorder, including myelodysplastic syndrome (MDS) and acute myeloid leukemia (AML). Co-administration of an effective amount of an HDAC inhibitor and IMiD can be used to treat a cell infected by a pathogen.

Increasing the expression of at least one interferon regulated gene in a cancer cell can comprise at least one gene selected from the group consisting of a C-C motif chemokine 4 (CCL4; MIP-1β), caspase-1 (CASP1), interferon a-inducible protein 27 (IFI27), an interferon-induced protein with tetratricopeptide repeats 1 (IFIT1), an interferon-induced protein with tetratricopeptide repeats 3 (IFIT3), a poly (ADP-ribose) polymerase family, member 14 (PARP 14) and XIAP-associated factor 1 (XAF1). In some embodiments, the increase of the expression of the interferon regulated genes is a synergistic increase.

The subject is typically a human. However, the subject can be any mammal for which treatment is desired. Thus, the disclosed methods can be applied to both human and veterinary applications.

The term "treating" or "treatment" as used herein comprises a treatment relieving, reducing or alleviating at least one symptom in a subject or affecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject, e.g., a mammal or human. The term "prevent," "preventing," or "prevention," as used herein comprises the prevention of at least one symptom associated with or caused by the state, disease or disorder being prevented. For example, the method can reduce the rate of cancer growth in a patient, or prevent the continued growth or spread of the cancer, or even reduce the overall reach of the cancer. In the case of lymphocyte proliferation disorder, abnormal cellular proliferation is at least reduced when the disclosed methods are applied; furthermore, abnormal cellular proliferation can be halted or prevented. In the case of pathogen infection, the damage from the pathogen is reduced and/or the presence of the pathogen is reduced.

In an embodiment, the cancer cells that are treated in a subject are blood cells, such as white blood cells (such as myeloid cells or B lymphocytes). The cancer cells can be multiple myeloma cells, diffuse large B-cell lymphoma cells, indolent lymphoma cells, follicular lymphoma cells, chronic lymphocytic leukemia cells, or mantle cell lymphoma cells. In the case of multiple myeloma cells, they can be relapsed or refractory multiple myeloma cells. In an embodiment, the co-administration of the HDAC inhibitor and the IMiD enhances the recognition of the cancer cells by the subject's immune system; such recognition can comprise, for example, increased migration of T cells to the cancer cells. The HDAC inhibitor can be an HDAC6-selective inhibitor. An example of an HDAC6-selective inhibitor that can be used is Compound A. An exemplary IMiD is Compound F. Other combinations may be used other than Compound A and Compound F, such as Compounds B, C, or D with Compound E.

In other embodiments, the co-administration of the HDAC inhibitor and the IMiD enhances apoptosis of the cancer cells. In such embodiments, increases in expression of interferon regulated genes comprises increase in the expression of XIAP-associated factor 1 (XAF1) or caspase-1 (CASP1) genes in the apoptotic cancer cells. A chemotherapeutic agent may also be administered, wherein the chemotherapeutic agent acts in synergy with the HDAC inhibitor and the IMiD to increase the apoptosis of the cancer cells. Furthermore, an immunotherapeutic may also be administered, such that there is synergy in activating the immune system; examples of suitable immunotherapeutic agents include anti-PD-1, anti-PD-L1, and anti-CTLA4 antibodies. Furthermore, other immunotherapeutic compositions may also be administered, such as cancer vaccines, adoptive cell therapies, including chimeric antigen receptor therapy (CAR-T). The HDAC inhibitor can be an HDAC6-selective inhibitor. An exemplary HDAC6-selective inhibitor is Compound A. An example of an IMiD that can be used is Compound F. Other combinations may be used other than Compound A and Compound F, such as Compounds B, C, or D with Compound E.

In an embodiment, in increasing the expression of interferon regulated genes in cancer cells in a subject, the promoters and/or enhancer regions of the genes comprise an IKZF1, IKZF3, or STAT1 binding site. In another embodiment, the promoters and/or enhancer regions of the genes comprise an HDAC1 or HDAC2 or HDAC3 binding site.

In some embodiments, the co-administration of the HDAC inhibitor and the IMiD increases the expression of an interferon regulated gene in a cancer cell that is one or more major histocompatibility complex (HLA) genes. Such increased expression of HLA gene(s) can enhance antigen presentation by antigen-presenting cells.

It should be noted that the expression of c-myc regulated genes is decreased in cancer cells co-administered an HDAC inhibitor and an IMiD. In other embodiments, such co-administration inhibits BIRCS (survivin) gene expression in cancer cells. Neither c-myc target genes nor BIRCS are interferon-regulated genes.

The HDAC inhibitor can be an HDAC6-selective inhibitor. An example of an HDAC6-selective inhibitor that can be used is Compound A. An exemplary IMiD is Compound F. Other combinations may be used other than Compound A and Compound F, such as Compounds B, C, or D with Compound E.

In an embodiment, lymphocyte proliferation disorder is treated by co-administering a therapeutically effective amount of an HDAC inhibitor and an IMiD to a subject in need thereof, wherein the co-administration treats the lymphocyte proliferative disorder. Lymphocyte proliferative disorders that can be treated by the disclosed methods include myelodysplastic syndrome (MDS) and acute myeloid leukemia (AML). The HDAC inhibitor can be an HDAC6-selective inhibitor. An exemplary HDAC6-selective inhibitor is Compound A. An example of an IMiD that can be used is Compound F. Other combinations may be used other than Compound A and Compound F, such as Compounds B, C, or D with Compound E.

In other embodiments, subjects are treated for infection by a pathogen comprising administering a therapeutically effective amount of an HDAC inhibitor and an IMiD to a subject in need thereof, wherein the infection is treated. The HDAC inhibitor can be an HDAC6-selective inhibitor. An example of an HDAC6-selective inhibitor that can be used is Compound A. An exemplary IMiD is Compound F. Other combinations may be used other than Compound A and Compound F, such as Compounds B, C, or D with Compound E.

Kits

In other embodiments, kits are provided. Kits include package(s) comprising compounds or compositions. In some embodiments, kits comprise an HDAC inhibitor, or a pharmaceutically acceptable salt thereof, and an IMiD or a pharmaceutically acceptable salt thereof.

"Package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering the disclosed compounds or compositions to a subject. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

c-MYC Upregulation c-MYC is a transcription factor that has been identified as an oncogene. Upregulation (or constitutive activation) of c-MYC leads to constitutive activation of MYC target genes and is associated with many diseases or disorders. Such diseases or disorders may have upregulated c-MYC. These diseases or disorders include, but are not limited to, multiple myeloma, breast cancer, colorectal cancer, T cell leukemia, pancreatic cancer, gastric cancer, lymphoma, ovarian cancer, prostate cancer, lung cancer, medulloblastoma, melanoma, and uterine cancer (Shou, Y., et al. (2000) Diverse karyotypic abnormalities of the c-myc locus associated with c-myc dysregulation and tumor progression in multiple myeloma. PNAS, 97, 228-233; Palomero, T., et al. (2006) NOTCH1 directly regulates c-MYC and activates a feed-forward-loop transcriptional network promoting leukemic cell growth. PNAS, 103, 18261-18266; He, T., et al. (1998) Identification of c-MYC as a target of the APC pathway. Science, 281, 1509-1512; Boxer and Dang (2001) Translocations involving c-myc and c-myc function. Oncogene, 20, 5595-5610).

Accordingly, provided herein in one aspect is a method of treating a cancer associated with upregulated c-MYC in a subject in need thereof, comprising administering to the subject an HDAC inhibitor (e.g., an HDAC6 inhibitor or an HDAC6-selective inhibitor) and an immunomodulatory drug (IMiD).

In one embodiment, the HDAC inhibitor and the IMiD are co-administered. In another embodiment, the HDAC inhibitor and the IMiD are administered sequentially. In certain embodiments, the method comprises administering a therapeutically effective amount of the HDAC inhibitor and a therapeutically effective amount of the IMiD.

In another embodiment, provided herein is a method of treating a cancer associated with upregulated c-MYC in a subject in need thereof, comprising administering to the subject compound A or compound B in combination with pomalidomide or lenalidomide.

In another embodiment, provided herein is a method of treating a cancer associated with upregulated c-MYC in a subject in need thereof, comprising administering to the subject compound A in combination with pomalidomide.

In another embodiment, provided herein is a method of treating a cancer associated with upregulated c-MYC in a subject in need thereof, comprising administering to the subject compound A in combination with lenalidomide.

In another embodiment, provided herein is a method of treating a cancer associated with upregulated c-MYC in a subject in need thereof, comprising administering to the subject compound B in combination with pomalidomide.

In another embodiment, provided herein is a method of treating a cancer associated with upregulated c-MYC in a subject in need thereof, comprising administering to the subject compound B in combination with lenalidomide.

For the any of the above embodiments, the cancer associated with upregulated c-MYC is selected from the group consisting of multiple myeloma, breast cancer, colorectal cancer, T cell leukemia, pancreatic cancer, gastric cancer, lymphoma, ovarian cancer, prostate cancer, lung cancer, medulloblastoma, melanoma, and uterine cancer.

Interferon Response

The induced expression of interferons and the activation of interferon regulated genes lead to increased immune response against malignant cells within the tumor microenvironment and apoptosis in cancer cells (Leonova, K., et al. (2012) p53 cooperates with DNA methylation and a suicidal interferon response to maintain epigenetic silencing of repeats and noncoding RNAs. PNAS, E89-E98). This immune response, or "interferon sensitivity," results in a reduction in tumor burden in a subject with malignant disease. Diseases or disorders associated with interferon sensitivity include but are not limited to multiple myeloma, breast cancer, lymphoma, lung cancer, melanoma, chronic myeloid leukemia, and colorectal cancer (Zhao, H. et al. (2017) The immunomodulatory anticancer agent, RRx-001 induces interferon response through epigenetic induction of viral mimicry. Clin. Epigenet.; Roulois, D. et al. (2015) DNA-methylating agents target colorectal cancer cells by inducing viral mimicry by endogenous transcripts. Cell, 162, 961-973). Prior to treatment, such cancers may have decreased expression of interferons, or decreased or low activation of interferon regulated genes.

Accordingly, provided herein in one aspect is a method of treating a cancer having interferon sensitivity in a subject in need thereof, comprising administering to the subject an HDAC inhibitor (e.g., an HDAC6 inhibitor or an HDAC6-selective inhibitor) and an immunomodulatory drug (IMiD).

In one embodiment, the HDAC inhibitor and the IMiD are co-administered. In another embodiment, the HDAC inhibitor and the IMiD are administered sequentially. In certain embodiments, the method comprises administering a therapeutically effective amount of the HDAC inhibitor and a therapeutically effective amount of the IMiD.

In another embodiment, provided herein is a method of treating a cancer having interferon sensitivity in a subject in need thereof, comprising administering to the subject compound A or compound B in combination with pomalidomide or lenalidomide.

In another embodiment, provided herein is a method of treating a cancer having interferon sensitivity in a subject in need thereof, comprising administering to the subject compound A in combination with pomalidomide.

In another embodiment, provided herein is a method of treating a cancer having interferon sensitivity in a subject in need thereof, comprising administering to the subject compound A in combination with lenalidomide.

In another embodiment, provided herein is a method of treating a cancer having interferon sensitivity in a subject in need thereof, comprising administering to the subject compound B in combination with pomalidomide.

In another embodiment, provided herein is a method of treating a cancer having interferon sensitivity in a subject in need thereof, comprising administering to the subject compound B in combination with lenalidomide.

For the any of the above embodiments, the cancer having interferon sensitivity is selected from the group consisting of multiple myeloma, breast cancer, colorectal cancer, T cell leukemia, pancreatic cancer, gastric cancer, lymphoma, ovarian cancer, prostate cancer, lung cancer, medulloblastoma, melanoma, and uterine cancer.

EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Definitions of the variables in the structures in the schemes herein are commensurate with those of corresponding positions in the formulae presented herein.

The synthesis of the compounds of Formula I is provided in PCT/US2011/021982, which is incorporated herein by reference in its entirety. The synthesis of compounds of Formula II is provided in PCT/US2011/060791, which is incorporated herein by reference in its entirety. The synthesis of the compounds of Formula III is provided in U.S. Pat. Nos. 5,635,517; 6,281,230; 6,335,349; and 6,476,052; and in International Patent Application No. PCT/US97/013375, each of which is incorporated herein by reference in its entirety. The synthesis of 2-(diphenylamino)-N-(7-(hydroxyamino)-7-oxoheptyl)pyrimidine-5-carboxamide (Compound A), the synthesis of 2-((2-chlorophenyl)(phenyl)amino)-N-(7-(hydroxyamino)-7-oxoheptyl)pyrimidine-5-carboxamide (Compound B), the synthesis of 2-((1-(3-fluorophenyl)cyclohexyl)amino)-N-hydroxypyrimidine-5-carboxamide (Compound C), and the synthesis of N-hydroxy-2-((1-phenylcyclopropyl)amino)pyrimidine-5-carboxamide (Compound D) are all provided in International Patent Application No. PCT/U14/59387 (WO 2015/054175), which is incorporated herein by reference in its entirety; this application also presents the HDAC6 assays used to evaluate these compounds.

Example 1

HDAC6 Inhibitors Synergize with IMiDs in Multiple Myeloma Cell Killing

Figure 4A:
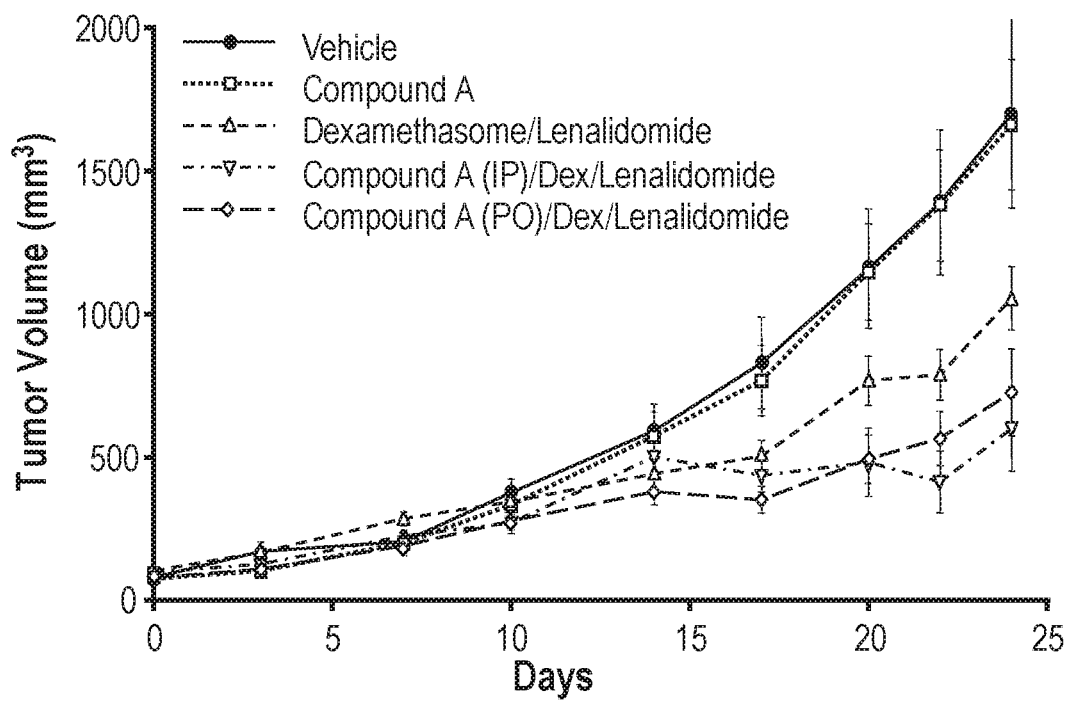
FIG. 4A is a graph that shows inhibition of MM.1s xenograft tumor growth with various combinations of Compound A, lenalidomide, and/or dexamethasone.
Figure 9A:
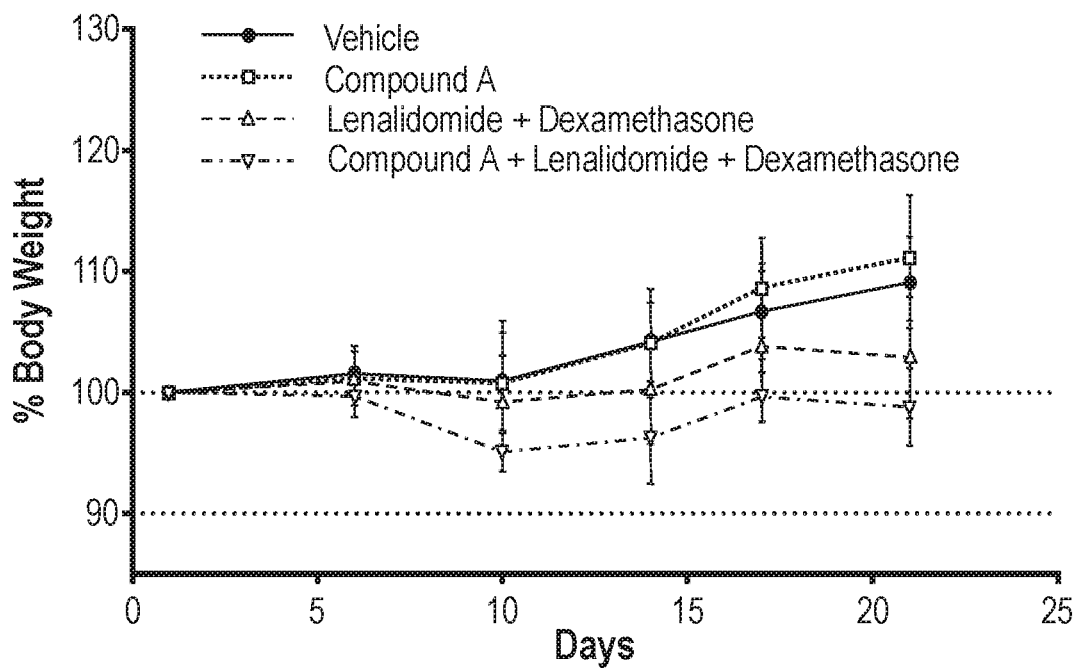
FIG. 9A is a graph showing the effects of treatment of SCID-beige mice with Vehicle, Compound A alone, lenalidomide plus dexamethasone, or the triple combination of lenalidomide, dexamethasone, and Compound A.

In this experiment, it is shown that combining an HDAC6-selective inhibitor (Compound A or Compound B)

with either lenalidomide or pomalidomide leads to synergistic decreases in the viability of two different multiple myeloma cell lines in vitro (MM.1s and H929; FIGS. 1 and 2). The relevance of inhibition of HDAC6 to this synergistic effect was validated by demonstrating synergistic interactions of either IMiD molecule with Compound C, which is more than 300-fold selective for HDAC6 over class I HDACs. Additionally, staining of H929 cells for markers of apoptosis demonstrated that treatment with a combination of Compound A plus an IMiD led to an approximately 1.6-2 fold increase in cells entering apoptosis relative to cells treated with either agent alone. Further, the combination of Compound A, lenalidomide, and dexamethasone was well tolerated in vivo with no overt evidence of toxicity (FIG. 9A), and an in vivo efficacy study with this combination in a xenograft model of multiple myeloma showed enhanced tumor growth inhibition by the triple combination over lenalidomide plus dexamethasone alone (FIG. 4A).

Briefly, for viability assays, cells were seeded in 384-well plates and treated in quadruplicate in a dose-matrix format with an HDAC6-selective inhibitor (Compound A, Compound B, or Compound C) in combination with lenalidomide or pomalidomide. After incubating these cells for 48 hr, total cell viability was assessed via an MTS assay (Aqueous One, Promega). The fraction affected (Fa) was subsequently determined for each dose combination and the combination index (CI) was assessed using the method of Chou-Talalay. CI values less than one represent a synergistic effect, values equal to one suggest an additive effect, and values greater than two indicate an antagonistic effect As can be seen in the Fa-CI plots in FIGS. 1A-C and 2A-C, in both myeloma cell lines all HDAC6-selective inhibitors showed strong evidence of synergy with the tested IMiDs across a broad range of Fa's. This is evidenced by the large number of data points (representing individual dose combinations) in the Fa-CI plot that fall below the highly stringent cutoff of 0.7.

Figure 3A:
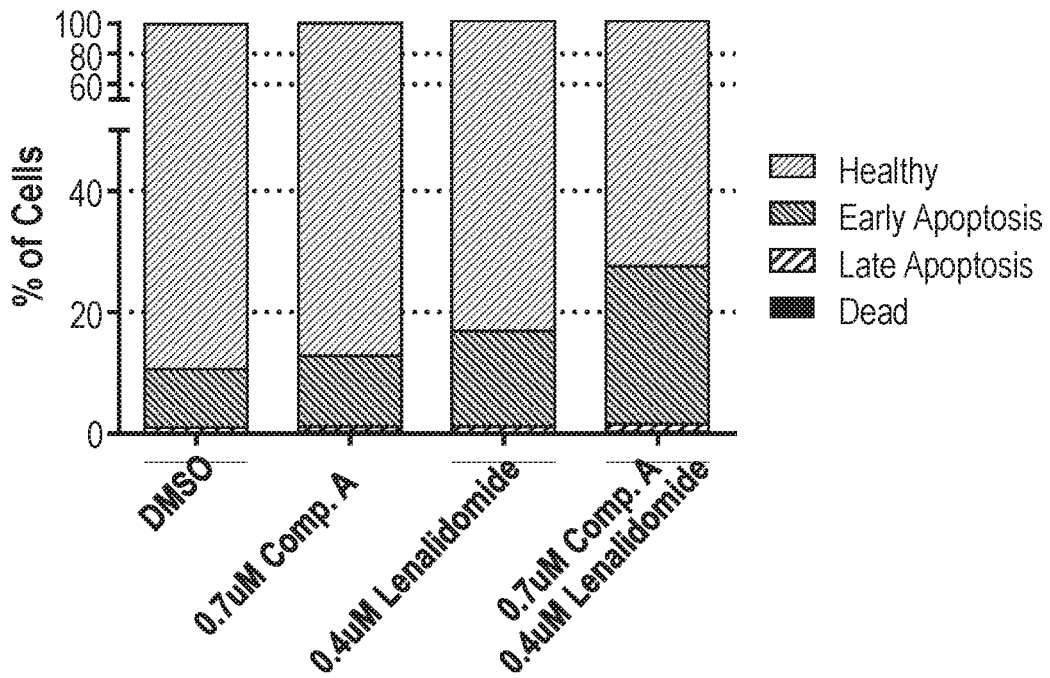
FIGS. 3A-B is a pair of graphs that show increased apoptosis in H929 cells treated with Compound A and an IMiD.
Figure 3B:
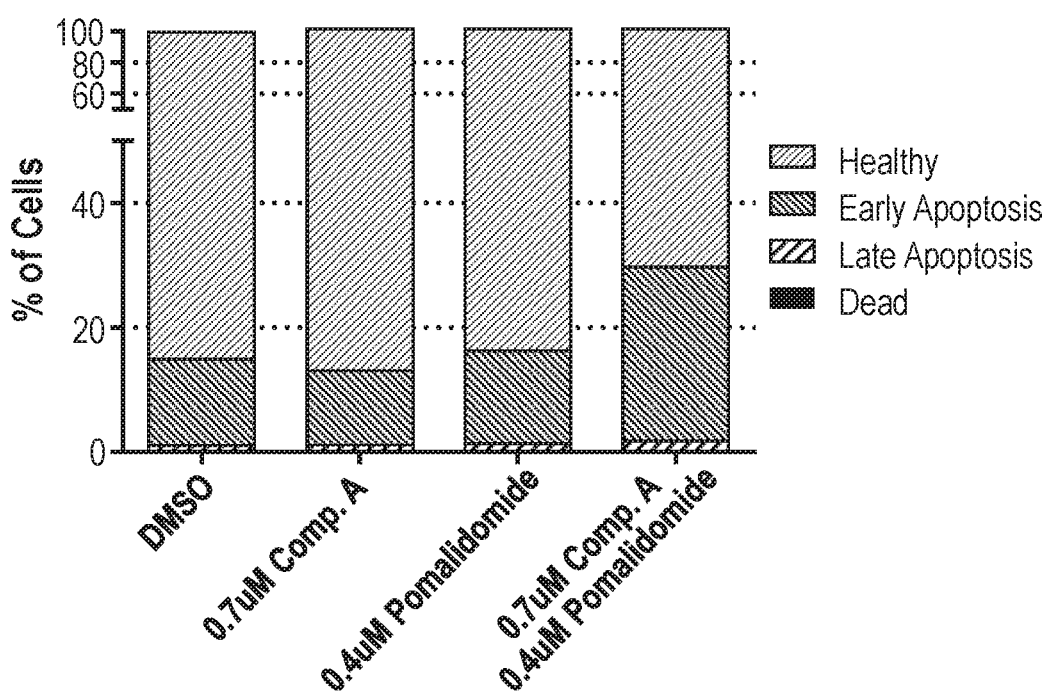

To test for the induction of apoptosis, H929 cells were treated with DMSO, 0.7 µM Compound A, 0.4 µM lenalidomide, or the combination of both drugs for 72 hours. Alternatively, H929 cells were treated for 72 hours with DMSO, 0.7 µM Compound A, 0.02 µM pomalidomide, or the combination of both drugs Cells were then harvested and stained with Annexin V (which recognizes an epitope on cells in the early stages of apoptosis) and propidium iodide (which is excluded from cells with intact membranes, thus marking only dead cells). Flow cytometry analysis was then used to measure the number of healthy and apoptotic cells under each treatment condition. While treatment with low doses of each compound individually did not result in the induction of apoptosis, combination treatment with Compound A plus an IMiD resulted in an approximate doubling in the percentage of cells undergoing apoptosis. See FIGS. 3A-B.

For animal studies, MM.1s cells were implanted subcutaneously in immunocompromised mice. Upon establishment of tumors, the animals were separated into groups and treated with vehicle alone, Compound A alone (30 mpk IP), lenalidomide (15 mpk IP) plus dexamethasone (lmpk IP), or lenalidomide and dexamethasone plus Compound A delivered either orally (100 mpk BID PO) or intraperitoneally (30 mpk IP). While treatment with lenalidomide plus dexamethasone delayed tumor growth in this model, the addition of Compound A to this combination resulted in even greater tumor growth inhibition. Together, these results (see FIG. 4A) provide strong evidence that inhibition of HDAC6 in combination with an IMiD results in synergistic cell killing, and further suggests that combinations of drugs targeting HDAC6 with IMiDs may provide significant clinical benefit for multiple myeloma patients.

Example 2

Combinations of HDAC6 Inhibitors and IMiDs Results in Synergistic Decreases in Myeloma Cell Growth and Viability This example shows that the combination of HDAC6-selective inhibitors and IMiDs results in synergistic decreases in myeloma cell growth and viability.

Figure 5C:
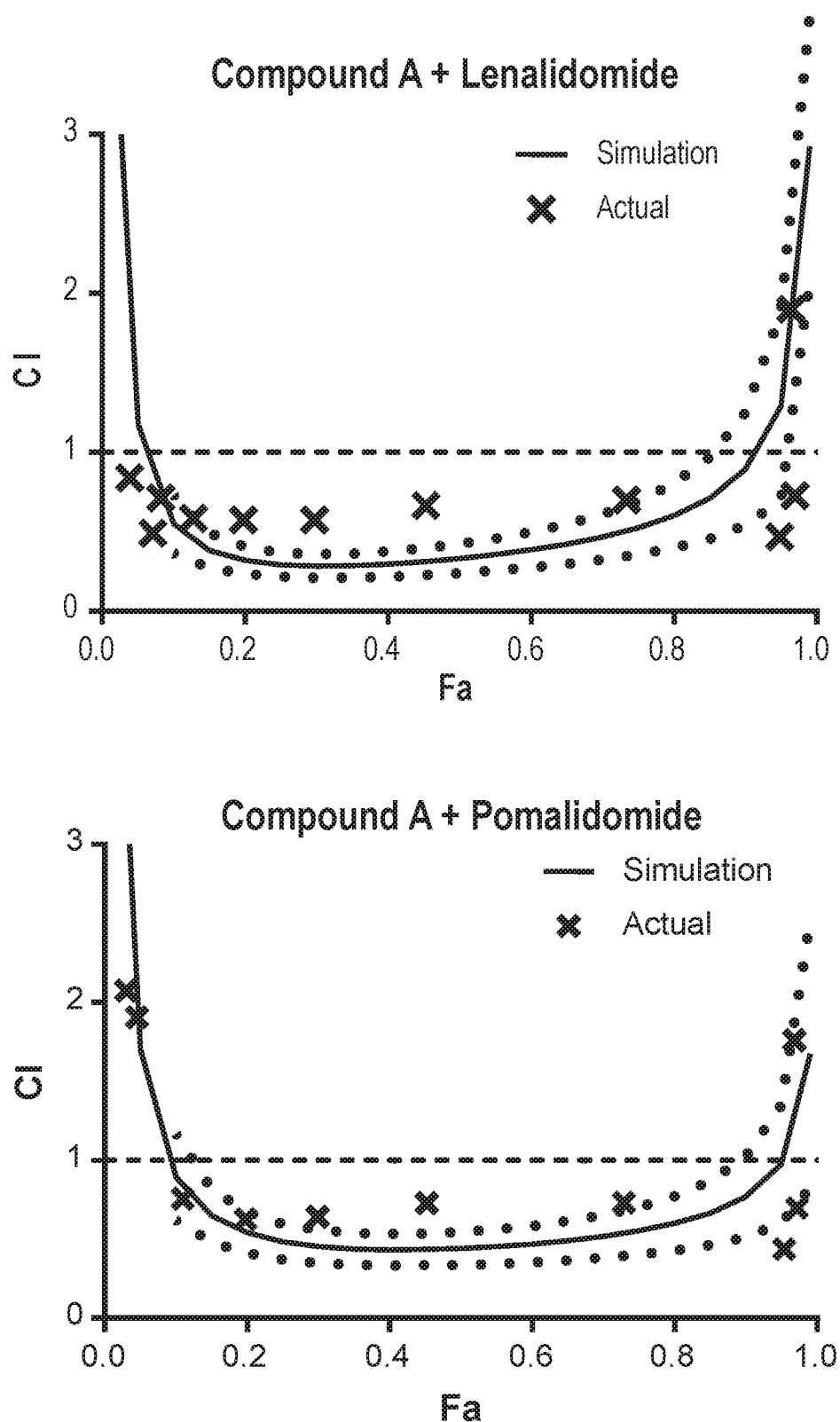

H929 (FIGS. 5A & 5B) or MM.1s (FIGS. 5C & 5D) myeloma cells were exposed to increasing doses of the HDAC6-selective inhibitors Compound A (FIGS. 5A & 5C) or Compound C (FIGS. 5B & 5D) alone or in combination with lenalidomide (FIGS. 5A & 5C) or pomalidomide (FIGS. 5B & 5D). A constant ratio was maintained between the dose of the HDAC6i and IMiD, and cell viability was assessed at 72 hr by MTS assay. Calcusyn software was then used to determine the combination index (CI) value at each dose combination and the relative fraction affected ($F_A$) (Actual), and a simulation was run to estimate the CI value across the entire $F_A$ range (Simulation). The measurement of CI values less than 1 in all combinations strongly support a synergistic interaction between the HDAC6i and IMiDs tested.

Example 3

The Combination of an HDAC6 Inhibitor and IMiDs Affects Cellular Proliferation and Cell Cycle Progression This example shows that treatment of multiple myeloma cells with Compound A and/or IMiDs results in decreased cell cycle progression.

Figure 6A:
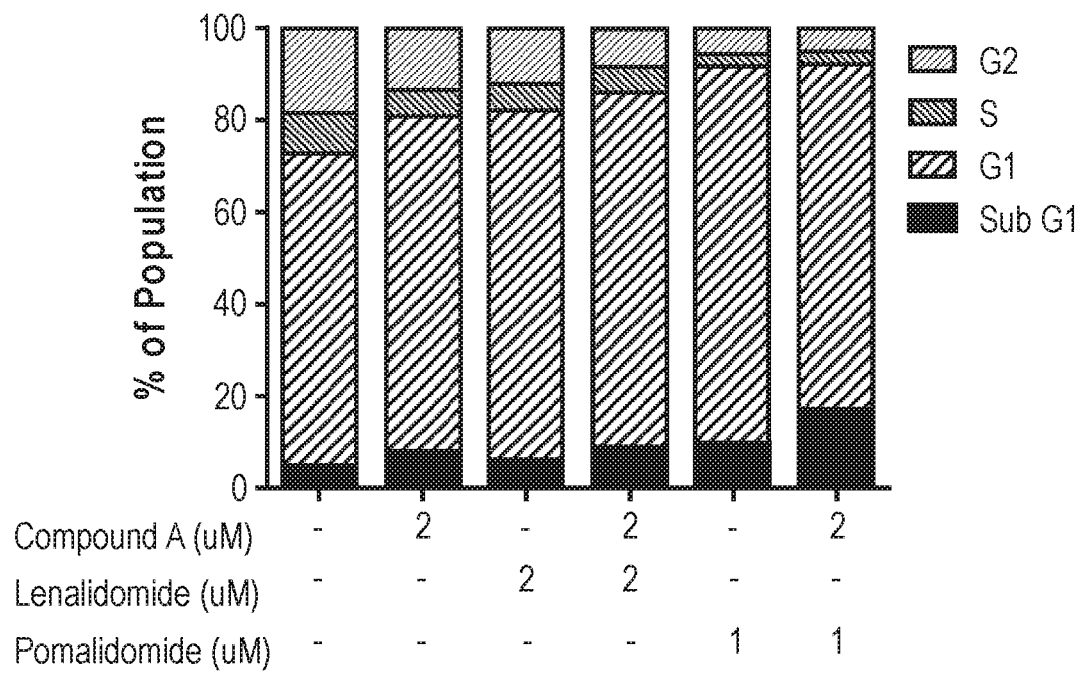
FIGS. 6A-D are a series of graphs showing that combination treatment of multiple myeloma cells with Compound A and/or IMiDs results in decreased cell cycle progression relative to either single agent.
Figure 6B:
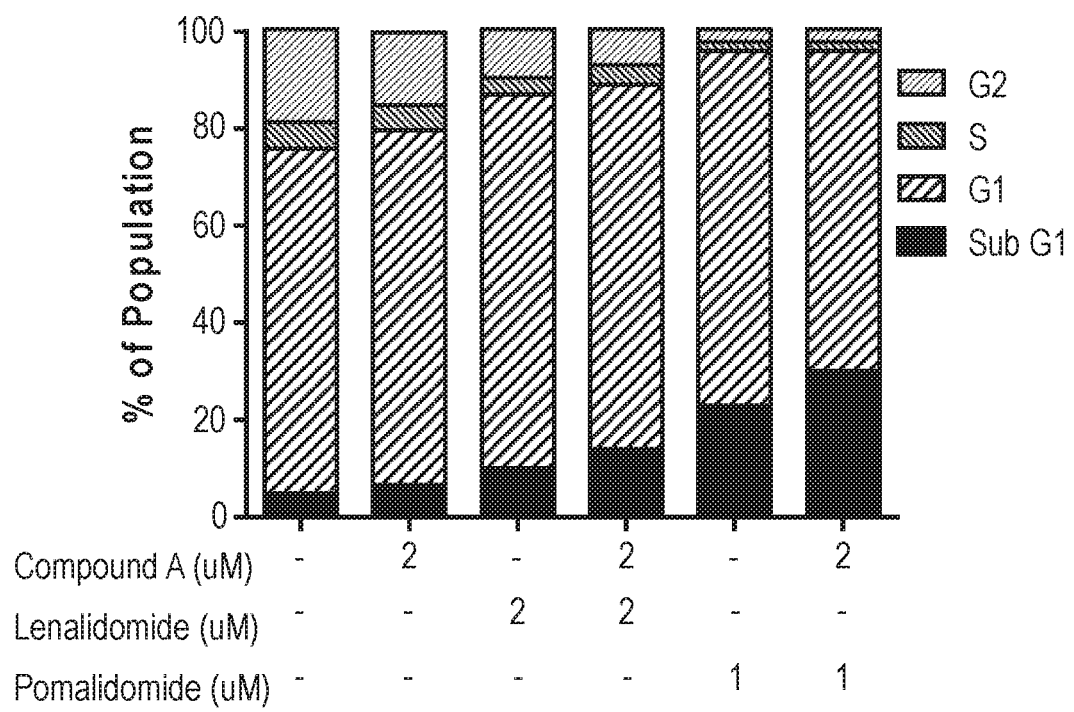
Figure 6C:
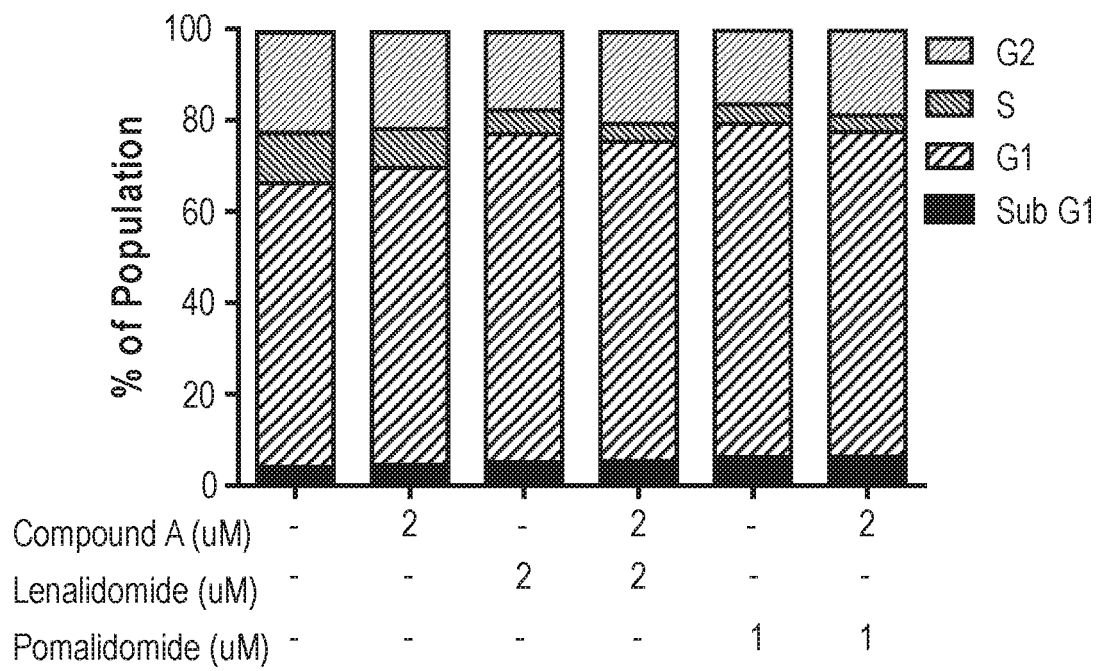
Figure 6D:
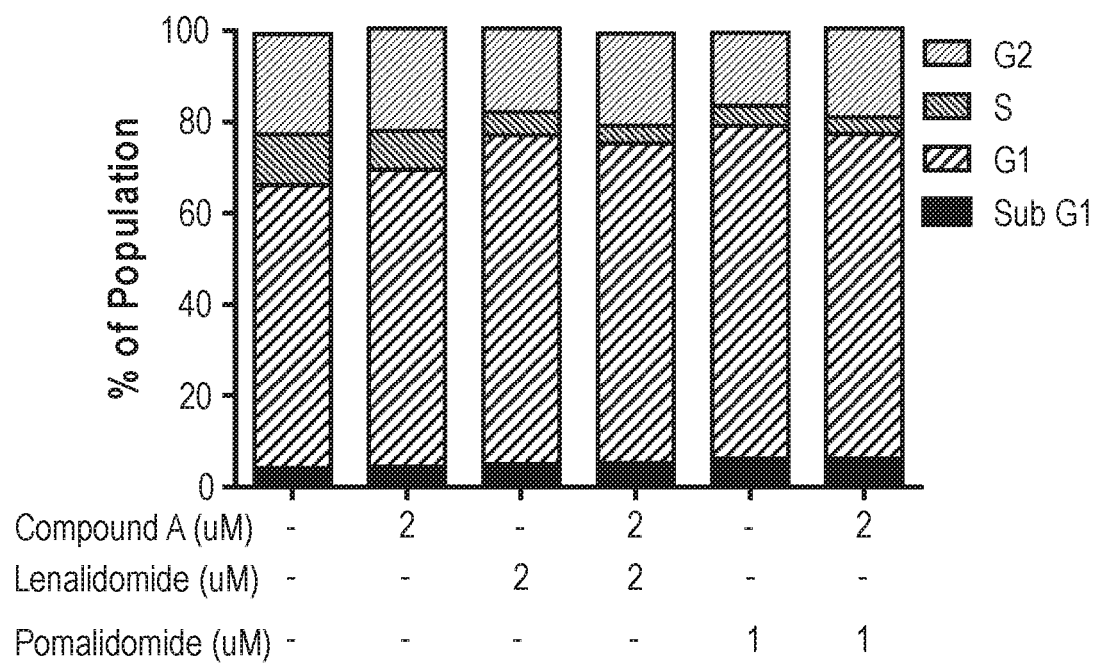

H929 (FIGS. 6A & 6B) or MM.1s (FIGS. 6C & 6D) myeloma cells were exposed to drug for 3 (FIGS. 6A & 6C) and 5 (FIGS. 6B & 6D) days and cell cycle distribution was assessed by flow cytometry via incorporation of propidium iodide. The relative fraction of cells in each stage of the cell cycle (G0/G1, S, and G2/M) as well as the fraction of dead cells (Sub G1) was then estimated. The cells were treated with DMSO, Compound A (2 µM) lenalidomide (2 µM) pomalidomide (1 µM) or combinations of Compound A with either IMiD. Treatment with Compound A resulted in a small reduction of cells undergoing division in S phase, while treatment with either IMiD, alone or in combination with Compound A, led to a reduction in the percentage of cells in the S and G2/M phases and a concomitant increase in cells in G0/G1. These results are consistent with decreased proliferation in response to treatment with Compound A and/or IMiDs that accumulates with prolonged exposure to the drug combination.

Example 4

The Combination of an HDAC6 Inhibitor and IMiDs Induces Apoptosis in Multiple Myeloma Cells This example shows that treatment of multiple myeloma cells with Compound A plus IMiDs results in synergistic increases in cellular apoptosis.

Figure 7A:
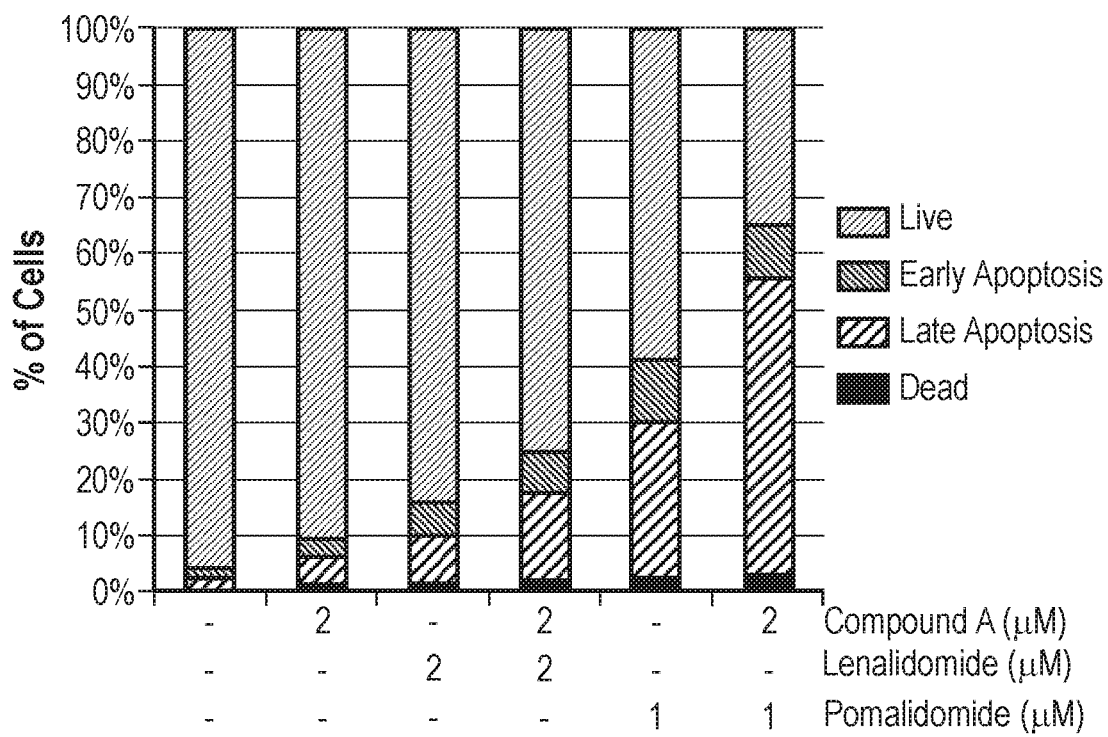
FIGS. 7A-D are a series of graphs showing that combination treatment of multiple myeloma cells with Compound A and IMiDs results in synergistic increases in cellular apoptosis.
Figure 7B:
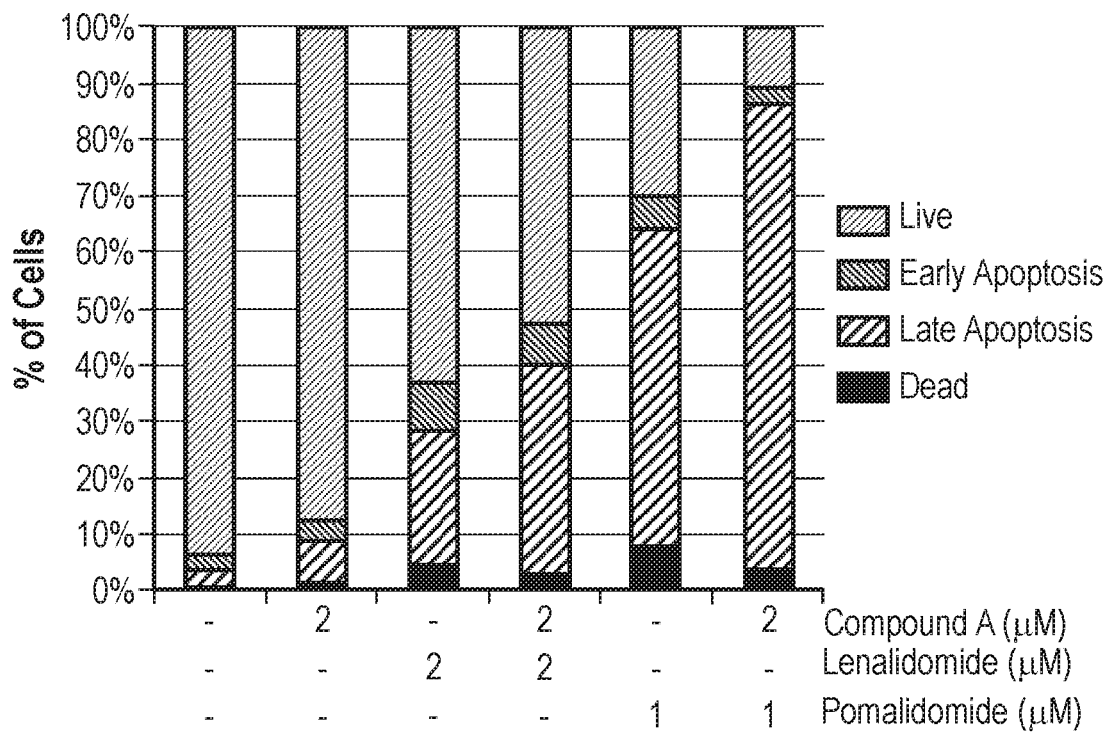
Figure 7C:
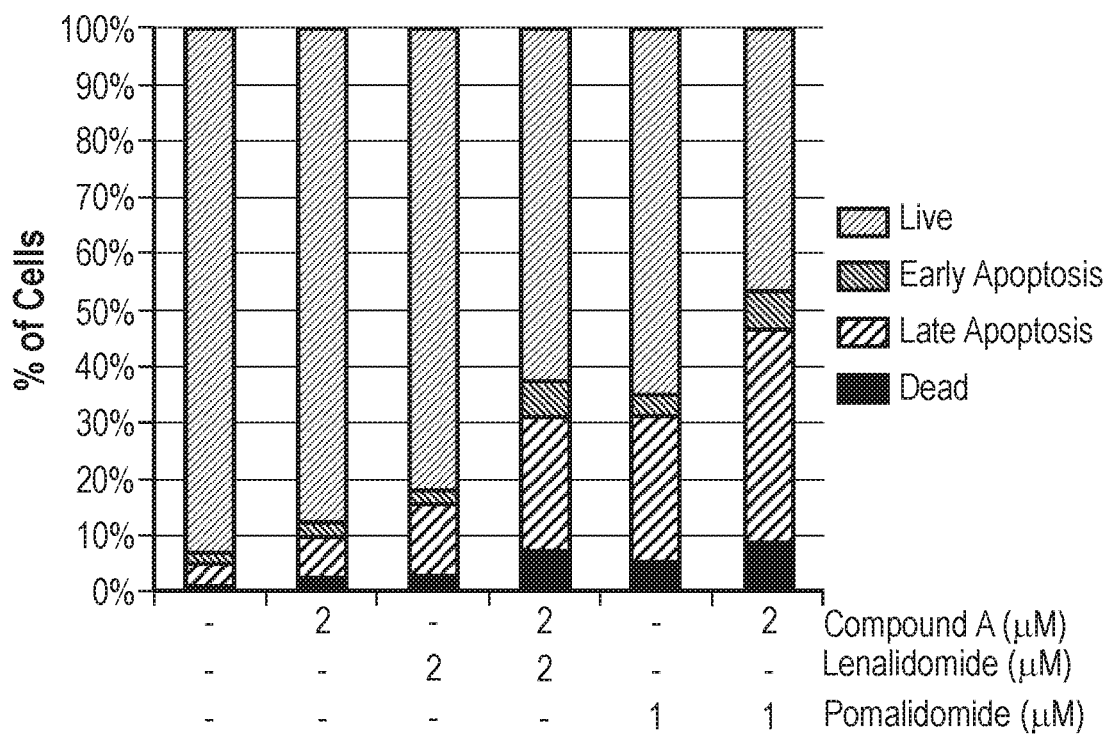
Figure 7D:
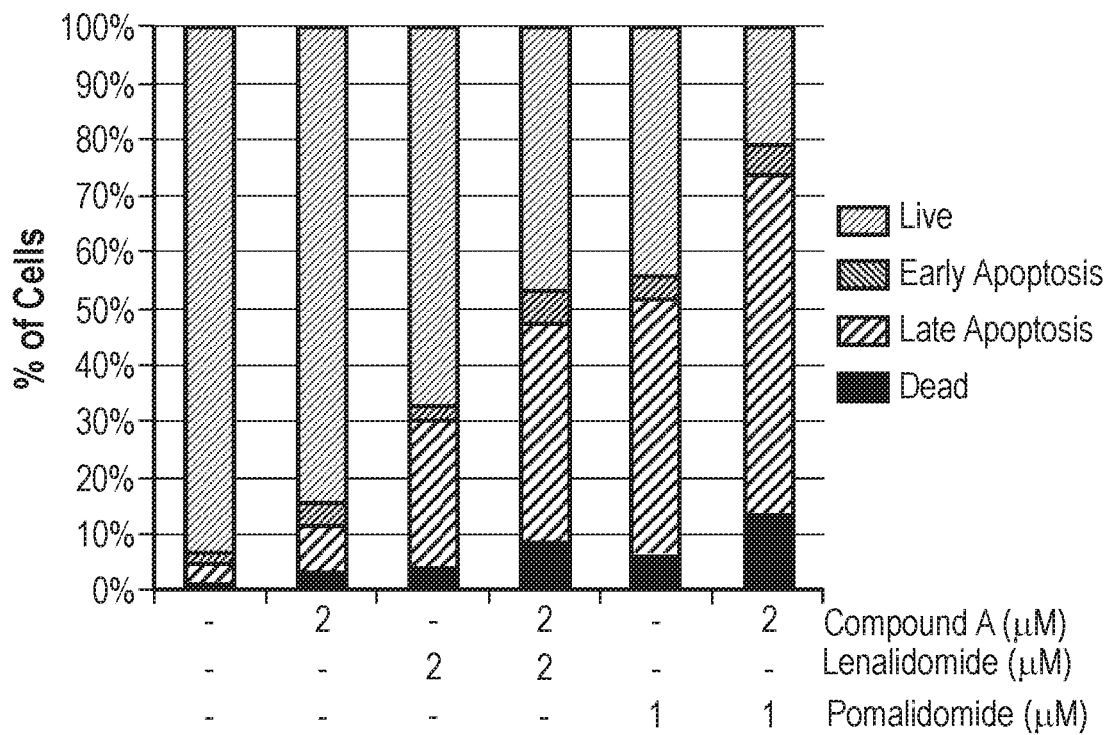

H929 (FIGS. 7A & 7B) or MM.1s (FIGS. 7C & 7D) myeloma cells were exposed to drug for 5 (FIGS. 7A & 7C) and 7 (FIGS. 7B & 7D) days, and apoptosis was assessed by flow cytometry by measuring Annexin V binding and cellular permeability to propidium iodide. The relative fraction of cells that were live, in early apoptosis, in late apoptosis, or dead was then determined. The cells were treated with DMSO, Compound A (2 µM), lenalidomide (2 µM), pomalidomide (1 µM), or combinations of Compound A with either IMiD. Treatment with Compound A (2 µM) resulted in a small increase in apoptosis relative to control cells, while treatment with either IMiD resulted in significantly more apoptotic cells at both time points. However, the combination of Compound A with either IMiD resulted in synergistic increases in the percentage of apoptotic cells. The percentage of cells actively undergoing apoptosis also increased with longer exposure times to the drug combinations.

Example 5

The Combination of an HDAC6 Inhibitor and IMiDs Decreases mRNA and Protein Expression Level of MYC and IRF4 and Increases P21 Expression This example shows that the expression level of MYC and IRF4 are decreased by treatment with Compound A and IMiDs, while expression of P21 is increased by treatment with this combination.

Figure 8A:
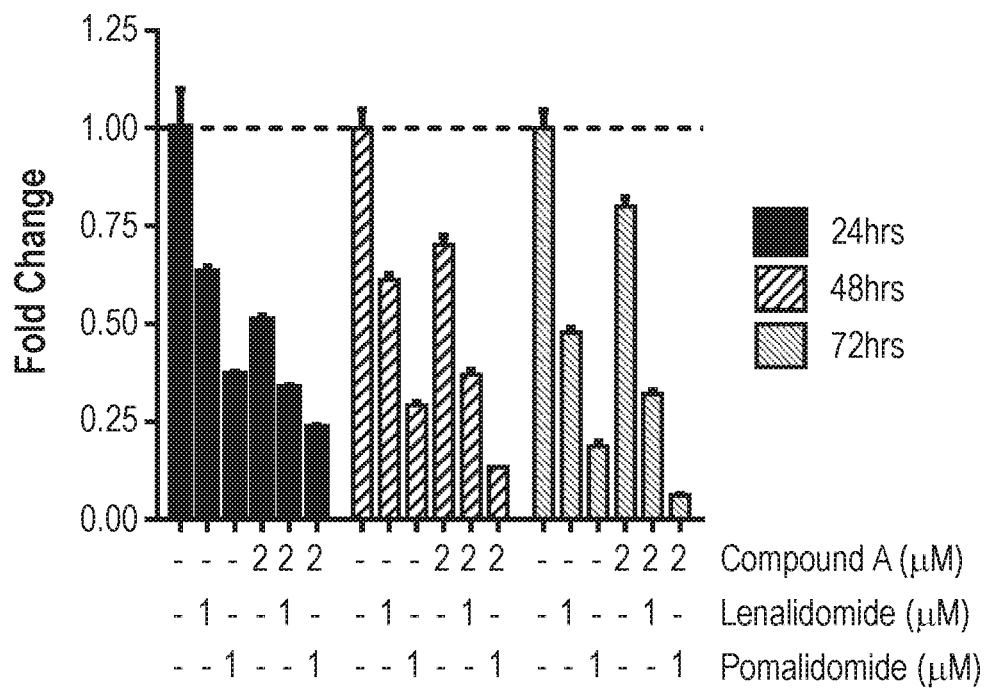
FIGS. 8A-E are a series of graphs showing that the mRNA expression level of MYC and IRF4 are decreased by combination treatment with Compound A and IMiDs, and that P21 expression is increased by the combination treatment.
Figure 8B:
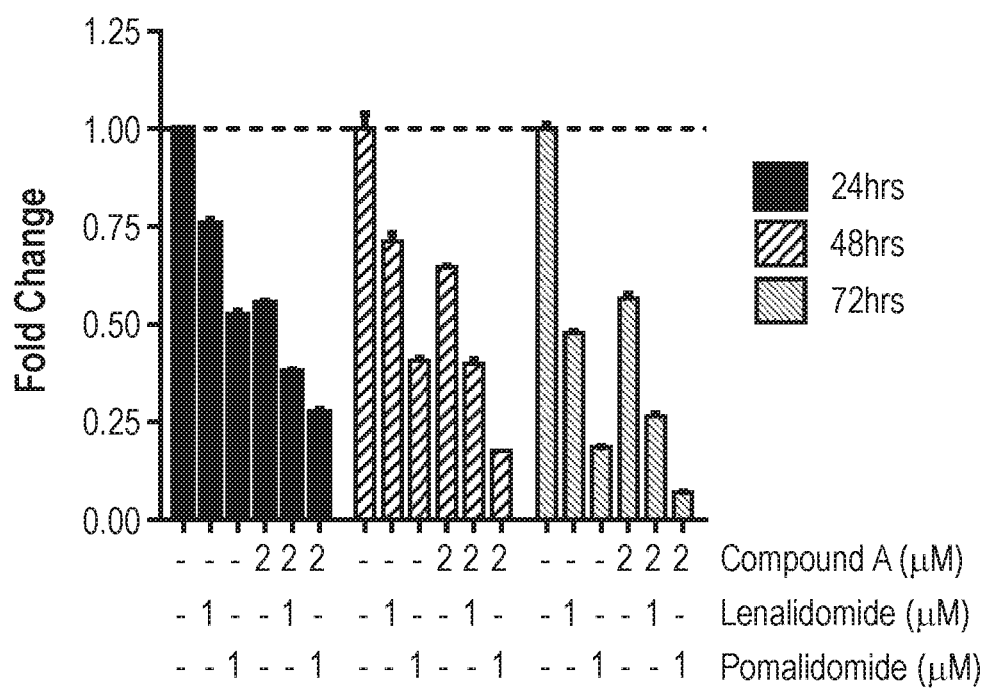
Figure 8C:
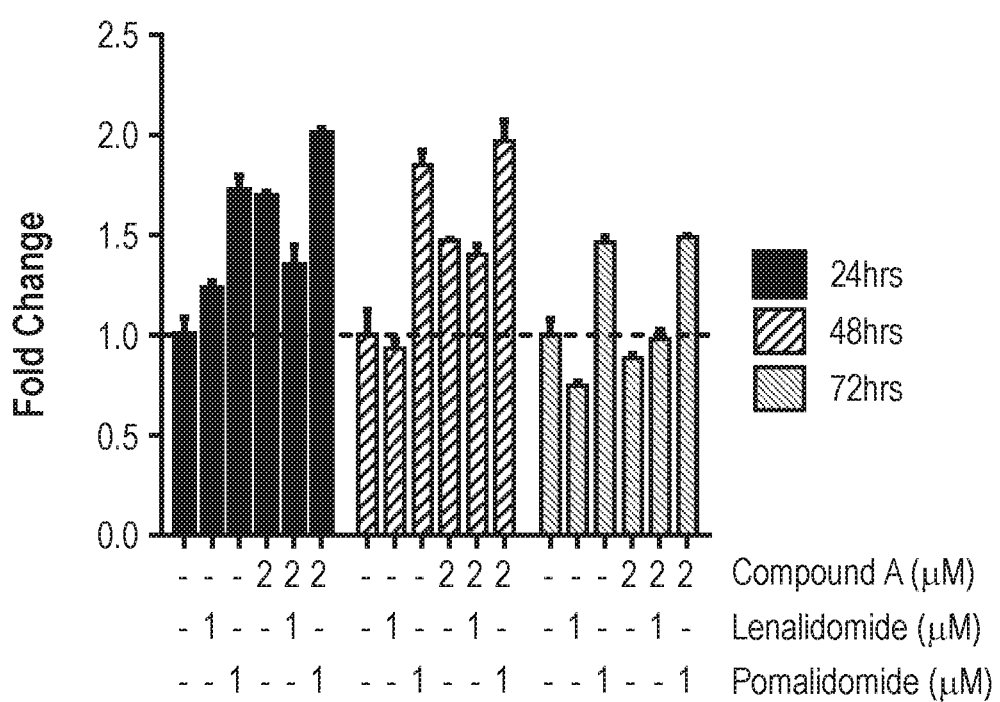
Figure 8D:
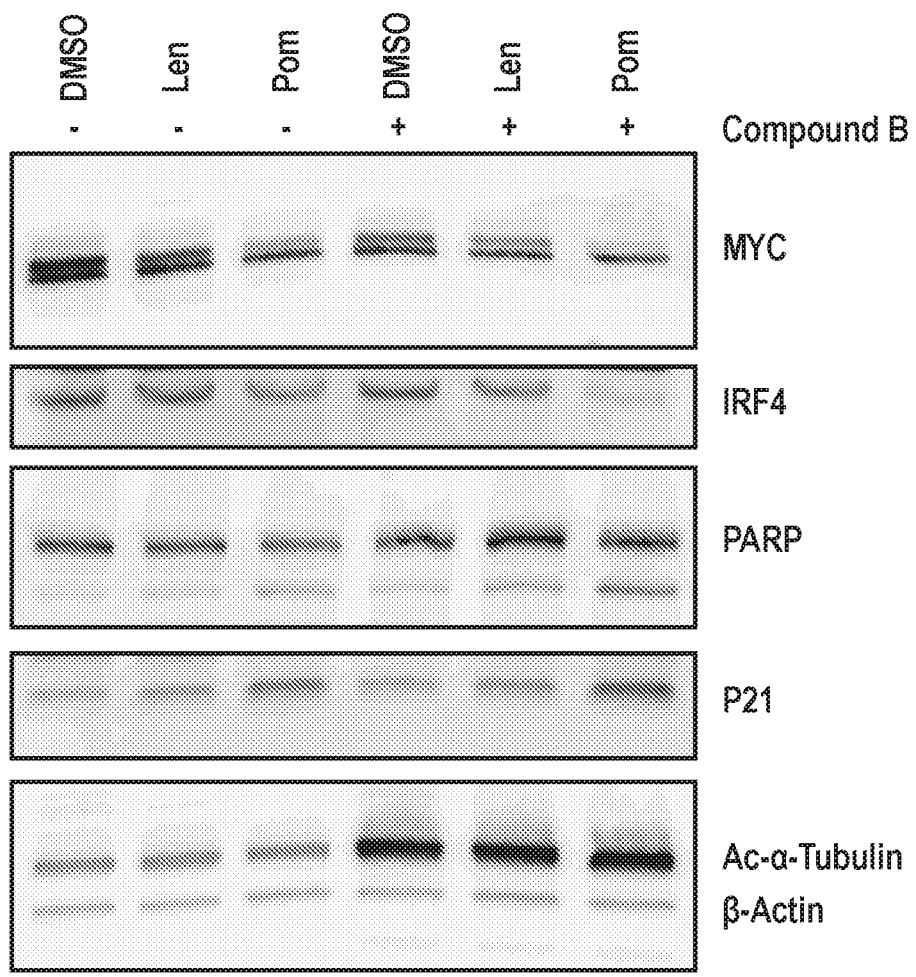

H929 myeloma cells were treated with DMSO, Compound A (2 µM), lenalidomide (1 µM) pomalidomide (1 µM), or combinations of Compound A with either IMiD, and total RNA was harvested 24, 48, and 72 hours later. Quantitative reverse transcription PCR was then performed to assess the relative transcript levels of MYC (FIG. 8A), IRF4 (FIG. 8B), and P21 (FIG. 8C) at each time point. MYC and IRF4 are critical transcription factors that are overexpressed in multiple myeloma cells, and myeloma cells were previously shown to exhibit dependence on both transcripts (*Nature,* 454: 226; *Blood,* 120: 2450). While both genes were decreased by all single agent treatments, combination treatment with Compound A and either IMiD resulted in further decreases in expression of these important transcripts. P21 is an inhibitor of the cell cycle, and thus increased expression of P21 would be expected to inhibit proliferation. The reduction of MYC and IRF4, and the increase of P21 expression, was confirmed at the protein level by immunoblot in H929 cells after 48 hours of combination treatment (FIG. 8D). Induction of apoptosis was also confirmed by the induction of PARP cleavage by combination treatment. Inhibition of HDAC6 by Compound A was confirmed by the detection of hyperacetylation of α-tubulin.

Example 6

Compound B, a Selective Inhibitor of HDAC6, Synergizes with IMiDs in Multiple Myeloma (MM) Cells HDAC enzymes represent attractive therapeutic targets in MM, but non-selective HDAC inhibitors have led to dose-limiting toxicities in patients, particularly in combination with other therapeutic agents. Ricolinostat (Compound A), a first-in-class orally available HDAC inhibitor that is 11-fold selective for HDAC6, synergizes in vitro and in vivo with bortezomib in preclinical models of MINI (*Blood,* 20[210]: 4061), and has thus far demonstrated an improved safety and tolerability profile in Phase I trials (Raj e, et al, EHA, 2014). Based on these findings, Compound B is being developed as a second generation, orally available, isoform selective inhibitor of HDAC6 for clinical evaluation in MM.

Figure 5F:
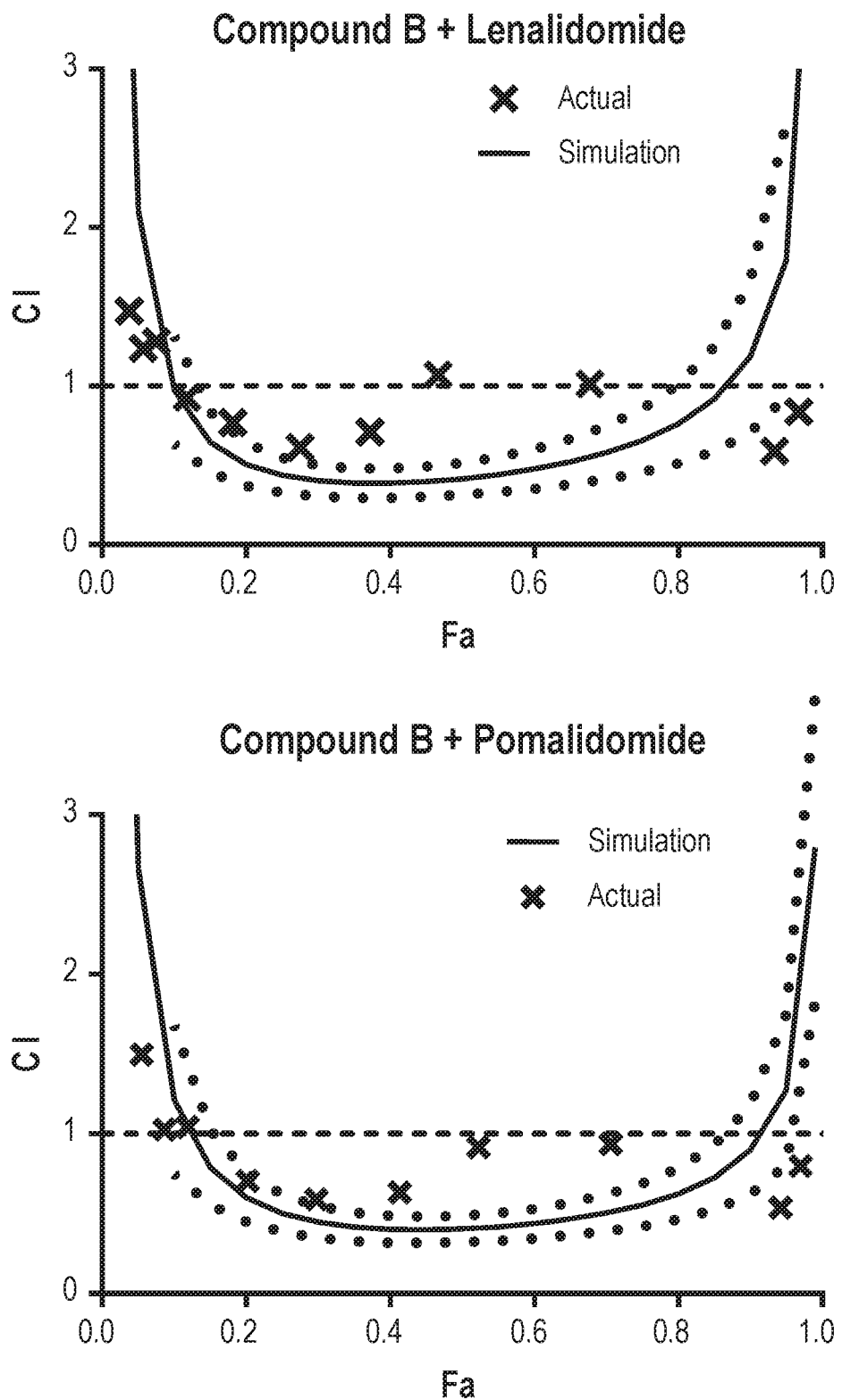

In support of the ongoing clinical development program for Compound B in MM, it is shown here that combining Compound B with either IMiD leads to synergistic decreases in the viability of MM cells in vitro. FIGS. 5E-F are sets of graphs showing that the combination of HDAC6-selective inhibitors and IMiDs resulted in synergistic decreases in myeloma cell growth and viability. FIG. 5E shows the results of experiments in which H929 myeloma cells were exposed to increasing doses of Compound B in combination with lenalidomide (top panel) or pomalidomide (bottom panel) at constant ratios. FIG. 5F shows the results of experiments in which MM.1s myeloma cells were exposed to increasing doses of Compound B in combination with lenalidomide (top panel) or pomalidomide (bottom panel) at constant ratios.

Figure 6E:
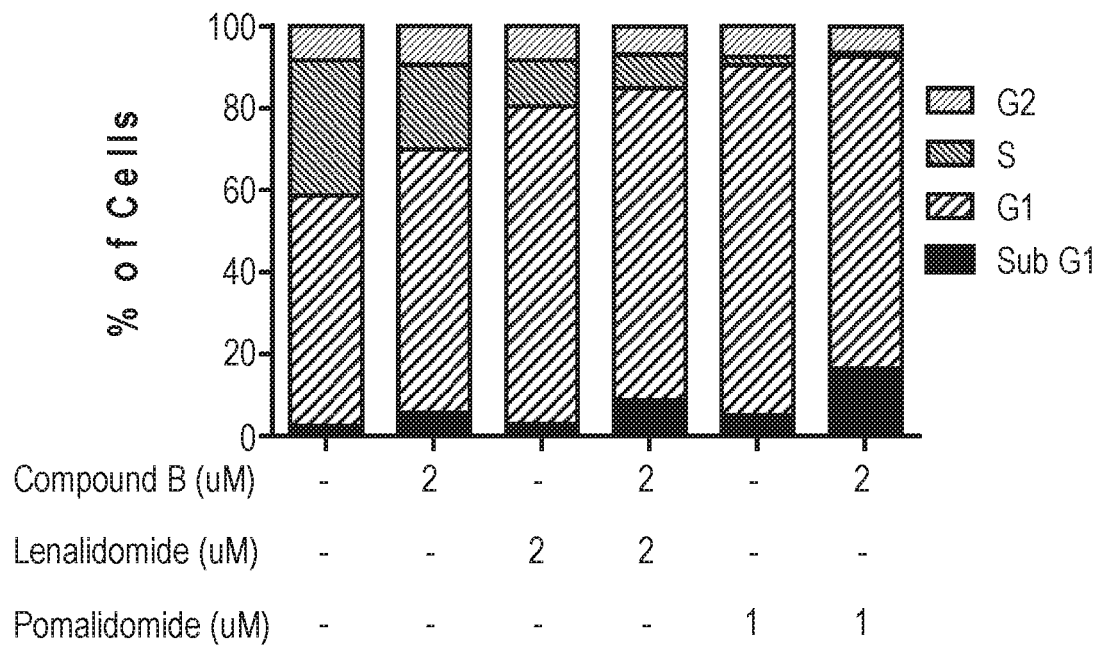
FIGS. 6E-F are graphs showing that combination treatment of multiple myeloma cells with Compound B and/or IMiDs resulted in decreased cell cycle progression relative to either single agent.
Figure 6F:
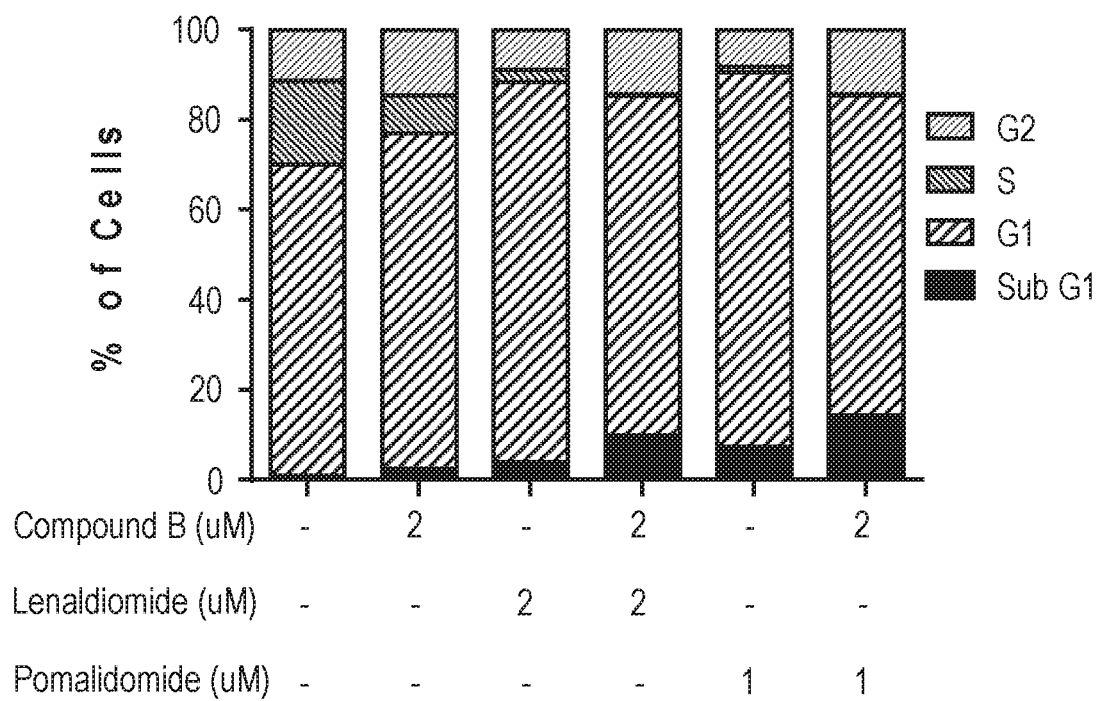
Figure 7E:
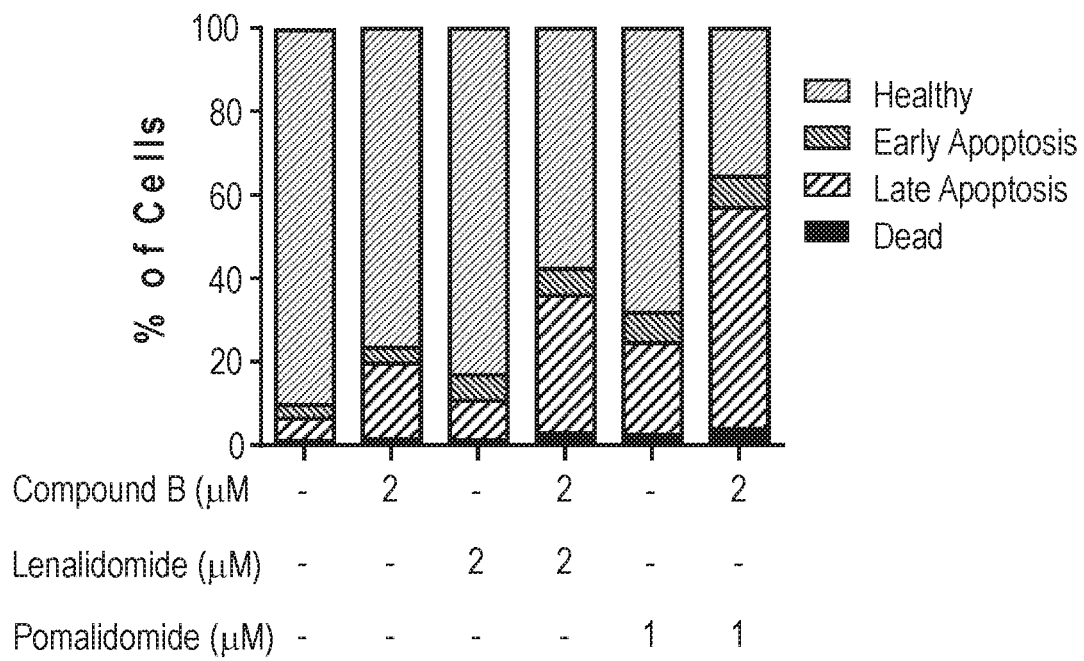
FIGS. 7E-F are graphs showing that treatment of multiple myeloma cells with Compound B and IMiDs results in synergistic increases in cellular apoptosis.
Figure 7F:
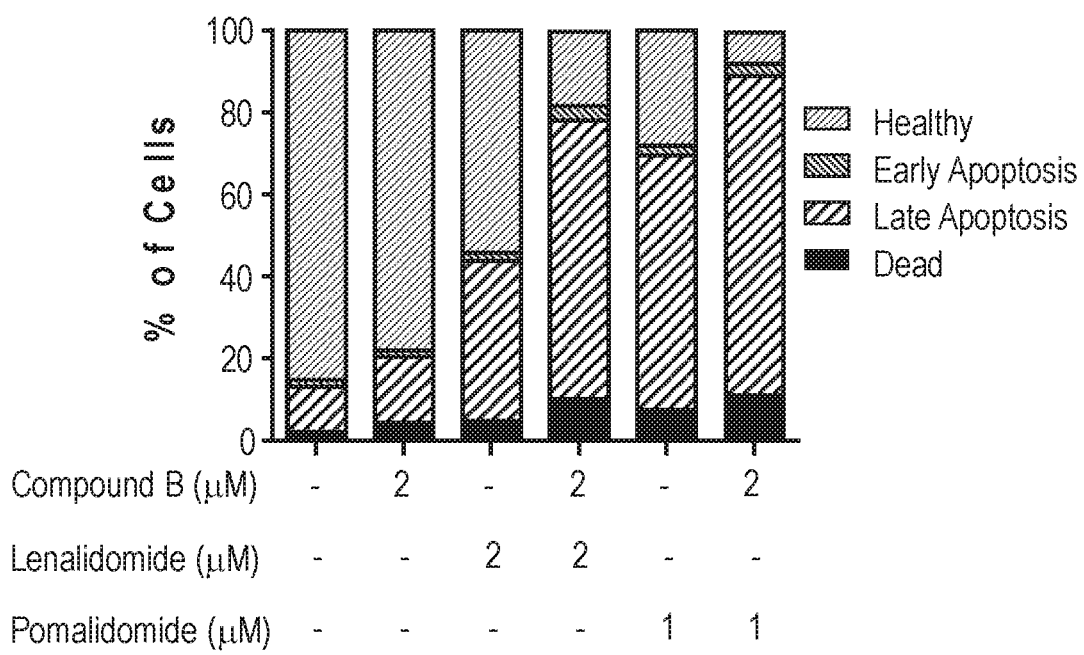

Time course studies demonstrated accumulation of cell cycle arrest in cells after prolonged exposure to either IMiD, as well as progressive induction of apoptosis in these cells. Notably, though, the addition of Compound B to either IMiD resulted in synergistic increases in the percentage of MM cells undergoing apoptosis. FIG. 6E-F are graphs showing that treatment of multiple myeloma cells with Compound B and/or IMiDs resulted in decreased cell cycle progression. FIG. 6E shows the effect of treatment of H929 myeloma cells for 4 days with DMSO, Compound B (2 µM), lenalidomide (2 µM), pomalidomide (1 µM), or combinations of Compound B with either IMiD on cell cycle inhibition. FIG. 6F shows the effect of treatment of MM.1s myeloma cells for 5 days with DMSO, Compound B (2 µM), lenalidomide (2 µM), pomalidomide (1 µM), or combinations of Compound B with either IMiD on cell cycle inhibition. FIGS. 7E-F are graphs showing that treatment of multiple myeloma cells with Compound B and IMiDs resulted in synergistic increases in cellular apoptosis. FIG. 7E shows the effect of treatment of H929 myeloma cells for 4 days with DMSO, Compound B (2 µM), lenalidomide (2 µM), pomalidomide (1 µM), or combinations of Compound B with either IMiD on the induction of apoptosis. FIG. 7F shows the effect of treatment of MM.1s myeloma cells for 5 days with DMSO, Compound B (2 µM), lenalidomide (2 µM), pomalidomide (1 µM), or combinations of Compound B with either IMiD on the induction of apoptosis.

Figure 8E:
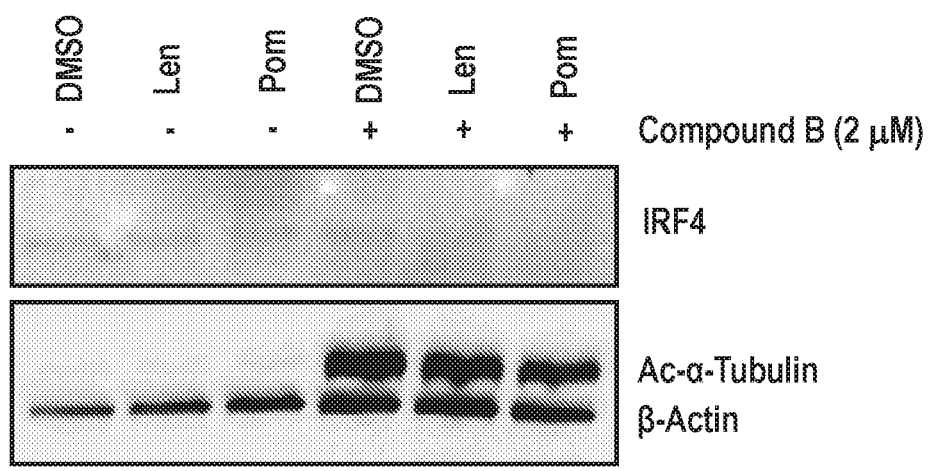

The combination of Compound B and pomalidomide (Compound F) led to suppression of Myc expression, a key transcriptional regulator in cancer. Markers of apoptosis (cleaved PARP and caspase) were increased, and suppressors of apoptosis, such as XIAP, were decreased by combination treatment. FIG. 8E is an image of an immunoblot confirming, at the protein level in H929 cells, the reduction of IRF4 after 48 hours of combination treatment with Compound B and either lenalidomide or pomalidomide relative to any of the single agents. Thus, treatment with IMiDs reduced expression of the critical genes MYC and IRF4, which were reduced even further by treatment with Compound B plus either IMiD. The molecular mechanism underlying this effect is currently being explored, though retention of low level inhibition of HDAC1, 2, and 3 by Compound B may contribute to the enhanced effects on gene expression reported here in combination with IMiDs.

Figure 4B:
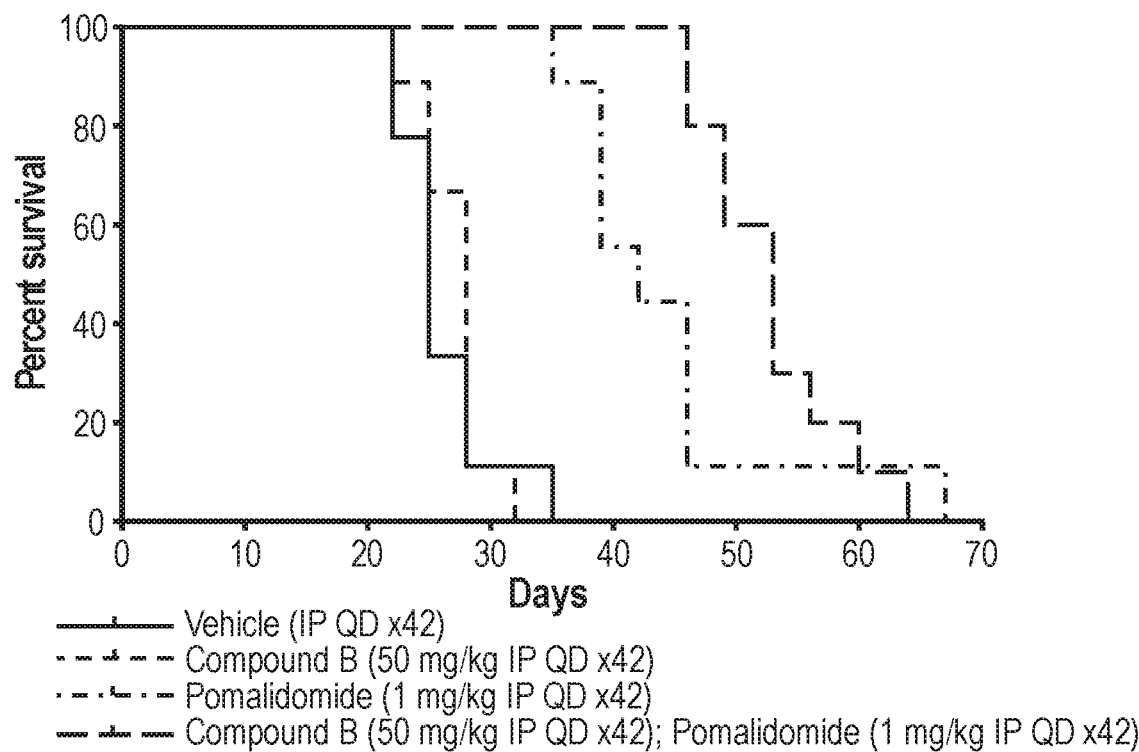
FIG. 4B is a graph that shows increased overall survival upon treatment of mice carrying H929 tumor xenografts with the combination of Compound B and pomalidomide relative to either single agent.
Figure 9B:
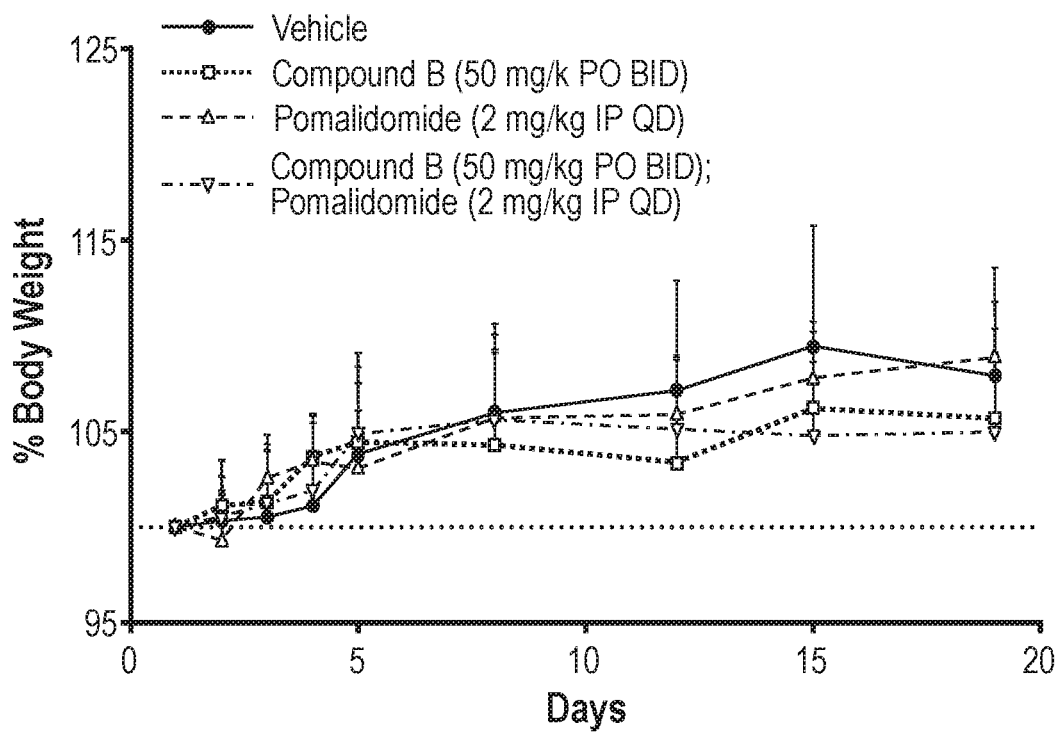
FIG. 9B is a graph showing the effects of treatment with Vehicle, Compound B alone, pomalidomide alone, or the combination of pomalidomide and Compound B on the body weight of CB17-SCID mice. All combination treatments were well tolerated with no overt evidence of toxicity.

Mice carrying H929 tumor xenografts were treated with DMSO, Compound B (50 mg/kg IP QD), pomalidomide (1 mg/kg IP QD), or the combination of Compound B (50 mg/kg IP QD) and pomalidomide (1 mg/kg IP QD) daily for up to 42 days. The combination showed increased overall survival relative to either single agent. See FIG. 4B. FIG. 9B is a graph showing the effects of treatment with Vehicle, Compound B alone, pomalidomide alone, or the combination of pomalidomide and Compound B on the body weight of CB17-SCID mice. These treatments were very well tolerated with no weight loss and no evidence of overt toxicity.

By demonstrating a similar tolerability and efficacy profile to ricolinostat (Compound A), these findings provide support for the clinical evaluation of Compound B in combination with IMiDs in MM patients.

Example 7

Expression Profiling Using Microarrays Reveals that a Combination of HDAC6-Selective Inhibitor and an IMiD Shows Greater Changes in Gene Expression in Multiple Myeloma Cells This example demonstrates that treating with an HDAC inhibitor (HDAC6-selective; Compound A) and with an IMiD (pomalidomide) in combination has a significant effect on gene expression in a multiple myeloma cell, H929, which is greater than when either agent is administered alone.

Figure 10:
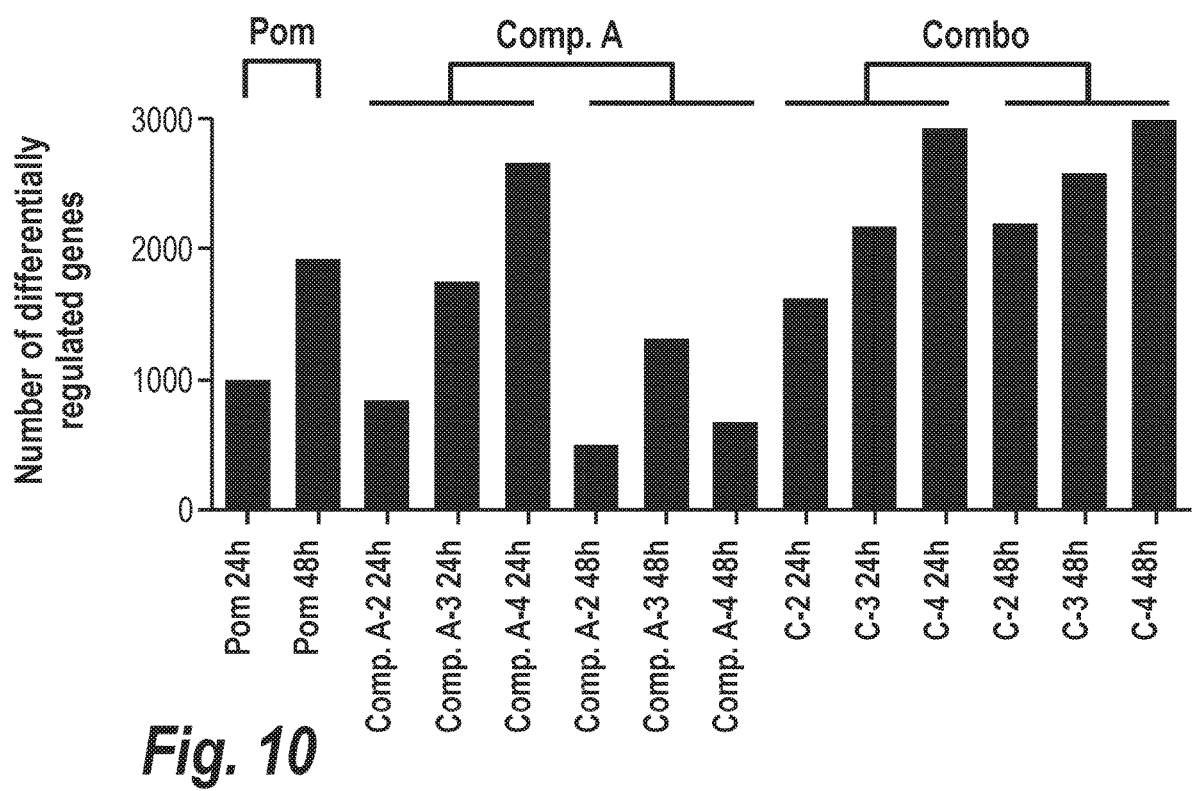
FIG. 10 is a summary graph showing the number of differentially regulated genes when multiple myeloma cells are treated with 1 µM pomalidomide ("Pom") or Compound A ("A") alone, or both agents in combination ("Combo") at 24 hours and 48 hours after treatment. The number of differentially regulated genes (y-axis) for each treatment (x-axis) relative to vehicle treated controls was determined using a fold change cut-off of 2-fold upregulated or 2-fold downregulated. Treating the cells with the combination of agents results in a greater number of differentially regulated genes, as does increasing the dose of Compound A (2, 3, or 4 µM).

The design of this experiment consisted of administering increasing doses of Compound A (0, 2, 3, 4 µM) in the presence or absence of a constant amount of pomalidomide (1 µM) and measuring changes in gene expression over time (up to 48 hours after cell treatment) using Affymetrix PRIMEVIEW™ chips (Affymetrix; Santa Clara, Calif.). The chip comprises a human gene expression array having more than 530,000 probes covering more than 36,000 transcripts and variants, which represent more than 20,000 genes mapped through RefSeq or via UniGene annotation. Table 1 shows the number of genes with fold expression changes greater than 2 relative to vehicle treatment. In the table, "A" indicates Compound A, and "Pom" indicates pomalidomide. FIG. 10 shows a graph that plots the totals from Table 1, showing the number of differentially regulated genes over time and drug treatment. It was also observed that unsupervised hierarchical clustering resulted in separation of treatment conditions; furthermore, treatment condition generated greater similarity among samples than did time or dose.

and in the (2) Library of Integrated Network-based Cellular Signatures (LINCS) database. GSEA is a computational method that determines whether an a priori defined set of genes shows statistically significant, concordant differences between two biological states; the LINCS database catalogues changes in gene expression and other cellular processes that occur when cells are exposed to a variety of perturbing agents against which lists of genes showing statistically significant, concordant difference between two biological states may be queried.

The goal of the GSEA was to identify gene sets that are enriched in combination treatment over single agent treatment. The strategy was to choose a database of lists to query, then run the combination of Compound A and pomalidomide against Compound A (4 µM) alone at 48 hours, as well as run the combination against pomalidomide (1 µM) alone at 48 hours. Relevant gene sets were those that were enriched in both queries in the same direction (increased or decreased). For this analysis, the "hallmark gene sets" was chosen as the database, which comprises coherently expressed signatures derived by aggregating many molecular signatures database (MSigDB) gene sets to represent well-defined biological states or processes.

FIG. 11 shows in part the results of the GSEA analysis, which show for positive enrichment that interferon responsive genes (interferon regulated genes) were highly enriched (ranked "1" and "2" in both combination vs. Compound A, 4 µM, at 48 hours (left column) and combination vs. pomalidomide at 48 hours (right column)), while for negative enrichment, myc targets where shown to be highly enriched (ranked "3" in combination vs. Compound A, 4 µM, at 48 hours (left column) and "1" in combination vs. pomalidomide at 48 hours (right column)). "Positively enriched" means significantly overrepresented at the top of a ranked list of fold-changes derived from a sample comparison; "negatively enriched" means significantly overrepresented at the bottom of a ranked list of fold-changes derived from a sample comparison.

FIGS. 12A-D shows in part the results of the GSEA analysis, wherein FIG. 12A shows a graph showing that interferon regulated gene expression was increased when cells were treated with the combination (Compound A and pomalidomide) vs. Compound A, 4 µM, at 48 hours, having a Normalized Enrichment Score (NES) of 2.89 and a False

TABLE 1

| | | | | | | | | | | | | | | |
|---|---|---|---|---|---|---|---|---|---|---|---|---|---|---|
| | \multicolumn{14}{c}{Fold changes in gene expression relative to vehicle} |
| | A-2 µM 24 h | A-3 µM 24 h | A-4 µM 24 h | Pom 24 h | Pom A-2 µM 24 h | Pom A-3 µM 24 h | Pom A-4 µM 24 h | A-2 µM 48 h | A-3 µM 48 h | A-4 µM 48 h | Pom 48 h | Pom A-2 µM 48 h | Pom A-3 µM 48 h | Pom A-4 µM 48 h |
| Up | 320 | 862 | 1010 | 448 | 970 | 1104 | 1701 | 365 | 464 | 325 | 1040 | 1221 | 1727 | 1861 |
| Down | 506 | 883 | 1635 | 531 | 646 | 1058 | 1213 | 139 | 853 | 341 | 865 | 964 | 851 | 1113 |
| Total | 826 | 1745 | 2645 | 979 | 1616 | 2162 | 2914 | 504 | 1317 | 666 | 1905 | 2185 | 2578 | 2974 |

Example 8

Certain Gene Sets are Enriched in Combination Treatment with an HDAC Inhibitor and an IMiD Over Single Agent Treatment in a Dose-Responsive Manner The data acquired from Example 7 was analyzed using two approaches: (1) Gene Set Enrichment Analysis (GSEA), Discovery Rate (FDR) of <0.001; similarly when the analysis examined the combination vs. pomalidomide alone at 48 hours, the NES is 2.62, with a similar FDR<0.001 (FIG. 12B). When examining myc targets (FIGS. 12C, D), negative enrichment was observed in both combination vs. Compound A alone, 4 µM, at 48 hours (NES=−2.34, FDR<0.001), and combination vs. pomalidomide alone at 48 hours (NES=−2.35, FDR<0.001). These data demonstrate that up-regulated genes by combination treatment are enriched in interferon regulated genes, while down-regulated genes are enriched in myc target genes.

FIGS. 12E-H show in part the results of the GSEA analysis, examining each agent, (Compound A) and pomalidomide, vs. the vehicle, dimethyl sulfoxide (DMSO). When interferon regulated genes were examined, it was observed that pomalidomide vs. DMSO at 48 hours increased expression of interferon regulated genes with a NES of 2.87, and an FDR <0.001 (FIG. 12E). Similarly, when Compound A was run against DMSO treated cells, interferon regulated gene expression was increased (NES=2.72, FDR<0.001; FIG. 12F). When myc targets were examined, pomalidomide vs. DMSO at 48 hours treatment showed a decrease in myc target gene expression (NES=−1.97, FDR<0.001; FIG. 12G) as did Compound A treatment when run against DMSO treated cells (NES=−2.23, FDR<0.001; FIG. 12H). These data demonstrate that up-regulated genes by each individual single agent treatment are enriched in interferon regulated genes, while down-regulated genes are enriched in myc target genes.

In the dose and time dependence analysis, FIGS. 13A-F summarizes the results. FIGS. 13A-C show the results of analysis of comparing treatment with the combination with increasing amounts of Compound A (2 µM, 3 µM, and 4 µM, respectively) at 24 hours compared to pomalidomide (1 µM) treated cells when interferon regulated genes are analyzed. The observed NES for each increasing dose of Compound A was 1.69, 2.18, and 2.38, respectively. Under these same conditions, but at 48 hours instead of 24 hours (FIGS. 13D-F), the observed NES for each increasing dose of Compound A was 1.48, 1.98, and 2.61, respectively. These results suggest that Compound A in each combination resulted in dose-dependent enrichment at both 24 and 48 hours for interferon regulated genes, and that maximum enrichment at 24 hours is sustained at 48 hours.

FIGS. 14A-F summarize the results of the dose and time dependence analysis when myc target genes are examined. FIGS. 14A-C show the results of analysis of comparing treatment with the combination with increasing amounts of Compound A (2 µM, 3 µM, and 4 µM, respectively) at 24 hours compared to pomalidomide (1 µM) treated cells when myc target genes are analyzed The observed NES for each increasing dose of Compound A was −1.53, −1.90, and −2.02, respectively. Under these same conditions, but at 48 hours instead of 24 hours (FIGS. 14D-F), the observed NES for each increasing dose of Compound A was −2.54, −2.49, and −2.35, respectively, with all having a FDR<0.001. These results suggest that there was both a dose- and time-dependent enrichment of the down-regulation of myc target genes by Compound A in the combination treatment.

Figure 15B:
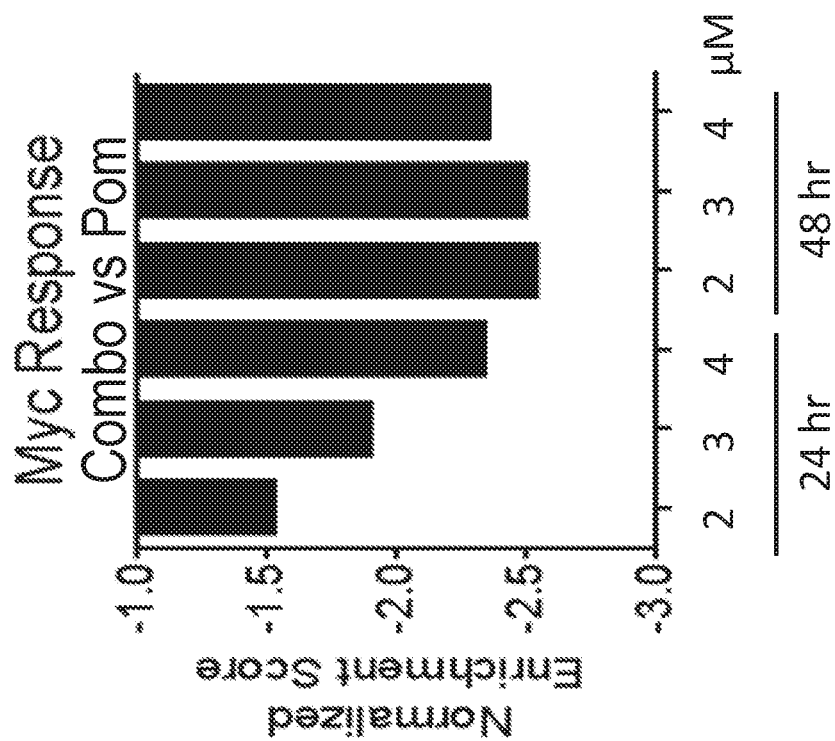
FIGS. 15A-B show summary graphs of the normalized enrichment score results shown in FIGS. 13A-F for interferon-regulated genes (FIG. 15A) and FIGS. 14A-F for c-myc target genes (FIG. 15B).
Figure 15A:
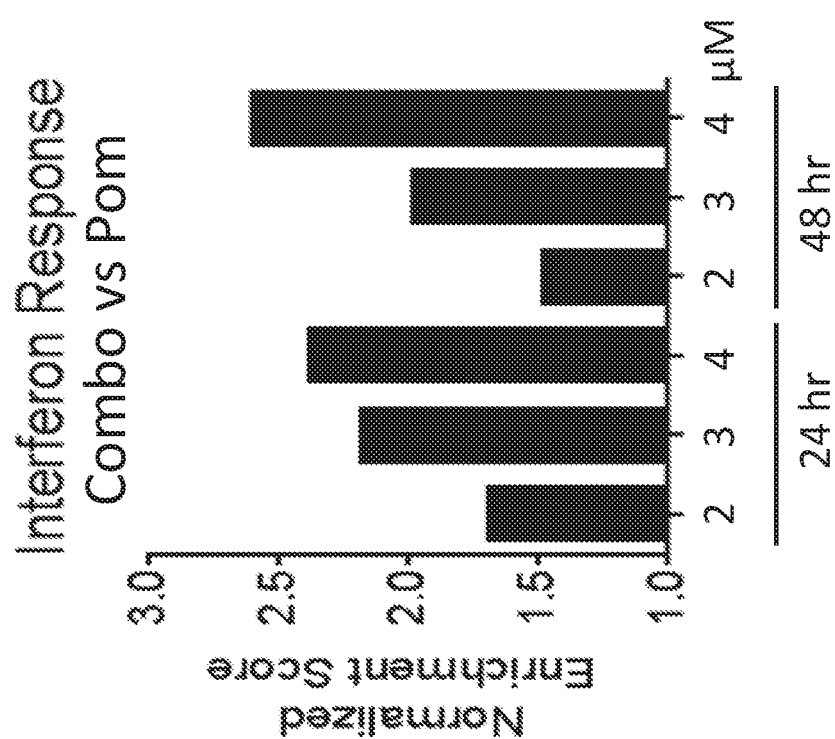

FIGS. 15A-B summarize the data from FIGS. 13 and 14, showing dose and time dependence summary graphs where the NES is plotted against time and Compound A dose. These data show that maximum positive enrichment in interferon regulated genes (24 hours; FIG. 15A) occurred before the maximum negative enrichment in myc target genes (48 hours; FIG. 15B); these data also show that enrichments in interferon regulated genes are dose-responsive, while myc target genes are both dose- and time-responsive (48 hr; FIGS. 15A, 15B).

Interferon regulated genes include: BST2, BTG1, C1R, CASP1, CCL7, CD47, CD86, CDKN1A, DDX58, DDX60, EIF2AK2, EPSTI1, FAS, GBP2, GMPR, HLA-B, HLA-DMA, HLA-DRB1, IFI27, IFI35, IFI44, IFI44L, IFIH1, IFIT1, IFIT3, ISG15, LATS2, LY6E, MX1, OAS1, OAS2, OAS3, PARP14, PARP9, PLA2G4A, PLSCR1, RAPGEF6, RIPK2, RSAD2, SAMD9, SP110, STAT1, STAT4, TAP1, TDRD7, TMEM140, TNFAIP3, TNFSF10, TXNIP, UBE2L6, USP18, and XAF1.

Myc target genes include: DDX18, DUSP2, GRWD1, HK2, HSPD1, IMP4, IPO4, MCM4, MRTO4, MYBBP1A, NIP7, NOLC1, NOP16, NOP2, PES1, PHB, PRMT3, PUS1, RABEPK, RRP12, RRP9, SLC19A1, SRM, TCOF1, TFB2M, UTP20, WDR43, and WDR74.

Example 9

Using LINCS Analysis, Interferon Regulated Gene Expression is Increased in Combination-Treated Cells Using an HDAC Inhibitor and an IMiD The Library of Integrated Network Based Cellular Signatures (LINCS) is a gene expression signature database derived from cell lines treated with compounds, gene knockdown, and exogenous gene expression. The database currently has 414,930 gene signatures (see www.commonfund.nih.gov/LINCS/index). The query application allows for the comparison of the data set from Example 7 to the LINCS database using a pattern matching algorithm. The query app takes as input a gene set comprised of up-regulated and down-regulated genes and computes the connectivity between these sets with all of the gene expression signatures in the LINCS database. While GSEA depends on a database (gene sets derived from various technologies and analysis strategies) to derive data, in using LINCS one starts by using data to query an established database (gene expression profiles derived from unified technology and analysis). GSEA and LINCS therefore use completely different databases and completely different inputs from the user. Thus, LINCS is an orthogonal approach to GSEA for global analysis of gene expression data.

In the LINCS analysis strategy used here, two gene sets were used to query against the LINCS database. Gene set #1 consisted of the data derived from running combination treatment vs. Compound A, 4 µM at 48 hours; genes that had a greater than two-fold change were selected, and duplicates removed. Gene set #2 consisted of the data derived from running combination treatment against pomalidomide treatment at 48 hours; again, genes that had a greater than two-fold change were selected, and duplicates removed. Relevant "hits" are those that are enriched in both queries.

When the queries were run, the results shown in Tables 2 and 3 were obtained. Table 2 shows the results from the combination treatment against pomalidomide treatment at 48 hours, and Table 3 shows the results of combination treatment vs. Compound A, 4 µM treatment, both at 48 hours. The tables are subdivided by signatures derived from "compound" application, "knockdown" application, and "overexpression" application. cmap name, the perturbagen; best2, the mean connectivity score across the two cell lines in which the perturbagen connected most strongly to the query; best4, the mean connectivity score across the four cell lines in which the perturbagen connected most strongly to the query; best6, the mean connectivity score across the six cell lines in which the perturbagen connected most strongly to the query; ncell, the number of cell lines over which the connectivity between the query and the perturbagen have been summarized; and nsig, the total number of perturbagen signatures over which its connectivity to the query has been summarized.

TABLE 2

Combination treatment vs. pomalidomide treatment at 48 hours

| | cmap name | best 2 | best 4 | best 6 | ncell | nsig |
|---|---|---|---|---|---|---|
| | Compound | | | | | |
| 1 | ISOX | 100.0 | 99.8 | 99.5 | 9 | 16 |
| 2 | THM-I-94 | 99.3 | 98.6 | 98.2 | 9 | 15 |
| 3 | pyroxamide | 99.3 | 98.6 | 98.1 | 9 | 13 |
| 4 | vorinostat | 98.2 | 98.0 | 97.5 | 9 | 687 |
| 5 | scriptaid | 99.4 | 98.5 | 97.4 | 9 | 35 |
| | Knockdown | | | | | |
| 1 | MYC | 99.7 | 99.2 | 98.1 | 9 | 11 |
| 2 | DDIT4 | 99.5 | 98.7 | 97.0 | 9 | 11 |
| 3 | HRAS | 98.8 | 97.8 | 96.2 | 9 | 11 |
| 4 | NT5E | 99.3 | 97.7 | 95.9 | 9 | 9 |
| 5 | POLR2A | 99.0 | 97.7 | 95.7 | 9 | 11 |
| | Overexpression | | | | | |
| 1 | IFNB1 | 100.0 | 99.6 | 98.8 | 9 | 9 |
| 2 | IFNG | 99.7 | 98.3 | 96.7 | 9 | 9 |
| 3 | CDX2 | 97.9 | 95.1 | 91.2 | 7 | 7 |
| 4 | CD40 | 94.7 | 89.4 | 84.8 | 8 | 8 |
| 5 | KLF6 | 98.3 | 94.0 | 83.1 | 8 | 16 |

TABLE 3

Combination vs. Compound A, 4 μM at 48 hours

| | cmap name | best 2 | best 4 | best 6 | ncell | nsig |
|---|---|---|---|---|---|---|
| | Compound | | | | | |
| 1 | BMS-754807 | 99.7 | 99.0 | 96.1 | 9 | 17 |
| 2 | cucurbitacin-i | 97.1 | 95.9 | 94.9 | 9 | 37 |
| 3 | WZ-4-145 | 98.3 | 96.9 | 94.7 | 9 | 13 |
| 4 | TG-101348 | 98.7 | 97.9 | 94.5 | 9 | 22 |
| 5 | aminopurvalanol-a | 97.7 | 96.0 | 94.1 | 9 | 24 |
| | Knockdown | | | | | |
| 1 | CDK4 | 99.8 | 99.5 | 98.7 | 9 | 10 |
| 2 | MYC | 99.5 | 99.2 | 98.4 | 9 | 11 |
| 3 | RUVBL1 | 99.8 | 99.0 | 97.8 | 9 | 11 |
| 4 | RYK | 99.8 | 98.6 | 96.6 | 8 | 10 |
| 5 | MTHFD2 | 98.8 | 98.1 | 96.4 | 9 | 11 |
| | Overexpression | | | | | |
| 1 | KLF6 | 99.4 | 98.0 | 97.1 | 8 | 16 |
| 2 | IFNB1 | 99.1 | 97.6 | 96.4 | 9 | 9 |
| 3 | IFNG | 100.0 | 98.6 | 95.7 | 9 | 9 |
| 4 | CDKN2C | 99.1 | 97.5 | 93.5 | 7 | 7 |
| 5 | BCL10 | 97.7 | 95.4 | 91.5 | 8 | 8 |

When analyzing the results shown in Tables 2 and 3, the following were found enriched for increased expression in both queries: IFNB1, IFNG, and KLF6 (see the "Overexpression" category for each table). Likewise, when analyzing for decreased expression, "myc" was found in both queries (see "Knockdown" category for each table).

These data, along with those from Example 8, demonstrate that Compound A or pomalidomide as single agents induce interferon regulated genes and suppress myc target genes. The combination of Compound A with pomalidomide leads to a greater suppression of the myc signature than either treatment alone. The combination of Compound A with pomalidomide leads to a greater induction of an interferon signature than either treatment alone.

Example 10

Identification of Absolute Fold Changes in Gene Expression Between Combination Treatment and Vehicle Treatment: Top Gene Expression Changes; Verification of Selected Genes In this example, absolute fold changes in gene expression were examined. Using the data obtained in Example 7, the following criteria were set for identifying absolute fold changes in probe set expression level:
  (1) Combination (Compound A, 4 μM with pomalidomide, 1 μM), the change in expression needed to be at least 1.5-fold in the same direction, vs. both single agents.
  (2) Combination, the change in expression needed to be at least 3-fold, vs. vehicle (DMSO).

When these data were examined, there were 71 transcript qualifiers that exhibited decreased expression, and 339 transcript qualifiers that exhibited increased expression. An example of a gene that had reduced expression was BIRC5. Examples of genes that were found to have up-regulated expression included PBX1, IFIT3, CASP1, GABRR1, CCL4L1, HSD11B1, PBX1, XAF1, IFIT1, SEPP1, PARP14, CCL4, and IFI27. Of these up-regulated genes, IFIT3, CASP1, XAF1, IFIT1, PARP14, XAF1, and IFI27 are interferon regulated genes. The following genes were chosen for further study: BIRC5, CASP1, XAF1, and CCL4.

Figure 16A:
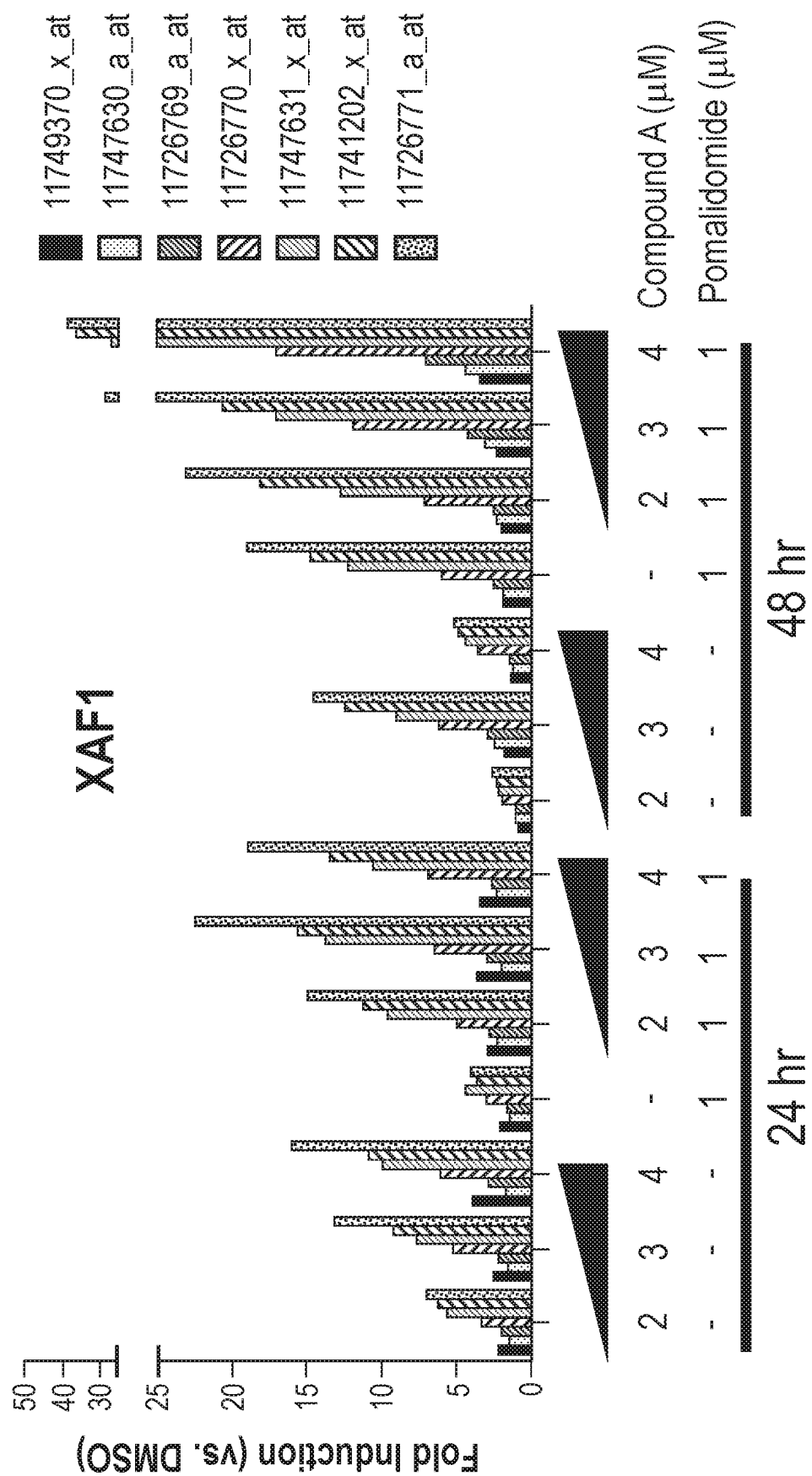
FIGS. 16A-D show graphs that summarize the results of expression analyses of specific genes that are either up-regulated or down-regulated when treated by the combination of Compound A and pomalidomide (1 µM), with increasing amounts of Compound A (2 µM, 3 µM, and 4 µM).
Figure 16B:
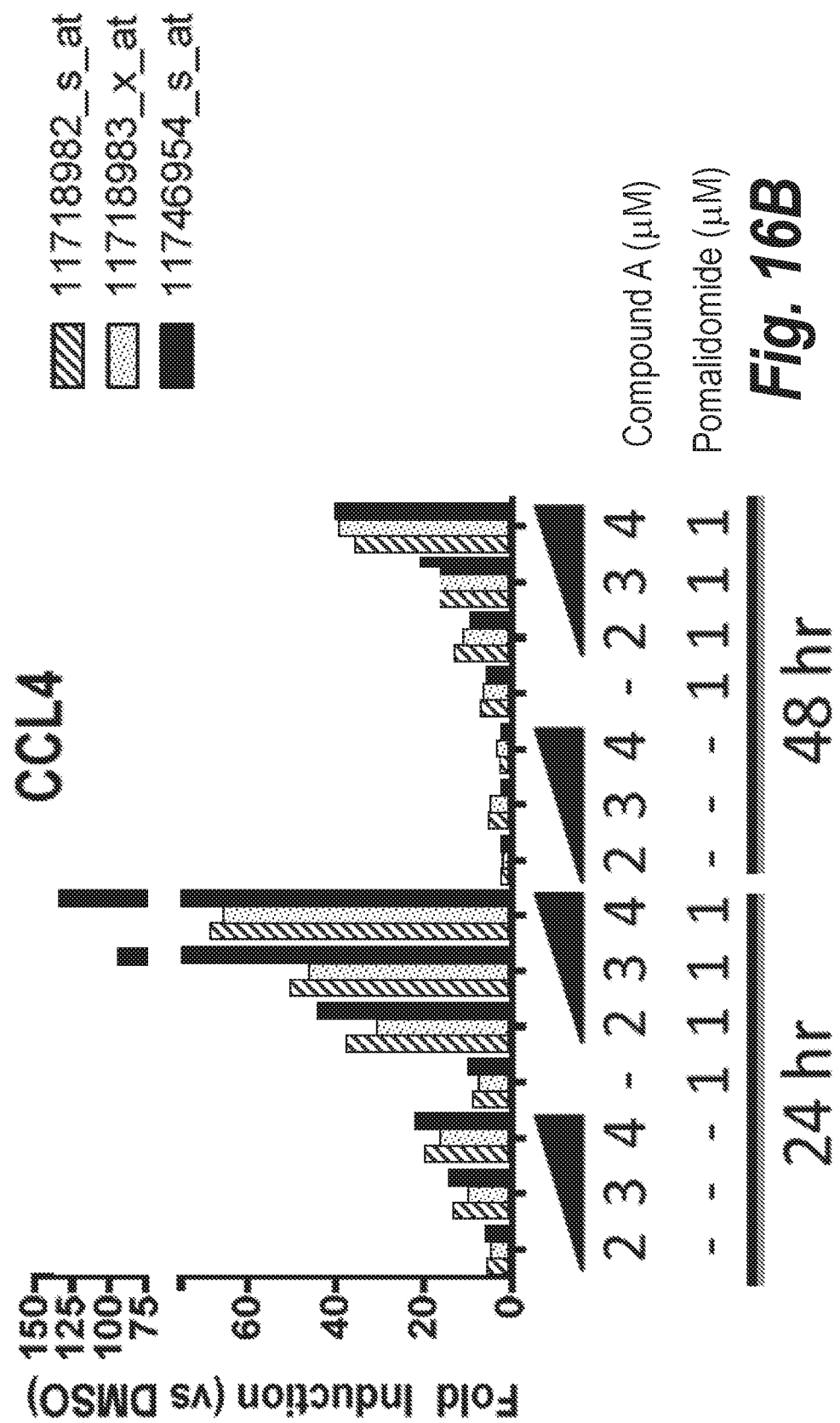

When XAF1 and CCL4 expression was analyzed for cells treated with Compound A, pomalidomide, or both, with increasing concentrations of Compound A, the results shown in FIGS. 16A, B were obtained after 24 hour and 48 hour treatment. Each bar in each group of bars per treatment represents individual transcript probes for measuring gene expression level. FIG. 16A shows the results for XAF1, and FIG. 16B shows the results for CCL4. Both genes showed consistent dose-dependent induction by Compound A and small induction by pomalidomide alone. In combination, there was a further dose-dependent induction with increasing dose of Compound A, and at levels far higher than using each agent alone. Finally, there also appeared to be independent time components for each transcript.

Figure 16C:
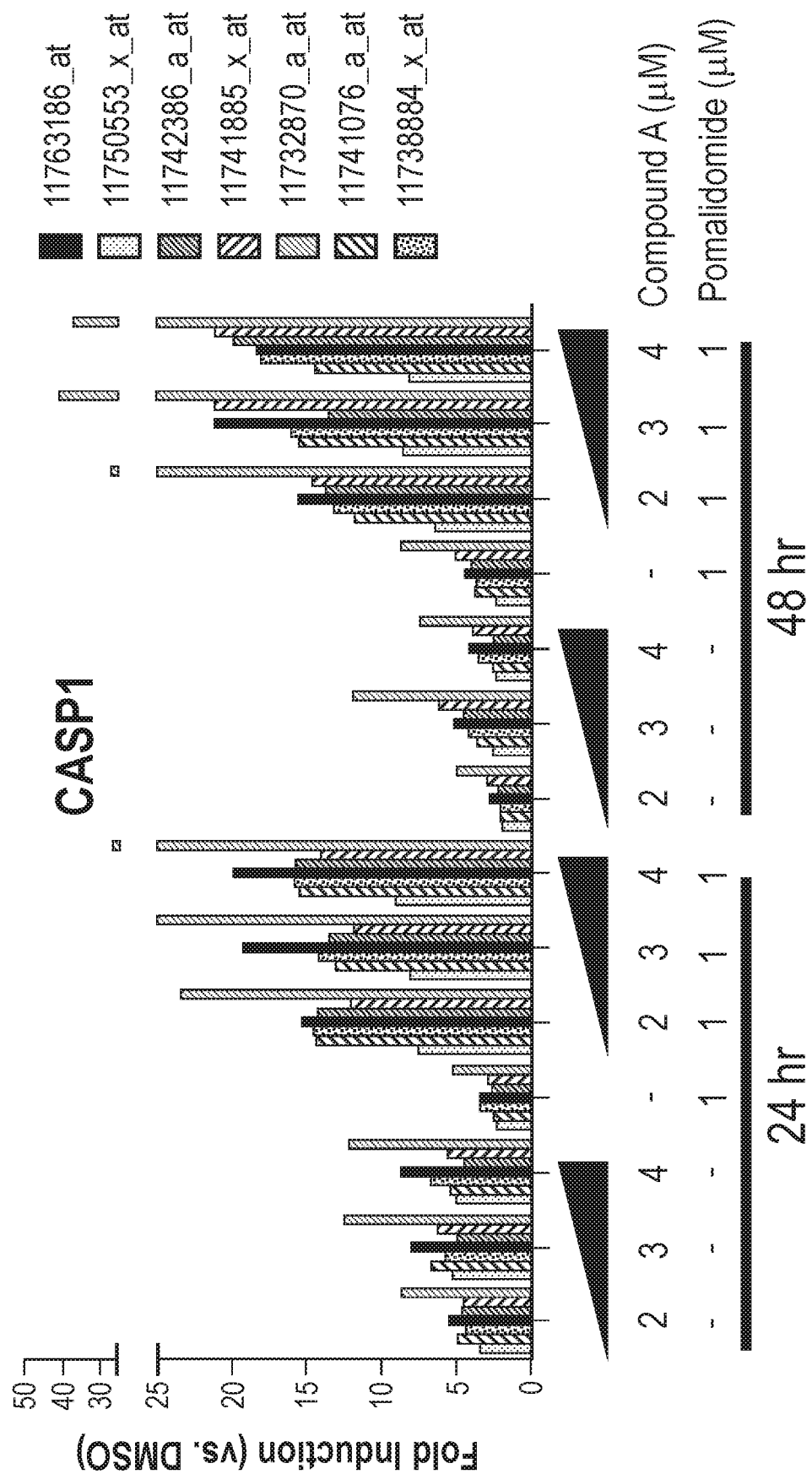
Figure 16D:
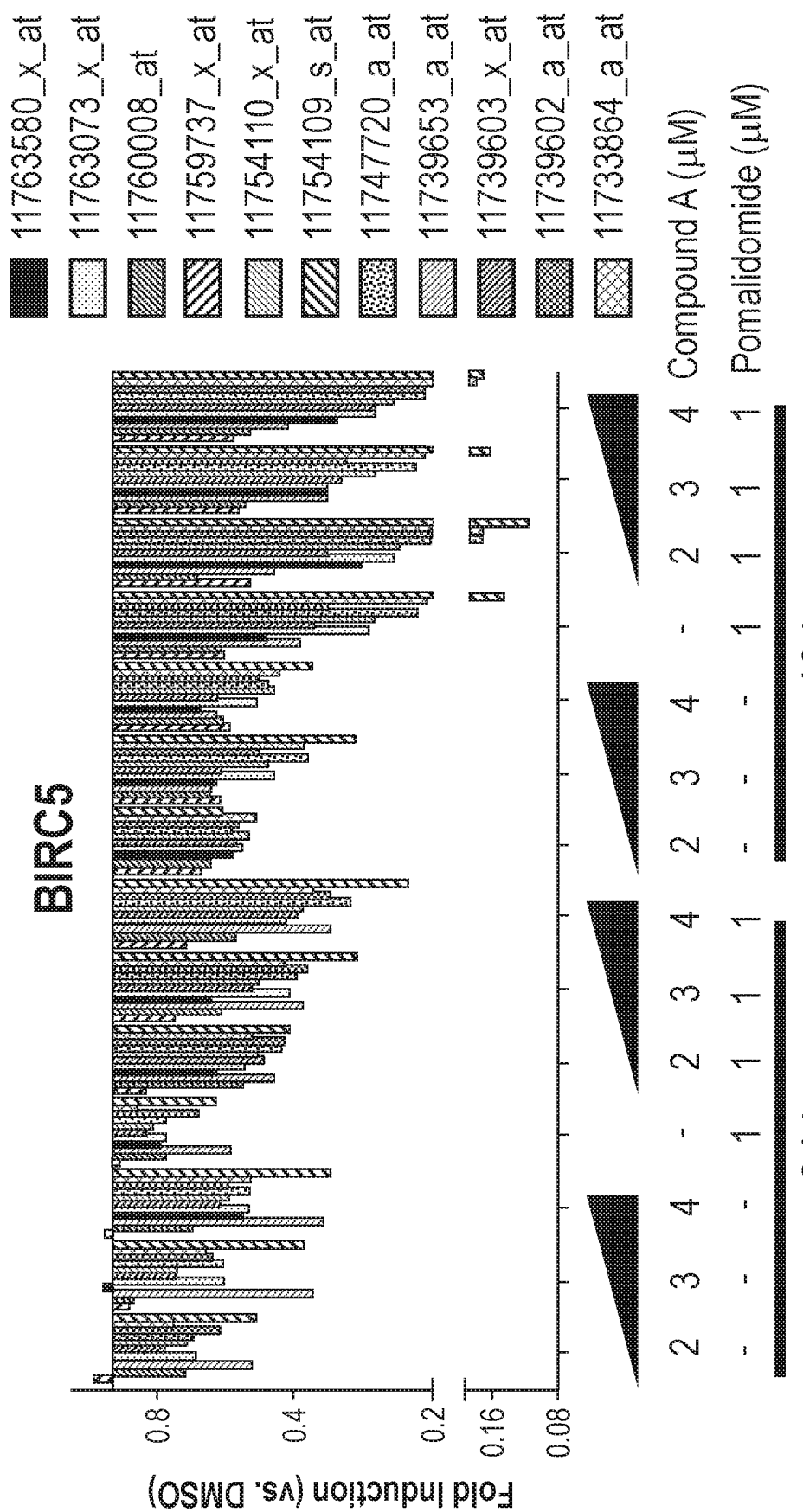

When the same analyses were run for CASP1 and BIRC5 (also known as survivin), the results shown in FIGS. 16C, D were obtained. FIG. 16C shows the results for CASP1, and FIG. 16D shows the results for BIRC5. These results show that both genes had consistent dose-dependent effect of Compound A and relatively small change by pomalidomide alone. Furthermore, in combination, there was still a dose-dependent effect with increasing dose of Compound A, and at levels far higher than either agent alone. Finally, both effects were enhanced with time, though dose-dependence was less clear at 48 hours.

XAF1 (XIAP-associated factor 1) is a negative regulator of members of the inhibitor of apoptosis protein (IAP) family. It promotes redistribution of BIRC4 from the cytoplasm to the nucleus; this action is thought to be independent of BIRC4 inactivation. The BIRC4-XAF1 complex mediates down-regulation of BIRC5/survivin; the process requires the E3 ligase activity of BIRC4. XAF1 may act as a tumor suppressor by mediating apoptosis resistance of cancer cells.

CCL4 (C-C motif chemokine 4/MIP-1β) is a monokine with inflammatory and chemokinetic properties, binding to the chemokine receptor, CCR5. CCL4 is one of the major HIV-suppressive factors produced by CD8+ T-cells. Recombinant CCL4 induces a dose-dependent inhibition of different strains of HIV-1, HIV-2, and simian immunodeficiency virus (SIV). The processed form CCL4(3-69) retains the abilities to induce down-modulation of surface expression of the chemokine receptor CCR5 and to inhibit CCR5-mediated entry of HIV-1 in T-cells. CCL4 has been linked to recruitment of T cells to tumors.

Caspase-1 (CASP1) is a thiol protease that cleaves IL-10, releasing the mature cytokine which is involved in a variety of inflammatory processes. It is important for defense against pathogens. Caspase-1 can also promote apoptosis; caspase-1 inhibitors inhibit cell death in mammals and other vertebrates.

Survivin has dual roles in promoting cell proliferation and preventing apoptosis. It is essential for chromosome alignment and segregation during mitosis and cytokinesis. Survivin may counteract a default induction of apoptosis in G2/M phase. The acetylated from represses STAT3 transactivation of target gene promoters. Survivin is an inhibitor of CASP3 and CASP7. It is abundantly expressed in adenocarcinoma (lung, pancreas, colon, breast, and prostate) and in high-grade lymphomas.

In summary, the data from Examples 7-10 show the following. Expression profiling suggests both Compound A and pomalidomide treatments repress gene sets downstream of myc target genes and increase interferon regulated genes. Both sets of signatures are further impacted upon combination treatment. IKZF3 may directly bind and repress the promoters of these genes because HDAC1/2 has been observed to be in complex with IKZF3, thus inhibition of Class I HDACs may enhance the derepression of these genes independent of IMiD-mediated degradation of IKZF1/3.

Example 11

Synthesis of 2-(diphenylamino)-N-(7-(hydroxyamino)-7-oxoheptyl) pyrimidine-5-carboxamide (Compound A)

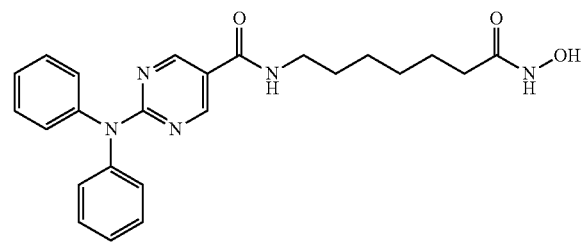 [SMILES: O=C(CCCCCCNC(=O)c1cnc(N(c2ccccc2)c2ccccc2)nc1)NO]

Reaction Scheme

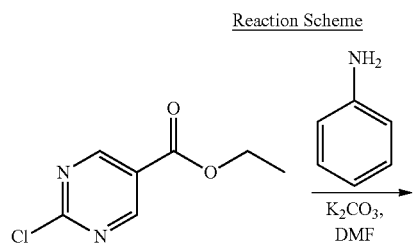

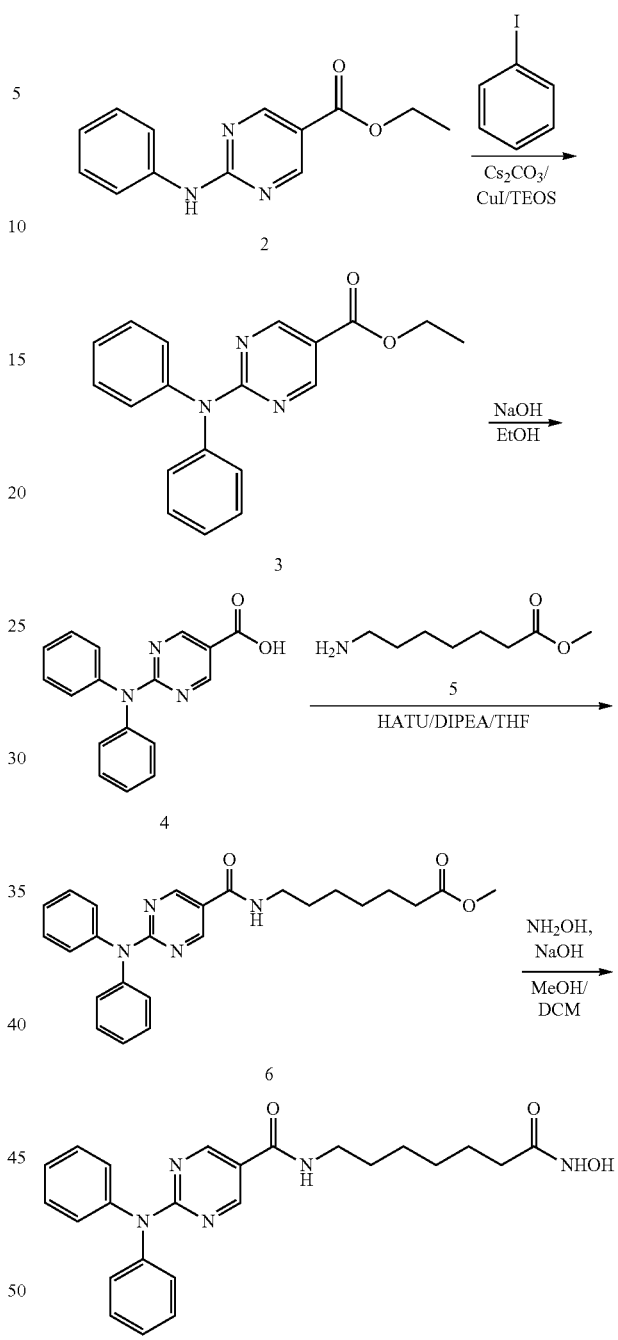

Synthesis of Intermediate 2

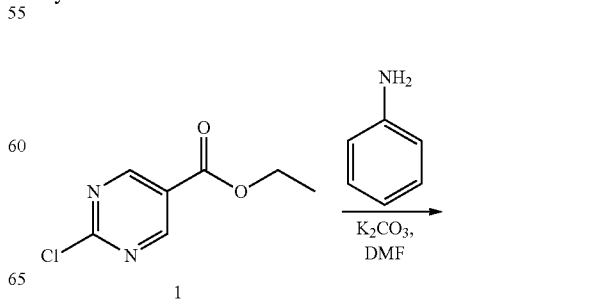

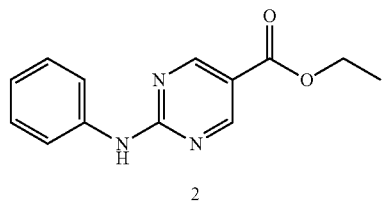

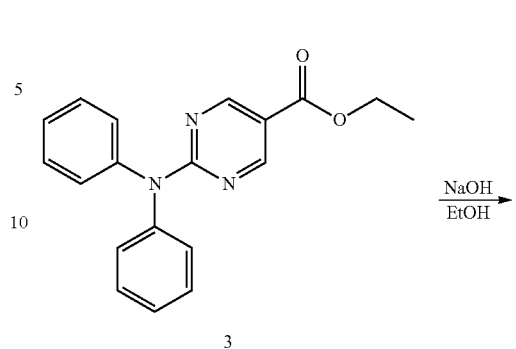

Synthesis of Intermediate 4

A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3

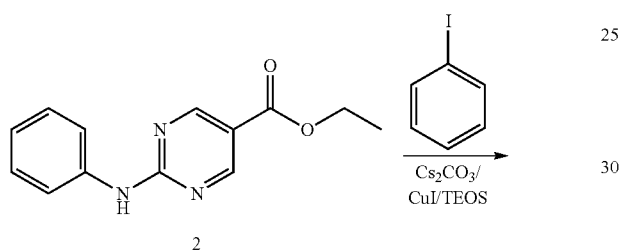

2 N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2 N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 6

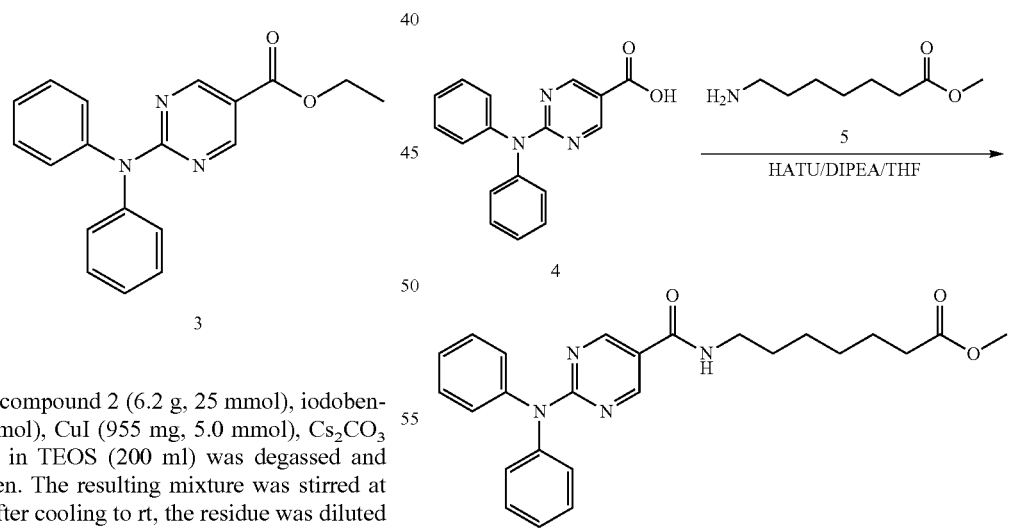

A mixture of the compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 h. After cooling to rt, the residue was diluted with EtOAc (200 ml) and 95% EtOH (200 ml), $NH_4F$—$H_2O$ on silica gel [50 g, pre-prepared by the addition of $NH_4F$ (100 g) in water (1500 ml) to silica gel (500g, 100-200 mesh)] was added, and the resulting mixture was kept at rt for 2 h, the solidified materials was filtered and washed with EtOAc. The filtrate was evaporated to dryness and the residue was purified by silica gel chromatography (petroleum ethers/EtOAc=10/1) to give a yellow solid (3 g, 38%).

A mixture of compound 4 (2.5 g, 8.58 mmol), aminoheptanoate 5 (2.52 g, 12.87 mmol), HATU (3.91 g, 10.30 mmol), DIPEA (4.43 g, 34.32 mmol) was stirred at rt overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide

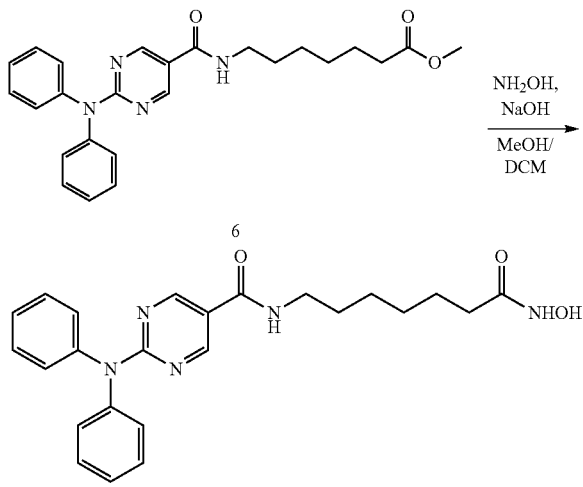

A mixture of the compound 6 (2.0 g, 4.6 mmol), sodium hydroxide (2 N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at rt for 20 min. After removal of the solvent, the mixture was neutralized with 1 M HCl to give a white precipitate. The crude product was filtered and purified by pre-HPLC to give a white solid (950 mg, 48%).

Example 12

Synthesis of 2-((2-chlorophenyl)(phenyl)amino)-N-(7-(hydroxyamino)-7-oxoheptyl)pyrimidine-5-carboxamide (Compound B)

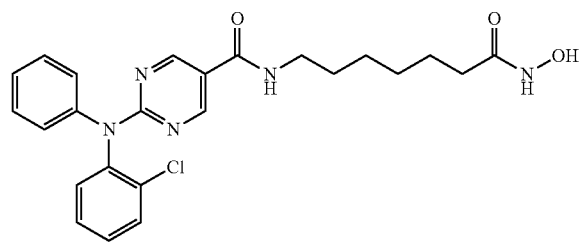 [SMILES: O=C(CCCCCCNC(=O)c1cnc(N(c2ccccc2)c2ccccc2Cl)nc1)NO]

Reaction Scheme:

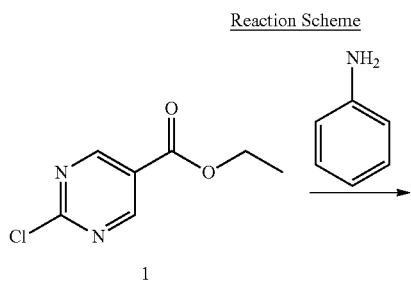

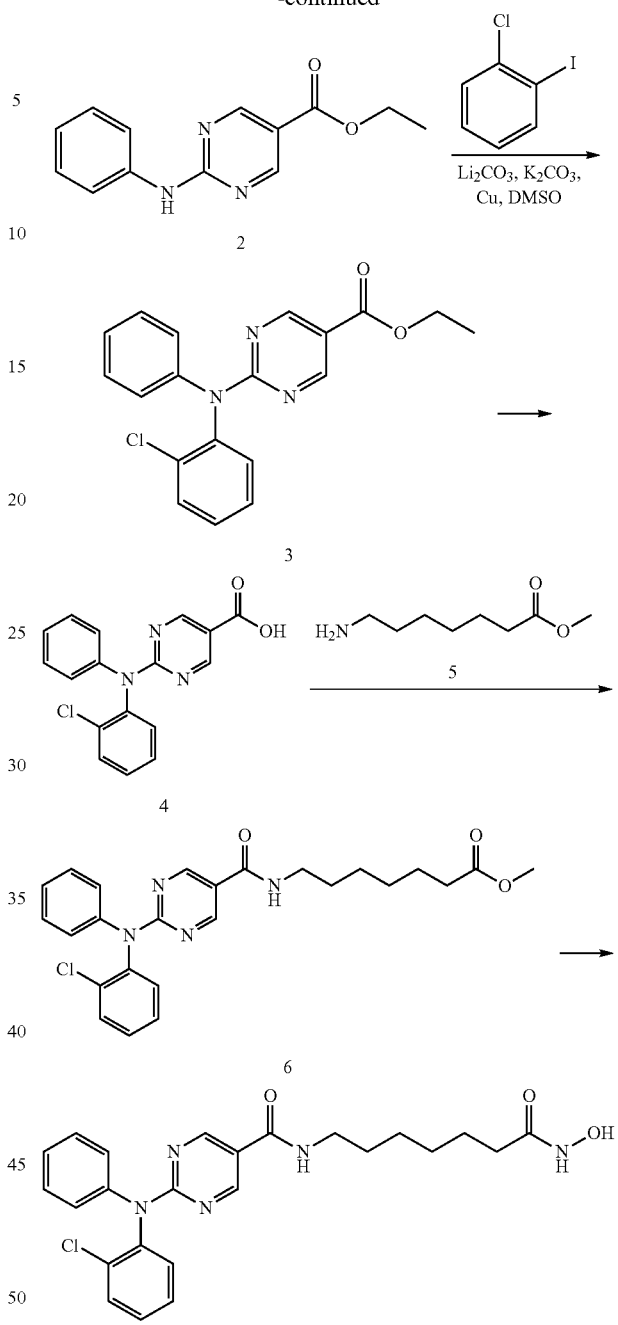

Synthesis of Intermediate 2: See synthesis of intermediate 2 in Example 1.

Synthesis of Intermediate 3: A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4: See synthesis of intermediate 4 in Example 1.

Synthesis of Intermediate 6: See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B): See synthesis of Compound A in Example 1.

Example 13

Synthesis of 2-41-(3-fluorophenyl)cyclohexyl)amino)-N-hydroxypyrimidine-5-carboxamide (Compound C)

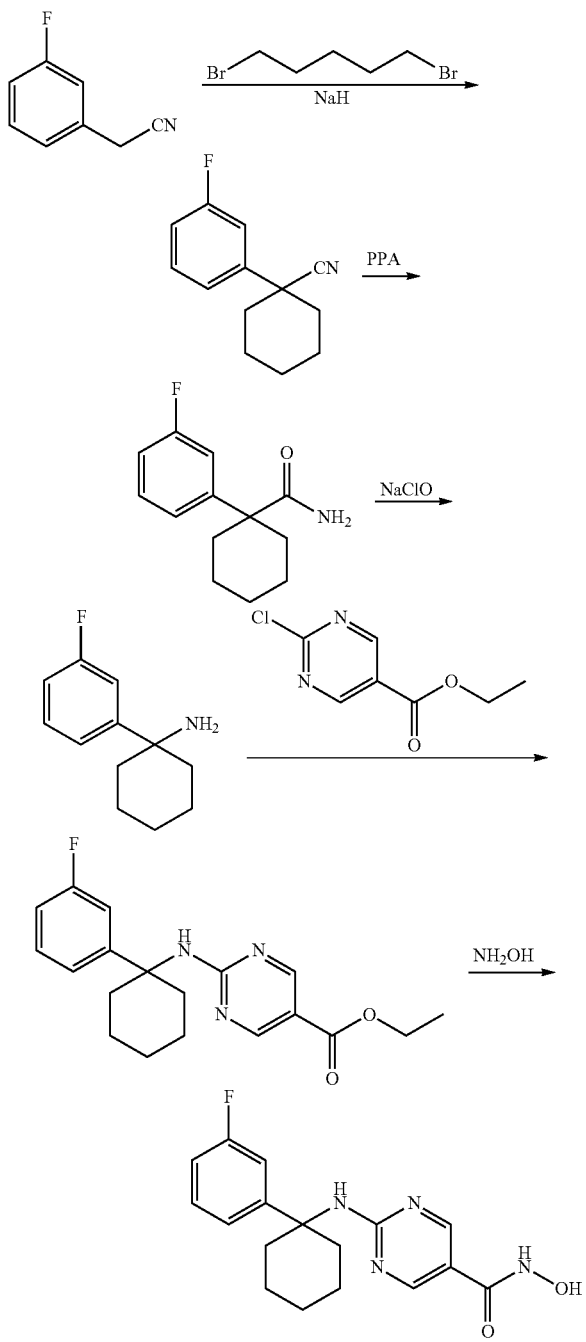

Synthesis of 1-(3-fluorophenyl)cyclohexanecarbonitrile:
To a solution of 2-(3-fluorophenyl)acetonitrile (100 g, 0.74 mol) in Dry DIVIF (1000 ml) was added 1,5-dibromopentane (170 g, 0.74 mol), NaH (65 g, 2.2 eq) was added dropwise at ice bath. After addition, the resulting mixture was vigorously stirred overnight at 50° C. The suspension was quenched by ice water carefully, extracted with ethyl acetate (3*500 ml). The combined organic solution was concentrate to afford the crude which was purified on flash column to give 1-(3-fluorophenyl)cyclohexanecarbonitrile as pale solid (100 g, 67%).

Synthesis of 1-(3-fluorophenyl)cyclohexanecarboxamide:
To a solution of 1-(3-fluorophenyl)cyclohexanecarbonitrile (100 g, 0.49 mol) in PPA (500 ml) was heated at 110° C. for about 5-6 hours. After completed, the resulting mixture was carefully basified with sat.NaHCO3 soultion until the PH=8-9. The precipitate was collected and washed with water (1000 ml) to afford 1-(3-fluorophenyl)cyclohexanecarboxamide as white solid (95 g, 87%).

Synthesis of 1-(3-fluorophenyl)cyclohexanamine:
To a solution of 1-(3-fluorophenyl)cyclohexanecarboxamide (95 g, 0.43 mol) in n-BuOH (800 ml) was added NaC10 (260 ml, 1.4 eq), then 3N NaOH (400 ml, 2.8 eq) was added at 0° C. and the reaction was stirred overnight at r.t. The resulting mixture was extracted with EA (2*500 ml), the combined organic solution was washed with brine, dried to afford the crude which was further purification on treating with HCl salt as white powder (72 g, 73%).

Synthesis of ethyl 2-(1-(3-fluorophenyl)cyclohexylamino)pyrimidine-5-carboxylate:
To a solution of 1-(3-fluorophenyl)cyclohexanamine hydrochloride (2.29 g 10 mmol) in Dioxane (50 ml) was added ethyl 2-chloropyrimidine-5-carboxylate (1.87 g, 1.0 eq) and DIPEA (2.58 g, 2.0 eq). The mixture was heated overnight at 110-120° C. The resulting mixture was directly purified on silica gel column to afford the coupled product as white solid (1.37 g, 40%)

Synthesis of 2-((1-(3-fluorophenyl)cyclohexyl)amino)-N-hydroxypyrimidine-5-carboxamide:
To a solution of ethyl 2-(1-(3-fluorophenyl)cyclohexylamino)pyrimidine-5-carboxylate (100 mg, 0.29 mmol) in MeOH/DCM (10 ml, 1:1) was added 50% NH$_2$OH in water (2 ml, excess), then sat. NaOH in MeOH (2 ml, excess) was added at 0° C. and the reaction was stirred for 3-4 hours. After completed, the resulting mixture was concentrated and acidified with 2 N HCl to the PH=4-5. The precipitate was collected and washed by water (10 ml) to remove the NH$_2$OH and dried to afford 2-((1-(3-fluorophenyl)cyclohexyl)amino)-N-hydroxypyrimidine-5-carboxamide as white powder (70 mg, 73%).

Example 14

Synthesis of N-hydroxy-2-((1-phenylcyclopropyl)amino)pyrimidine-5-carboxamide (Compound D)

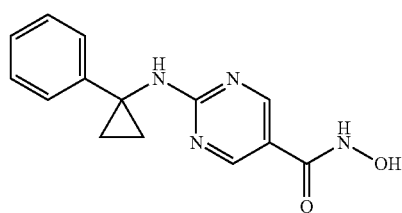 [SMILES: O=C(NO)c1cnc(NC2(c3ccccc3)CC2)nc1]

Reaction Scheme

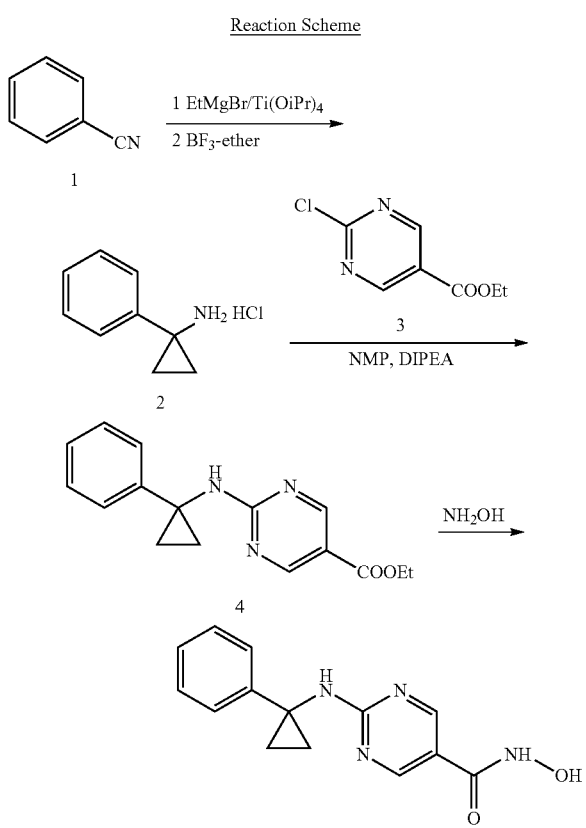

Synthesis of Intermediate 2: A solution of compound 1, benzonitrile, (250 g, 1.0 equiv.), and Ti(OiPr)$_4$ (1330 ml, 1.5 equiv.) in MBTE (3750 ml) was cooled to about −10 to −5° C. under a nitrogen atmosphere. EtMgBr (1610 ml, 3.0 M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1 N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3 L×2) and EtOAc (3 L×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4: Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl)amino)pyrimidine-5-carboxamide (Compound D): A solution of MeOH (1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr, and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6 N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Incorporation by Reference

The contents of all references (including literature references, issued patents, published patent applications, and patent applications) cited throughout this application are hereby expressly incorporated herein in their entireties. Unless otherwise defined, all technical and scientific terms used herein are accorded the meaning commonly known to one with ordinary skill in the art.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for increasing the expression of interferon-regulated genes in multiple myeloma cells comprising
    (a) co-administering a therapeutically effective amount of a histone deacetylase 6 (HDAC6)-selective inhibitor and an immunomodulatory drug (IMiD) to a subject in need thereof, wherein the HDAC6-selective inhibitor is

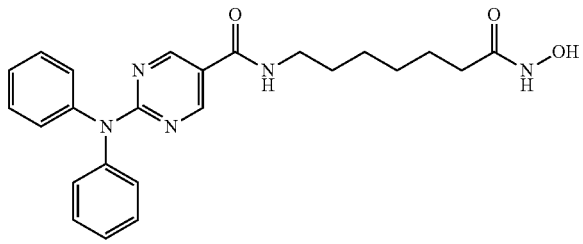 [SMILES: O=C(CCCCCCNC(=O)c1cnc(N(c2ccccc2)c2ccccc2)nc1)NO]

or a pharmaceutically acceptable salt thereof; or

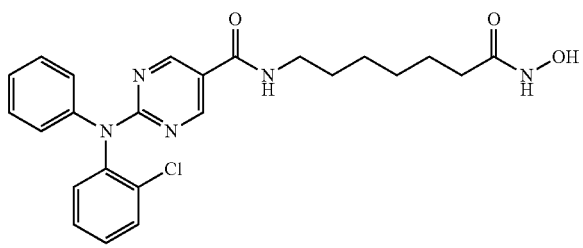

or a pharmaceutically acceptable salt thereof;
wherein the IMiD is

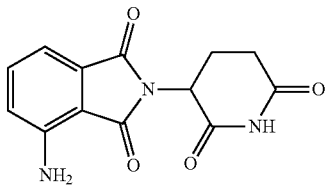

or a pharmaceutically acceptable salt thereof; or

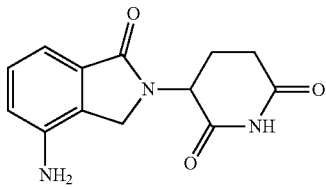

or a pharmaceutically acceptable salt thereof; and (b) measuring the expression level of a gene selected from the group consisting of C-C motif chemokine 4 (CCL4; MIP-1β), caspase-1 (CASP1), interferon α-inducible protein 27 (IFI27), interferon-induced protein with tetratricopeptide repeats 1 (IFIT1), interferon-induced protein with tetratricopeptide repeats 3 (IFIT3), poly (ADP-ribose) polymerase family member 14 (PARP 14), and XIAP-associated factor 1 (XAF1);

wherein the interferon is interferon gamma or alpha, and wherein the expression level of the gene is increased if the expression level of the gene is greater than 2 fold as compared to the expression level of the gene in vehicle treated cells.

2. The method of claim 1, wherein the co-administration of the HDAC6-selective inhibitor and the IMiD results in a synergistic increase in the expression of genes regulated by interferon in the cancer cells.

3. The method of claim 1, wherein the cancer cells are multiple myeloma cells, diffuse large B-cell lymphoma cells, indolent lymphoma cells, follicular lymphoma cells, chronic lymphocytic leukemia cells, or mantle cell lymphoma cells.

4. The method of claim 3, wherein the multiple myeloma is a relapsed or refractory multiple myeloma.

5. The method of claim 1, wherein the co-administration of the HDAC6-selective inhibitor and the IMiD acts in synergy with a chemotherapeutic agent or an immunotherapeutic agent to increase apoptosis of the cancer cells.

6. The method of claim 1, wherein the co-administration of the HDAC6-selective inhibitor and the IMiD inhibits BIRC5 (survivin) gene expression in the cancer cells.

7. The method of claim 1, wherein the greater than 2 fold expression level indicates that the amount of the HDAC6-selective inhibitor and the amount of the IMiD are effective.

* * * * *